US008629277B2

(12) United States Patent
Sivakumar et al.

(10) Patent No.: US 8,629,277 B2
(45) Date of Patent: Jan. 14, 2014

(54) STYRENYL 1,2,4-OXADIAZOLE COMPOUNDS

(75) Inventors: Meenakshi Sivakumar, Mumbai (IN); Kalpana Sanjay Joshi, Mumbai (IN); Valmik Sopan Aware, Mumbai (IN); Ankush Gangaram Sarde, Mumbai (IN); Sandeep Maruti Bagul, Navi Mumbai (IN); Sonal Mohan Manohar, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 13/580,928

(22) PCT Filed: Feb. 24, 2011

(86) PCT No.: PCT/IB2011/050770
§ 371 (c)(1),
(2), (4) Date: Aug. 23, 2012

(87) PCT Pub. No.: WO2011/104680
PCT Pub. Date: Sep. 1, 2011

(65) Prior Publication Data
US 2013/0005771 A1    Jan. 3, 2013

Related U.S. Application Data

(60) Provisional application No. 61/307,974, filed on Feb. 25, 2010.

(51) Int. Cl.
*C07D 413/06* (2006.01)
*C07D 271/06* (2006.01)

(52) U.S. Cl.
USPC ............................. 546/209; 548/131

(58) Field of Classification Search
USPC ............................. 546/209; 548/131
See application file for complete search history.

(56) References Cited

U.S. PATENT DOCUMENTS 7,521,175 B2    4/2009    Sawyers et al.

FOREIGN PATENT DOCUMENTS

WO    2008/026125 A2    3/2008
WO    WO 2008097538 A1 *    8/2008

OTHER PUBLICATIONS

Chemical Abstract Service (CAS) Registry Numbers (RN) Entered STN: Jul. 13, 2004 to Sep. 17, 2009.*
Kumar, D. et al. "Synthesis and anticancer activities of novel 3,5-disubstituted-1,2,4-oxadiazoles." Bioorg. Med. Chem. Lett. 2009, 19, 2739-2741, published Apr. 5, 2009.*

Shih, I.-M. and Wang, T.-L. "Notch signaling, gamma-secretase inhibitors, and cancer therapy." Cancer Res. 2007, 67, 1879-1882, published Mar. 1, 2007.*
Chen, C.S. et al. "Design, synthesis and biological evaluation of heterocycle-conjugated styrene derivatives as protein tyrosine kinase inhibitors and free radical scavengers." Chinese Pharmaceutical Journal 2002, 54, 353-374 (Abstract).*
Patrick, Graham L., An introduction to Medicinal Chemistry, Second Edition, Oxford University Press, (2001), pp. 239-248.
Burnette, W. Neal, "'Western Blotting': Electrophoretic Transfer of Proteins from Sodium Dodecyl Sulfate-Polyacrylamide Gels to Unmodified Nitrocellulose and Radiographic Detection with Antibody and Radioiodinated Protein A", Analytical Biochemistry, 112, (1981), pp. 195-203.
Deegan, Tracy L., et al., "Parallel Synthesis of 1,2,4-Oxadiazoles Using CDI Activation", Bioorganic & Medicinal Chemistry Letters 9, (1999), pp. 209-212.
Koufaki, Maria, et al., "Synthesis of a second generation chroman/catechol hybrids and evaluation of their activity in protecting neuronal cells from oxidative stress-induced cell death", Bioorganic & Medicinal Chemistry 18 (2010), pp. 3898-3909.
Donato, Nicholas J., et al., "BCR-ABL independence and LYN kinase overexpression in chronic myelogenous leukemia cells selected for resistance to STI571", American Society of Hematology 101, (2003), pp. 690-698.
Chen, Jian-Hong, et al., "Inhibitory effect of caffeic acid phenethyl ester on human leukemia HL-60 cells", Cancer Letters 108 (1996), pp. 211-214.
La Rosee, Paul, et al., "Activity of the Bcr-Abl Kinase Inhibitor PD180970 against Clinically Relevant Bcr-Abl Isoforms That Cause Resistance to Imatinib Mesylate (Gleevec, STI571)", Cancer Res 62 (2002), pp. 7149-7153.
O'Hare, Thomas, et al., "In vitro Activity of Bcr-Abl Inhibitors AMN107 and BMS-354825 against Clinically Relevant Imatinib-Resistant Abl Kinase Domain Mutants", Cancer Res 65 (2005), pp. 4500-4505.
da Silva, Edson F., et al., "Synthesis and biological evaluation of new 1,3,4-thiadiazolium-2 phenylamine derivatives against *Leishmania amazonensis* promastigotes and amastigotes", European Journal of Medicinal Chemistry 37 (2002), pp. 979-984.
Tanaka, Ruriko, et al., "Abl tyrosine kinase inhibitors for overriding Bcr-Abl/T3141: from the second to third generation", Expert Reviews (2008), pp. 1387-1398.

(Continued)

Primary Examiner — Samantha Shterengarts
Assistant Examiner — Amanda L Aguirre
(74) Attorney, Agent, or Firm — Ladas & Parry LLP

(57) ABSTRACT

The present invention relates to oxadiazole compounds in all their stereoisomeric and tautomeric forms and mixtures thereof in all ratios; and their pharmaceutically acceptable salts, pharmaceutically acceptable solvates, pharmaceutically acceptable prodrugs and pharmaceutically acceptable polymorphs. The invention also relates to processes for the manufacture of the oxadiazole compounds and to pharmaceutical compositions containing them. The said compounds and their pharmaceutical compositions are useful in the treatment of cancer, particularly chronic myeloid leukemia (CML). The present invention further provides a method of treatment of cancer by administering a therapeutically effective amount of said compounds or their pharmaceutical compositions, to a mammal in need thereof.

16 Claims, 5 Drawing Sheets

(56) References Cited

OTHER PUBLICATIONS

Moller, Gigi M.O., et al., "Upregulation of the TGFβ signaling pathway by Bcr-Abl: Implications for haemopoietic cell growth and chronic myeloid leukaemia", FEBS Letters 581 (2007), pp. 1329-1334.

La Rosee, Paul, et al., "Phospho-CRKL monitoring for the assessment of BCR-ABL activity in imatinib-resistant chronic myeloid leukemia or Ph+ acute lymphoblastic leukemia patients treated with nilotinib", Haematologica 93(5) (2008), pp. 765-769.

Carling, Robert W., et al., "3-Nitro-3,4-dihydro-2(1H-quinolones, Excitatory Amino Acid Antagonists Acting at Glycine-Site NMDA and (RS)-α-Amino-3-hydroxy-5-methly-4-isoxazolepropionic Acid Receptors", J. Med. Chem. 36, (1993), pp. 3397-3408.

Contreras, Jean-Marie, et al., "Aminopyridazines as Acetylcholinesterase Inhibitors", J. Med. Chem. 42, (1999), pp. 730-741.

Hale, Jeffrey J., et al., "A rational Utilization of High-Throughput screening Affords Selective, Orally Bioavailable 1-Benzyl-3-crboxyazetidine Sphingosine-1-phosphate-1 Receptor Agonists", J. Med. Chem. 47 (2004), pp. 6662-6665.

Kuhr, T., et al., "A randomized study comparing interferon (IFNα) plus low-dose cytarabine and interferon plus hydroxyurea (HU) in early chronic-phase chronic myeloid leukemia (CML)", Leukemia Research 27 (2003), pp. 405-411.

Diaz-Blanco, E., et al., "Molecular signature of CD34+ hematopoietic stem and progenitor cells of patients with CML in chronic phase", Leukemia 21 (2007), pp. 495-504.

Jilani, Iman, et al., "An immunological method for the detection of BCR-ABL fusion protein and monitoring its activation", Leukemia Research 32 (2008), pp. 936,943.

Bakunov, Stanislav A., et al., "Modification of the Tiemann Rearrangement: One-Pot Synthesis of N, N-Disubstituted Cyanamides from Amidoximes", Synthesis, No. 8, (2000), pp. 1148-1159.

Pipik, Brenda, et al., "A Preferred Synthesis of 1,2,4-Oxadiazoles", Synthetic Communications, vol. 34, No. 10 (2004), pp. 1863-1870.

Solladie, Guy, et al., "Chiral Sulfoxides in Asymmetric Synthesis: Enantioselective Synthesis of (×)(5S,7R)-Tarchonanthuslactone", Tetrahedron Asymmetry, vol. 7, No. 8, (1996), pp. 2371-2379.

Oda, Tsukasa, et al., "Crkl Is the Major Tyrosine-phosphorylated Protein in Neutrophils from Patients with chronic Myelogenous Leukemia*", The Journal of Biological Chemistry, vol. 269, No. 37 (1994), pp. 22925-22928.

\* cited by examiner

Cell line- E255V
Time point- 48 h

STYRENYL 1,2,4-OXADIAZOLE COMPOUNDS

RELATED APPLICATION INFORMATION

This application is a 371 of International Application PCT/IB2011/050770 filed 24 Feb. 2011 entitled "Oxadiazole Compounds, Their Preparation And Use", which was published on 1 Sep. 2011, with International Publication Number WO 2011/104680 A1, and which claims priority from U.S. Patent Applications 61/307,974 filed 25 Feb. 2010, the content of which is incorporated herein by reference.

FIELD OF THE INVENTION

The present invention relates to oxadiazole compounds, to processes for their preparation, pharmaceutical compositions containing them, and their use in the treatment of cancer.

BACKGROUND OF THE INVENTION

Cancer is an uncontrolled growth and spread of cells that may affect almost any tissue of the body. Cancer can be defined as abnormal growth of tissues characterized by a loss of cellular differentiation. It is caused due to a deregulation of the signaling pathways involved in cell survival, cell proliferation and cell death.

Current treatments for cancer and related diseases have limited effectiveness and a number of side effects. Cancer therapy currently falls under the following categories including surgery, radiation therapy, chemotherapy, bone marrow transplantation, stem cell transplantation, hormonal therapy, immunotherapy, antiangiogenic therapy, targeted therapy, gene therapy and others.

In the treatment of cancer, chemical compounds are used to reduce, inhibit, or diminish the proliferation of tumor cells, and thereby assist in reducing the size of a tumor. These compounds, which exhibit antitumor activity, find use in the treatment of cancers.

Chronic myeloid leukemia (CML) is a type of cancer characterized by the clonal proliferation of malignant myeloid progenitor cells resulting in excessive number of myeloid cells in all stages of maturation. Development of CML is associated with a specific chromosomal translocation known as the Philadelphia (Ph) chromosome. A molecular consequence of this translocation is the generation of a fusion protein Bcr-Abl, a constitutively activated tyrosine kinase that is detectable throughout the course of the disease. The Ph chromosome produces an enzyme, a fusion protein (Bcr-Abl) that plays a central role in aberrant cell growth and division. This aberrant enzyme sends out signals through multiple pathways within the cell, resulting in the overproduction of white blood cells in the body. The result is that, while a healthy cubic millimeter of blood contains 4,000 to 10,000 white blood cells, blood from a patient with CML contains 10 to 25 times this amount. The massive increase in the number of white blood cells characterises CML. In addition to CML, acute lymphoid leukemia (ALL) and acute myeloid leukemia (AML) are Ph positive leukemias.

The median survival of patients after diagnosis with CML is 4-6 years, with a range of less than one year to more than 10 years (National Cancer Institute: Chronic Myeloid Leukemia: Treatment: Health Professional Version: General Information 2006). Treatment options for patients with CML are limited and are based on the stage of leukemia, and the patient's age and health. The disease may be treated with bone marrow transplant (BMT) therapy or with drug therapy. Interferon-alpha has been used for the treatment of CML and has shown improved survival in CML patients. However, there are reports of patients showing resistance to the treatment with Interferon-alpha (Leukemia Research, 2003, 27, 5, 405-411).

Recent reports have shown that ectopic Bcr-Abl expression dramatically increases TGFβ/Smad-dependent transcriptional activity in Cos1 cells, and that this may be due to enhancement of Smad promoter activity (FEBS Letters, 2007, 581, 7, 1329-1334; Leukemia, 2007, 21, 494-504). Bcr-Abl expressing TF-1 myeloid cells are more potently growth arrested by TGFβ compared to the parental TF-1 cell line. The expression of Bcr-Abl leads to hyper-responsiveness of myeloid cells to TGFβ, and that this novel cross-regulatory mechanism might play an important role in maintaining the transformed progenitor cell population in CML. A small pocket of haemopoietic stem cells, which are resistant to imatinib mesylate, in part because they are non-cycling, also hinders the complete eradication of CML. Therefore, TGFβ is a prime candidate for maintaining these CML stem cells in a non-cycling state. An upregulation or prolongation of TGFβ signaling by Bcr-Abl, suggests that one of the mechanisms by which Bcr-Abl promotes the transformation of haemopoietic progenitor cells, is by influencing the level of TGFβ signaling activity. TGFβ plays a vital role in the preservation of the malignant progenitor population, and is partially responsible for the resistance to treatments targeting Bcr-Abl that is observed in a proportion of CML patients.

CRKL protein [V-crk sarcoma virus CT10 oncogene homolog (avian)-like] belongs to the SH2-SH3 family of adaptor proteins. It is a 39-kD protein and is constitutively heavily phosphorylated in Philadelphia-chromosome positive CML cells. It is a prominent substrate for Bcr-Abl kinase. It is also stably phosphorylated in neutrophils from patients in chronic phase of CML at a point in maturation when the Bcr-Abl kinase activity is downregulated as measured by autophosphorylation. CRKL and Bcr-Abl form a complex suggesting a significant role for this adaptor protein in Bcr-Abl transformation. Phospho-CRKL monitoring has been recognized as a prognostic marker in CML patients treated with first and second generation Bcr-Abl inhibitors (Haematologica, 2008, 93, 5, 765-769; The Journal of Biological Chemistry, 1994, 269, 37, 16, 22925-22928).

Imatinib mesylate (Gleevec® or Glivec®; Novartis India Ltd.) is currently the most specific drug for the treatment of CML and is regarded as a very effective therapy. Imatinib mesylate inhibits the Bcr-Abl tyrosine kinase and the effectiveness of imatinib mesylate in CML patients is based on overall hematologic and cytogenetic response rates. Despite significant hematologic and cytogenetic responses, resistance to imatinib mesylate has also been observed in CML patients, particularly in patients who have progressed to either the accelerated or blastic phase of the disease. U.S. Pat. No. 7,521,175 describes possible mechanisms associated with imatinib mesylate resistance in CML patients and discloses a number of Bcr-Abl mutants associated with resistance to imatinib mesylate. Attempts have been made to find new therapeutic strategies to prevent or overcome this resistance.

Recently, two experimental drugs namely nilotinib (AMN-107; Novartis India Ltd.) and dasatinib (BMS-354825; Bristol Myers Squibb) were found to be effective in circumventing some but not all forms of imatinib mesylate resistance (Expert Reviews, Anticancer Ther., 2008, 8, 9, 1387-1398). The T315I mutant is one of the more predominant mutations seen in imatinib mesylate-resistant patients. This T315I mutation was shown to preserve kinase activity resulting in ineffective binding of imatinib mesylate to Bcr-Abl. Another drug, Homoharringtonine (ChemGenex Pharmaceuticals) which is in the Phase II/III stage has been found to be useful for patients with imatinib mesylate resistant CML, including those containing the T315I mutation (Expert Reviews, Anticancer Therapy, 2008, 8, 9, 1387-1398). However, despite these developments, there still exists a continuing need for agents which are effective against the imatinib mesylate-resistant CML.

Blood, 2003, 101, 690-698, describes the K-562-R resistant cell line. K-562 is one of the human leukemic cell lines which contains a wild type Bcr-Abl protein, while K-562-R is a K-562 cell line which is made resistant to imatinib mesylate by continuous exposure to imatinib mesylate (2 µg/mL).

Cancer Research, 2005, 65, 11, 4500-4505 describes various imatinib mesylate resistant cell lines-Ba/F3 Bcr-Abl/T315I, Ba/F3 Bcr-Abl/E255K, Ba/F3 Bcr-Abl/H396P, Ba/F3 Bcr-Abl/M351T, Ba/F3 Bcr-Abl/F359V, Ba/F3 Bcr-Abl/E255V, Ba/F3 Bcr-Abl/F317L, Ba/F3 Bcr-Abl/H396R, Ba/F3 Bcr-Abl/M244V, Ba/F3 Bcr-Abl/Q252H, Ba/F3 Bcr-Abl/Y253F and Ba/F3 Bcr-Abl/Y253H.

Cancer Letters, 1996, 108, 211-214, describes the inhibitory effect of caffeic acid phenethyl ester on human leukemia HL-60 cells.

PCT publication WO2008026125 describes the use of caffeic acid and its derivatives for the treatment of CML, which is resistant to treatment with imatinib mesylate.

There is an urgent need for medicaments for treating cancer, in particular chronic myeloid leukemia (CML) and more particularly, chronic myeloid leukemia that is resistant to treatment with imatinib mesylate due to Bcr-Abl mutation.

SUMMARY OF THE INVENTION

The present invention relates to oxadiazole compounds, processes for their preparation and their use in the treatment of cancer.

According to one aspect of the present invention, there are provided compounds of formula 1 (as provided herein below), stereoisomers and tautomers thereof, pharmaceutically acceptable salts, solvates, prodrugs and polymorphs thereof.

According to another aspect of the present invention, there are provided processes for producing compounds of formula 1.

According to yet another aspect of the present invention, there is provided the use of compounds of formula 1 in the treatment of cancer.

According to another aspect of the present invention, there is provided the use of compounds of formula 1 for the inhibition of TGFβ (Transforming Growth Factor-β).

According to a further aspect of the present invention, there is provided a method for the treatment of cancer, particularly CML (Chronic myeloid leukemia), the method including administering to a mammal in need thereof a therapeutically effective amount of a compound of formula 1.

According to another aspect of the present invention, there are provided pharmaceutical compositions including one or more compounds of formula 1 as active ingredient(s).

According to still another aspect of the present invention, there is provided use of compounds of formula 1 for the manufacture of medicaments, which are useful for the treatment of cancer.

DETAILED DESCRIPTION OF THE INVENTION

Figure 1:
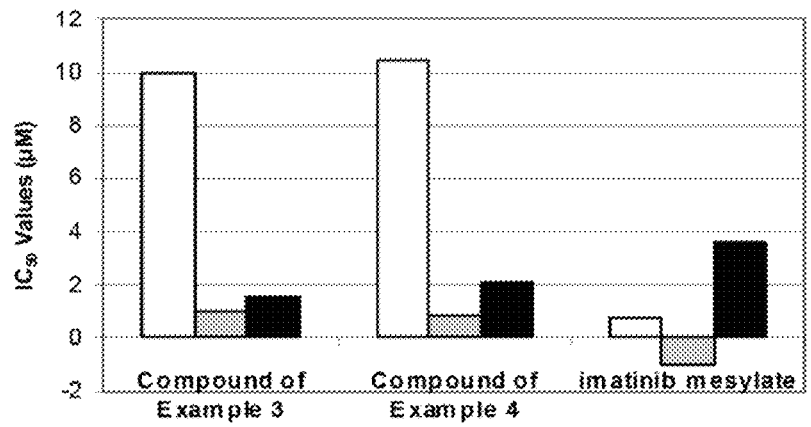
FIG. 1 shows inhibitory concentrations ($IC_{50}$) for compounds of the present invention in imatinib mesylate sensitive (Ba/F3 Bcr-Abl/Wild Type) and imatinib mesylate resistant (Ba/F3 Bcr-Abl/T315I) cell lines.

The present invention provides oxadiazole compounds of formula 1;

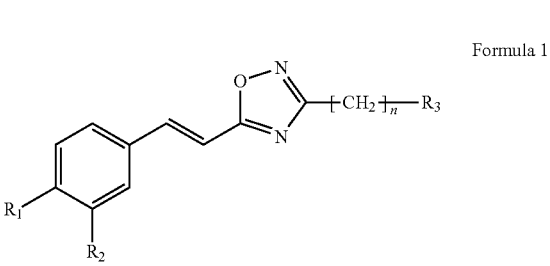

Formula 1 in all their stereoisomeric and tautomeric forms, their pharmaceutically acceptable salts, pharmaceutically acceptable solvates, pharmaceutically acceptable prodrugs and pharmaceutically acceptable polymorphs;

wherein, $R_1$ is selected from hydroxy, ($C_1$-$C_{12}$)-alkoxy or aryloxy;

$R_2$ is selected from hydroxy, nitro, ($C_1$-$C_{12}$)-alkoxy, aryloxy, NH—$SO_2$—($C_1$-$C_{12}$)-alkyl, NH—$SO_2$-aryl or $NR_aR_b$;

wherein $R_a$ and $R_b$ are independently selected from hydrogen, ($C_1$-$C_{12}$)-alkyl, aralkyl, aryl or heterocyclyl;

$R_3$ is selected from hydrogen, ($C_1$-$C_{12}$)-alkyl, ($C_3$-$C_{12}$)-cycloalkyl, aralkyl, aryl or heterocyclyl; and n is an integer from 0-3;

wherein, ($C_1$-$C_{12}$)-alkyl is unsubstituted or substituted with one or more groups selected from halogen, hydroxy, cyano, nitro, ($C_1$-$C_{12}$)-alkoxy, unsubstituted or substituted aryl, unsubstituted or substituted heterocyclyl, $COOR_a$, $C(O)R_a$, $SR_a$, $NR_aR_b$ and $C(O)NR_aR_b$;

alkyl of ($C_1$-$C_{12}$)-alkoxy is unsubstituted or substituted with one or more groups selected from halogen, hydroxy, cyano, nitro, unsubstituted or substituted aryl, unsubstituted or substituted heterocyclyl, $COOR_a$, $C(O)R_a$, $SR_a$, $NR_aR_b$ and $C(O)NR_aR_b$;

($C_3$-$C_{12}$)-cycloalkyl is unsubstituted or substituted with one or more groups selected from halogen, hydroxy, cyano, nitro, unsubstituted or substituted ($C_1$-$C_{12}$)-alkyl, ($C_1$-$C_{12}$)-alkoxy, unsubstituted or substituted aryl, unsubstituted or substituted heterocyclyl, COOR$_a$, C(O)R$_a$, SR$_a$, NR$_a$R$_b$ and C(O)NR$_a$R$_b$;

aryl is unsubstituted or substituted with one or more groups selected from halogen, hydroxy, cyano, nitro, ($C_1$-$C_{12}$)-alkyl, ($C_2$-$C_{12}$)-alkenyl, ($C_2$-$C_{12}$)-alkynyl, ($C_1$-$C_{12}$)-alkoxy, unsubstituted or substituted heterocyclyl, COOR$_a$, C(O)R$_a$, SR$_a$, NR$_a$R$_b$ and C(O)NR$_a$R$_b$;

aryl of aryloxy is unsubstituted or substituted with one or more groups selected from halogen, hydroxy, cyano, nitro, unsubstituted or substituted ($C_1$-$C_{12}$)-alkyl, ($C_2$-$C_{12}$)-alkenyl, ($C_2$-$C_{12}$)-alkynyl, unsubstituted or substituted heterocyclyl, COOR$_a$, C(O)R$_a$, SR$_a$, NR$_a$R$_b$ and C(O)NR$_a$R$_b$;

aryl of aralkyl is unsubstituted or substituted with one or more groups selected from halogen, hydroxy, cyano, nitro, unsubstituted or substituted ($C_1$-$C_{12}$)-alkyl, ($C_2$-$C_{12}$)-alkenyl, unsubstituted or substituted heterocyclyl and ($C_2$-$C_{12}$)-alkynyl;

heterocyclyl is unsubstituted or substituted with one or more groups selected from halogen, hydroxy, cyano, nitro, unsubstituted or substituted ($C_1$-$C_{12}$)-alkyl, ($C_1$-$C_{12}$)-alkoxy, unsubstituted or substituted aralkyl, unsubstituted or substituted aryl, COOR$_a$, C(O)R$_a$, SR$_a$, NR$_a$R$_b$, ($C_1$-$C_{12}$)-alkyl-NR$_a$R$_b$ and C(O)NR$_a$R$_b$; and R$_a$ and R$_b$ are independently selected from hydrogen, ($C_1$-$C_{12}$)-alkyl, aralkyl, aryl or heterocyclyl.

DEFINITIONS

As used herein, the term "alkyls" whether used alone or as part of a substituent group, refers to the radical of saturated aliphatic groups, including straight or branched-chain alkyl groups. An alkyl group can have a straight chain or branched chain containing 1 to 12 carbon atoms. Alkyl groups include methyl, ethyl, n-propyl, isopropyl, n-butyl, t-butyl, iso-butyl, sec-butyl, n-pentyl, isopentyl, 2-pentyl, 3-pentyl, neo-pentyl, n-hexyl, isohexyl, 2-hexyl, 3-hexyl, n-heptyl, n-octyl, n-nonyl and n-decyl.

A substituted alkyl refers to a ($C_1$-$C_{12}$)-alkyl substituted with one or more groups selected from halogen, hydroxy, cyano, nitro, unsubstituted or substituted ($C_1$-$C_{12}$)-alkoxy, unsubstituted or substituted aryl, unsubstituted or substituted heterocyclyl, COOR$_a$, C(O)R$_a$, SR$_a$, NR$_a$R$_b$ and C(O)NR$_a$R$_b$; wherein R$_a$ and R$_b$ are independently selected from hydrogen, unsubstituted or substituted ($C_1$-$C_{12}$) alkyl, unsubstituted or substituted aralkyl, unsubstituted or substituted aryl and unsubstituted or substituted heterocyclyl. Examples of substituted alkyls include benzyl, hydroxymethyl, hydroxyethyl, 2-hydroxyethyl, N-morpholinomethyl, N-indolomethyl, piperidinylmethyl, trifluoromethyl and aminoethyl.

As used herein, the term "alkenyl" whether used alone or as part of a substituent group, refers to a straight or branched chain hydrocarbon radical containing the indicated number of carbon atoms and at least one carbon-carbon double bond (two adjacent sp$^2$ carbon atoms). For example, ($C_2$-$C_{12}$)-alkenyl refers to an alkenyl group having 2 to 6 carbon atoms. Depending on the placement of double bond and substituents if any, the geometry of the double bond may be entgegen (E), or zusammen (Z), cis or trans. Examples of alkenyl include, but are not limited to, vinyl, allyl and 2-propenyl.

A substituted alkenyl refers to an alkenyl group substituted with one or more groups selected from halogen, hydroxy, cyano, nitro, unsubstituted or substituted ($C_1$-$C_{12}$)-alkoxy, unsubstituted or substituted aryl, unsubstituted or substituted heterocyclyl, COOR$_a$, C(O)R$_a$, SR$_a$, NR$_a$R$_b$ or C(O)NR$_a$R$_b$; wherein R$_a$ and R$_b$ are independently selected from hydrogen, unsubstituted or substituted ($C_1$-$C_{12}$) alkyl, unsubstituted or substituted aralkyl, unsubstituted or substituted aryl and unsubstituted or substituted heterocyclyl.

As used herein, the term "alkynyl" whether used alone or as part of a substituent group, refers to a straight or branched chain hydrocarbon radical containing the indicated number of carbon atoms and at least one carbon-carbon triple bond (two adjacent sp carbon atoms). For example, ($C_2$-$C_{12}$)-alkynyl refers to an alkynyl group having 2-12 carbon atoms. Examples of alkynyl include, but are not limited to, ethynyl, 1-propynyl, 3-propynyl and 3-butynyl.

A substituted alkynyl refers to an alkynyl group substituted with one or more groups selected from halogen, hydroxy, cyano, nitro, unsubstituted or substituted ($C_1$-$C_{12}$)-alkoxy, unsubstituted or substituted aryl, unsubstituted or substituted heterocyclyl, COOR$_a$, C(O)R$_a$, SR$_a$, NR$_a$R$_b$ or C(O)NR$_a$R$_b$; wherein R$_a$ and R$_b$ are independently selected from hydrogen, unsubstituted or substituted ($C_1$-$C_{12}$) alkyl, unsubstituted or substituted aralkyl, unsubstituted or substituted aryl and unsubstituted or substituted heterocyclyl.

As used herein, the term "alkoxyl" or "alkoxy" refers to a ($C_1$-$C_{12}$)-alkyl having an oxygen radical attached thereto. Representative alkoxy groups include methoxy, ethoxy, propoxy, isopropoxy, n-butoxy, isobutoxy and tert-butoxy.

A substituted alkoxy refers to an alkoxy group in which the alkyl is substituted with one or more groups selected from halogen, hydroxy, cyano, nitro, unsubstituted or substituted aryl, unsubstituted or substituted heterocyclyl, COOR$_a$, C(O)R$_a$, SR$_a$, NR$_a$R$_b$ or C(O)NR$_a$R$_b$; wherein R$_s$ and R$_b$ are independently selected from hydrogen, unsubstituted or substituted ($C_1$-$C_{12}$) alkyl, unsubstituted or substituted aralkyl, unsubstituted or substituted aryl or unsubstituted or substituted heterocyclyl. Examples of substituted alkoxy are chloromethoxy, 2-cyanoethoxy, trifluoromethoxy and benzyloxy group. A benzyloxy group refers to a benzyl having an oxygen radical attached thereto.

The term "($C_3$-$C_{12}$) cycloalkyl" or "cycloalkyl" refers to monocyclic or polycyclic hydrocarbon groups of 3-12 carbon atoms, which may be optionally bridged such as adamantyl. Examples of cycloalkyl include cyclopropyl, cyclobutyl, cyclopentyl, cyclohexyl, cycloheptyl, cyclooctyl and cyclononyl.

A substituted ($C_3$-$C_{12}$) cycloalkyl refers to a "($C_3$-$C_{12}$) cycloalkyl" substituted by one or more substituents such as halogen, hydroxy, cyano, nitro, unsubstituted or substituted ($C_1$-$C_{12}$)-alkyl, ($C_1$-$C_{12}$)-alkoxy, unsubstituted or substituted aryl, unsubstituted or substituted heterocyclyl, COOR$_a$, C(O)R$_a$, SR$_a$, NR$_a$R$_b$ or C(O)NR$_a$R$_b$; wherein R$_a$ and R$_b$ are independently selected from hydrogen, unsubstituted or substituted ($C_1$-$C_{12}$) alkyl, unsubstituted or substituted aralkyl, unsubstituted or substituted aryl and unsubstituted or substituted heterocyclyl.

The term "aryl" as used herein refers to monocyclic or polycyclic hydrocarbon groups having 6 to 14 ring carbon atoms in which the carbocyclic ring(s) present have a conjugated pi electron system. Examples of ($C_6$-$C_{14}$)-aryl residues are phenyl, naphthyl, fluorenyl or anthracenyl. Examples of ($C_6$-$C_{10}$)-aryl residues are phenyl or naphthyl. Aryl groups can be unsubstituted or substituted by one or more, for example 1, 2, 3, 4 or 5, identical or different substituents selected from halogen, hydroxy, cyano, nitro, unsubstituted or substituted ($C_1$-$C_{12}$) alkyl, unsubstituted or substituted ($C_2$-$C_{12}$)-alkenyl, unsubstituted or substituted ($C_2$-$C_{12}$)-alkynyl, unsubstituted or substituted ($C_1$-$C_{12}$)-alkoxy, unsubstituted or substituted heterocyclyl, COOR$_a$, C(O)R$_a$, SR$_a$, NR$_a$R$_b$ or C(O)NR$_a$R$_b$; wherein R$_a$ and R$_b$ are independently selected from hydrogen, unsubstituted or substituted ($C_1$-$C_{12}$) alkyl, unsubstituted or substituted aralkyl, unsubstituted or substituted aryl and unsubstituted or substituted heterocyclyl. In monosubstituted phenyl residues the substituent can be located in the 2-position, the 3-position or the 4-position. If the phenyl carries two substituents, they can be located in 2,3-position, 2,4-position, 2,5-position, 2,6-position, 3,4-position or 3,5-position. Examples of monosubstituted phenyl groups are 3-trifluoromethylphenyl, 4-chlorophenyl and 4-cyanophenyl. Examples of disubstituted phenyl groups are 3,5-difluorophenyl and 3,4-dimethoxyphenyl.

As used herein, the term "aryloxyl" or "aryloxy" refers to an aryl group having an oxygen radical attached thereto. The aryl of aryloxy group may be unsubstituted or substituted as explained in the definition of substituted aryl herein above. Representative aryloxy groups include phenoxy, 4-chlorophenoxy, 3,4-dimethoxy phenoxy, etc.

The term "aralkyl" refers to an aryl group bonded directly through an alkyl group, such as benzyl. The aryl of the aralkyl group may be unsubstituted or substituted as explained in the definition of substituted aryl herein above.

The term "heteroatom" as used herein includes nitrogen, oxygen, and sulfur. Any heteroatom with unsatisfied valency is assumed to have a hydrogen atom to satisfy the valency.

Heterocyclyl includes saturated heterocyclic ring systems, which do not contain any double bonds within the rings, as well as unsaturated heterocyclic ring systems, which contain one or more, for example, 3 double bonds within a ring, provided that the resulting mono, bi or tricyclic ring system is stable. In monocyclic heterocyclyl groups, heterocyclyl preferably is a 4-membered, 5-membered, 6-membered or 7-membered ring, more preferably a 5- or 6-membered ring. The heterocyclyl group may, for example, have 1 or 2 oxygen atoms and/or 1 or 2 sulfur atoms and/or 1 to 3 nitrogen atoms in the ring. Aromatic heterocyclyl groups may also be referred to by the customary term "heteroaryl" for which all the definitions and explanations relating to heterocyclyl apply. Examples of heterocyclyls include pyrrolyl, pyrrolidinyl, pyrazolyl, imidazolyl, pyrazinyl, piperazinyl, oxazolyl, isoxazolyl, thiazolyl, furyl, thienyl, pyridyl, pyrimidyl, piperidyl, benzothiazolyl, purinyl, benzimidazolyl, benzoxazolyl, indolyl, isoindolyl, isoquinolyl, isoquinolyl, morpholinyl, quinoxalinyl, and quinolyl.

A substituted heterocyclyl refers to a heterocyclyl substituted with one or more groups selected from halogen, hydroxy, cyano, nitro, unsubstituted or substituted ($C_1$-$C_{12}$)-alkyl, unsubstituted or substituted ($C_1$-$C_{12}$)-alkoxy, unsubstituted or substituted aralkyl, unsubstituted or substituted aryl, $COOR_a$, $C(O)R_a$, $SR_a$, $NR_aR_b$, ($C_1$-$C_{12}$)-alkyl-$NR_aR_b$ or $C(O)NR_aR_b$; wherein $R_a$ and $R_b$ are independently selected from hydrogen, unsubstituted or substituted ($C_1$-$C_{12}$) alkyl, unsubstituted or substituted aralkyl, unsubstituted or substituted aryl and unsubstituted or substituted heterocyclyl. The substituents may be present on either the ring carbon or the ring nitrogen atoms. The substituents can be present at one or more positions provided that a stable molecule results.

The term "halogen" refers to a fluorine, chlorine, bromine, or iodine atom.

The term "solvate" describes a complex wherein the compound is coordinated with a proportional amount of a solvent molecule. Specific solvates, wherein the solvent is water, are referred to as hydrates.

The term "tautomer" refers to the coexistence of two (or more) compounds that differ from each other only in the position of one (or more) mobile atoms and in electron distribution, for example, keto-enol tautomers.

It will be understood that "substitution" or "substituted with" includes the implicit proviso that such a substitution is in accordance with permitted valence state of the substituted atom and the substituent, and represents a stable compound, which does not readily undergo undesired transformation such as by rearrangement, cyclization, or elimination.

As used herein, the term "compound of formula 1" includes all the stereoisomeric and tautomeric forms and mixtures thereof in all ratios, and their pharmaceutically acceptable salts, solvates, prodrugs and polymorphs.

ASPECTS OF THE INVENTION

In one aspect, the present invention provides compounds of formula 1;

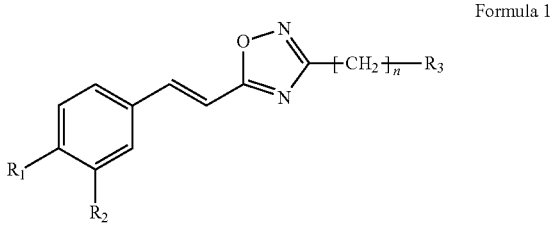

Formula 1 wherein,
$R_1$ is selected from hydroxy, ($C_1$-$C_{12}$)-alkoxy or aryloxy;
$R_2$ is selected from hydroxy, ($C_1$-$C_{12}$)-alkoxy or aryloxy;
$R_3$ is selected from hydrogen, ($C_1$-$C_{12}$)-alkyl, ($C_3$-$C_{12}$)-cycloalkyl, aralkyl, aryl or heterocyclyl; and
n is an integer from 0-3;
wherein,
($C_1$-$C_{12}$)-alkyl is unsubstituted or substituted with one or more groups selected from halogen, hydroxy, cyano, nitro, unsubstituted or substituted aryl and unsubstituted or substituted heterocyclyl;
alkyl of ($C_1$-$C_{12}$)-alkoxy is unsubstituted or substituted with one or more groups selected from halogen, hydroxy, cyano, nitro, unsubstituted or substituted aryl and unsubstituted or substituted heterocyclyl;
($C_3$-$C_{12}$)-cycloalkyl is unsubstituted or substituted with one or more groups selected from halogen, hydroxy, cyano, nitro, unsubstituted or substituted ($C_1$-$C_{12}$)-alkyl, unsubstituted or substituted aryl and unsubstituted or substituted heterocyclyl;
aryl is unsubstituted or substituted with one or more groups selected from halogen, hydroxy, cyano, nitro, unsubstituted or substituted ($C_1$-$C_{12}$)-alkyl, unsubstituted or substituted ($C_2$-$C_{12}$)-alkenyl, unsubstituted or substituted ($C_2$-$C_{12}$)-alkynyl and unsubstituted or substituted heterocyclyl;
aryl of aryloxy is unsubstituted or substituted with one or more groups selected from halogen, hydroxy, cyano, nitro, unsubstituted or substituted ($C_1$-$C_{12}$)-alkyl, unsubstituted or substituted ($C_2$-$C_{12}$)-alkenyl, unsubstituted or substituted ($C_2$-$C_{12}$)-alkynyl and unsubstituted or substituted heterocyclyl;
aryl of aralkyl is unsubstituted or substituted with one or more groups selected from halogen, hydroxy, cyano, nitro, unsubstituted or substituted ($C_1$-$C_{12}$)-alkyl, unsubstituted or substituted ($C_2$-$C_{12}$)-alkenyl, unsubstituted or substituted ($C_2$-$C_{12}$)-alkynyl and unsubstituted or substituted heterocyclyl;
heterocyclyl is unsubstituted or substituted with one or more groups selected from halogen, hydroxy, cyano, nitro, unsubstituted or substituted ($C_1$-$C_{12}$)-alkyl, ($C_1$-$C_{12}$)-alkoxy, unsubstituted or substituted aralkyl, unsubstituted or substituted aryl, $COOR_a$, $C(O)R_a$, $NR_aR_b$ and $(C_1-C_{12})$-alkyl-$NR_aR_b$; and $R_a$, and $R_b$ are independently selected from hydrogen, $(C_1-C_{12})$ alkyl, aralkyl, aryl or heterocyclyl.

In another aspect, the present invention provides compounds of formula 1;
wherein,
$R_1$ is hydroxy or $(C_1-C_{12})$-alkoxy;
$R_2$ is hydroxy or $(C_1-C_{12})$-alkoxy;
$R_3$ is hydrogen or $(C_1-C_{12})$-alkyl; and
n is 0 or 1;
wherein,
$(C_1-C_{12})$-alkyl is unsubstituted or substituted with one or more groups selected from halogen, hydroxy, cyano, nitro, unsubstituted or substituted aryl and unsubstituted or substituted heterocyclyl;
aryl is unsubstituted or substituted with one or more groups selected from halogen, hydroxy, cyano, nitro, unsubstituted or substituted $(C_1-C_{12})$-alkyl and unsubstituted or substituted heterocyclyl;
heterocyclyl is unsubstituted or substituted with one or more groups selected from halogen, hydroxy, cyano, nitro, unsubstituted or substituted $(C_1-C_{12})$-alkyl, unsubstituted or substituted aralkyl, unsubstituted or substituted aryl, $COOR_a$, $C(O)R_a$, $NR_aR_b$ and $(C_1-C_{12})$-alkyl-$NR_aR_b$; and
$R_a$ and $R_b$ are independently selected from hydrogen, $(C_1-C_{12})$ alkyl, aralkyl, aryl or heterocyclyl.

In yet another aspect, the present invention provides compounds of formula 1;
wherein,
$R_1$ is hydroxy or unsubstituted $(C_1-C_{12})$-alkoxy;
$R_2$ is hydroxy or unsubstituted $(C_1-C_{12})$-alkoxy;
$R_3$ is hydrogen or unsubstituted $(C_1-C_{12})$-alkyl; and
n is 0 or 1, In a further aspect, the present invention provides compounds of formula 1;
wherein,
$R_1$ is hydroxy or $(C_1-C_{12})$-alkoxy;
$R_2$ is hydroxy or $(C_1-C_{12})$-alkoxy;
$R_3$ is $(C_1-C_{12})$-alkyl; and
n is 0;
wherein,
$(C_1-C_{12})$-alkyl is selected from methyl, ethyl, n-propyl, iso-propyl, n-butyl, t-butyl, iso-butyl, sec-butyl, n-pentyl, isopentyl, 2-pentyl, 3-pentyl, neo-pentyl, n-hexyl, isohexyl, 2-hexyl, 3-hexyl, n-heptyl, n-octyl and n-nonyl.

In another aspect, the present invention provides compounds of formula 1;
wherein,
$R_1$ is hydroxy or $(C_1-C_{12})$-alkoxy;
$R_2$ is hydroxy or $(C_1-C_{12})$-alkoxy;
$R_3$ is $(C_3-C_{12})$-cycloalkyl; and
n is 0 or 1;
wherein,
alkyl of $(C_1-C_{12})$-alkoxy is unsubstituted or substituted with one or more groups selected from halogen, hydroxy, cyano, nitro, unsubstituted or substituted aryl and unsubstituted or substituted heterocyclyl;
$(C_3-C_{12})$-cycloalkyl is unsubstituted or substituted with one or more groups selected from halogen, hydroxy, cyano, nitro, unsubstituted or substituted $(C_1-C_{12})$-alkyl, unsubstituted or substituted aryl, unsubstituted or substituted heterocyclyl;
aryl is unsubstituted or substituted with one or more groups selected from halogen, is hydroxy, cyano, nitro, unsubstituted or substituted $(C_1-C_{12})$-alkyl and unsubstituted or substituted heterocyclyl;
aryl of aralkyl is unsubstituted or substituted with one or more groups selected from halogen, hydroxy, cyano, nitro, unsubstituted or substituted $(C_1-C_{12})$-alkyl, unsubstituted or substituted $(C_2-C_{12})$-alkenyl, unsubstituted or substituted $(C_2-C_{12})$-alkynyl and unsubstituted or substituted heterocyclyl;
heterocyclyl is unsubstituted or substituted with one or more groups selected from halogen, hydroxy, cyano, nitro, unsubstituted or substituted $(C_1-C_{12})$-alkyl, unsubstituted or substituted aralkyl, unsubstituted or substituted aryl, $COOR_a$, $C(O)R_a$, $NR_aR_b$ and $(C_1-C_{12})$-alkyl-$NR_aR_b$; and
$R_a$, and $R_b$ are independently selected from hydrogen, $(C_1-C_{12})$ alkyl, aralkyl, aryl or heterocyclyl.

In yet another aspect, the present invention provides compounds of formula 1;
wherein,
$R_1$ is hydroxy or unsubstituted $(C_1-C_{12})$-alkoxy;
$R_2$ is hydroxy or unsubstituted $(C_1-C_{12})$-alkoxy;
$R_3$ is unsubstituted $(C_3-C_{12})$-cycloalkyl; and
n is 0 or 1.

In another aspect, the present invention provides compounds of formula 1;
wherein,
$R_1$ is hydroxy or $(C_1-C_{12})$-alkoxy;
$R_2$ is hydroxy or $(C_1-C_{12})$-alkoxy;
$R_3$ is aryl; and
n is 0 or 1;
wherein,
$(C_1-C_{12})$-alkyl is unsubstituted or substituted with one or more groups selected from halogen, hydroxy, cyano, nitro, unsubstituted or substituted aryl and unsubstituted or substituted heterocyclyl;
alkyl of $(C_1-C_{12})$-alkoxy is unsubstituted or substituted with one or more groups selected from halogen, hydroxy, cyano, nitro, unsubstituted or substituted aryl and unsubstituted or substituted heterocyclyl;
aryl is unsubstituted or substituted with one or more groups selected from halogen, hydroxy, cyano, nitro, unsubstituted or substituted $(C_1-C_{12})$-alkyl and unsubstituted or substituted heterocyclyl;
aryl of aralkyl is unsubstituted or substituted with one or more groups selected from halogen, hydroxy, cyano, nitro, unsubstituted or substituted $(C_1-C_{12})$-alkyl, unsubstituted or substituted $(C_2-C_{12})$-alkenyl, unsubstituted or substituted $(C_2-C_{12})$-alkynyl and unsubstituted or substituted heterocyclyl;
heterocyclyl is unsubstituted or substituted with one or more groups selected from halogen, hydroxy, cyano, nitro, unsubstituted or substituted $(C_1-C_{12})$-alkyl, unsubstituted or substituted aralkyl, unsubstituted or substituted aryl, $COOR_a$, $C(O)R_a$, $NR_aR_b$ and $(C_1-C_{12})$-alkyl-$NR_aR_b$; and
$R_a$ and $R_b$ are independently selected from hydrogen, $(C_1-C_{12})$ alkyl, aralkyl, aryl or heterocyclyl.

In yet another aspect, the present invention provides compounds of formula 1;
wherein,
$R_1$ is hydroxy or unsubstituted $(C_1-C_{12})$-alkoxy;
$R_2$ is hydroxy or unsubstituted $(C_1-C_{12})$-alkoxy;
$R_3$ is phenyl; and
n is 1.

In a further aspect, the present invention provides compounds of formula 1;
wherein,
$R_1$ is hydroxy or $(C_1-C_{12})$-alkoxy;
$R_2$ is hydroxy or $(C_1-C_{12})$-alkoxy;
$R_3$ is heterocyclyl; and
n is 0 or 1;

wherein, $(C_1-C_{12})$-alkyl is unsubstituted or substituted with one or more groups selected from halogen, hydroxy, cyano, nitro, unsubstituted or substituted aryl and unsubstituted or substituted heterocyclyl;

alkyl of $(C_1-C_{12})$-alkoxy is unsubstituted or substituted with one or more groups selected from halogen, hydroxy, cyano, nitro, unsubstituted or substituted aryl and unsubstituted or substituted heterocyclyl;

aryl is unsubstituted or substituted with one or more groups selected from halogen, hydroxy, cyano, nitro, unsubstituted or substituted $(C_1-C_{12})$-alkyl and unsubstituted or substituted heterocyclyl;

aryl of aralkyl is unsubstituted or substituted with one or more groups selected from halogen, hydroxy, cyano, nitro, unsubstituted or substituted $(C_1-C_{12})$-alkyl, unsubstituted or substituted $(C_2-C_{12})$-alkenyl, unsubstituted or substituted $(C_2-C_{12})$-alkynyl and unsubstituted or substituted heterocyclyl;

heterocyclyl is unsubstituted or substituted with one or more groups selected from halogen, hydroxy, cyano, nitro, unsubstituted or substituted $(C_1-C_{12})$-alkyl, unsubstituted or substituted aralkyl, unsubstituted or substituted aryl, $COOR_a$, $C(O)R_a$, $NR_aR_b$ and $(C_1-C_{12})$-alkyl-$NR_aR_b$; and $R_a$ and $R_b$ are independently selected from hydrogen, $(C_1-C_{12})$ alkyl, aralkyl, aryl or heterocyclyl.

In another aspect, the present invention provides compounds of formula 1;
wherein,
$R_1$ is hydroxy or unsubstituted $(C_1-C_{12})$-alkoxy;
$R_2$ is hydroxy or unsubstituted $(C_1-C_{12})$-alkoxy;
$R_3$ is heterocyclyl; and
n is 1;
wherein,
heterocyclyl is unsubstituted or substituted with one or more groups selected from halogen, $(C_1-C_{12})$-alkyl, unsubstituted or substituted aralkyl, $COOR_a$, $NR_aR_b$ and $(C_1-C_{12})$-alkyl-$NR_aR_b$; and
$R_a$ and $R_b$ are independently selected from hydrogen, $(C_1-C_{12})$ alkyl, aralkyl, aryl or heterocyclyl.

In yet another aspect, the present invention provides compounds of formula 1;
wherein,
$R_1$ is hydroxy or unsubstituted $(C_1-C_{12})$-alkoxy;
$R_2$ is hydroxy or unsubstituted $(C_1-C_{12})$-alkoxy;
$R_3$ is piperidine or pyridine; and
n is 0 or 1;
wherein,
piperidine is unsubstituted or substituted with one or more groups selected from halogen, $(C_1-C_{12})$-alkyl, unsubstituted or substituted aralkyl, $COOR_a$, $NR_aR_b$ and $(C_1-C_{12})$-alkyl-$NR_aR_b$; and
$R_a$ and $R_b$ are independently selected from hydrogen, $(C_1-C_{12})$ alkyl, aralkyl, aryl or heterocyclyl.

In a further aspect, the present invention provides compounds of formula 1;
wherein,
$R_1$ is hydroxy or $(C_1-C_{12})$-alkoxy;
$R_2$ is selected from nitro, $NH-SO_2-(C_1-C_{12})$-alkyl, $NH-SO_2$-aryl or $NR_aR_b$; wherein $R_a$ and $R_b$ are independently selected from hydrogen, $(C_1-C_{12})$-alkyl, aralkyl, aryl or heterocyclyl;
$R_3$ is selected from hydrogen, $(C_1-C_{12})$-alkyl, $(C_3-C_{12})$-cycloalkyl, aralkyl, aryl or heterocyclyl; and
n is an integer from 0-3;

wherein,
$(C_1-C_{12})$-alkyl is unsubstituted or substituted with one or more groups selected from halogen, hydroxy, cyano, nitro, unsubstituted or substituted aryl and unsubstituted or substituted heterocyclyl;

alkyl of $(C_1-C_{12})$-alkoxy is unsubstituted or substituted with one or more groups selected from halogen, hydroxy, cyano, nitro, unsubstituted or substituted aryl and unsubstituted or substituted heterocyclyl;

$(C_3-C_{12})$-cycloalkyl is unsubstituted or substituted with one or more groups selected from halogen, hydroxy, cyano, nitro, unsubstituted or substituted $(C_1-C_{12})$-alkyl, $(C_1-C_{12})$-alkoxy, unsubstituted or substituted aryl, unsubstituted or substituted heterocyclyl, $COOR_a$, $C(O)R_a$, $SR_a$, $NR_aR_b$ and $C(O)NR_aR_b$;

aryl is unsubstituted or substituted with one or more groups selected from halogen, hydroxy, cyano, nitro, unsubstituted or substituted $(C_1-C_{12})$-alkyl and unsubstituted or to substituted heterocyclyl;

aryl of aralkyl is unsubstituted or substituted with one or more groups selected from halogen, hydroxy, cyano, nitro, unsubstituted or substituted $(C_1-C_{12})$-alkyl, unsubstituted or substituted $(C_2-C_{12})$-alkenyl, unsubstituted or substituted $(C_2-C_{12})$-alkynyl and unsubstituted or substituted heterocyclyl;

heterocyclyl is unsubstituted or substituted with one or more groups selected from halogen, hydroxy, cyano, nitro, unsubstituted or substituted $(C_1-C_{12})$-alkyl, unsubstituted or substituted aralkyl, unsubstituted or substituted aryl, $COOR_a$, $C(O)R_a$, $NR_aR_b$ and $(C_1-C_{12})$-alkyl-$NR_aR_b$; and $R_a$ and $R_b$ are independently selected from hydrogen, $(C_1-C_{12})$ alkyl, aralkyl, aryl or heterocyclyl.

In another aspect, the present invention provides compounds of formula 1;
wherein,
$R_1$ is hydroxy or $(C_1-C_{12})$-alkoxy:
$R_2$ is selected from nitro, $NH_2$, $NH-SO_2-(C_1-C_{12})$-alkyl, $NH-SO_2$-aryl or $NR_aR_b$;
wherein $R_a$ and $R_b$ are independently selected from hydrogen, $(C_1-C_{12})$-alkyl, aralkyl, aryl or heterocyclyl;
$R_3$ is hydrogen or $(C_1-C_{12})$-alkyl; and
n is 0 or 1;
wherein,
$(C_1-C_{12})$-alkyl is unsubstituted or substituted with one or more groups selected from halogen, hydroxy, cyano, nitro, unsubstituted or substituted aryl and unsubstituted or substituted heterocyclyl;

alkyl of $(C_1-C_{12})$-alkoxy is unsubstituted or substituted with one or more groups selected from halogen, hydroxy, cyano, nitro, unsubstituted or substituted aryl and unsubstituted or substituted heterocyclyl;

aryl is unsubstituted or substituted with one or more groups selected from halogen, hydroxy, cyano, nitro, unsubstituted or substituted $(C_1-C_{12})$-alkyl and unsubstituted or substituted heterocyclyl;

aryl of aralkyl is unsubstituted or substituted with one or more groups selected from halogen, hydroxy, cyano, nitro, unsubstituted or substituted $(C_1-C_{12})$-alkyl, unsubstituted or substituted $(C_2-C_{12})$-alkenyl, unsubstituted or substituted $(C_2-C_{12})$-alkynyl and unsubstituted or substituted heterocyclyl;

heterocyclyl is unsubstituted or substituted with one or more groups selected from halogen, hydroxy, cyano, nitro, unsubstituted or substituted $(C_1-C_{12})$-alkyl, unsubstituted or substituted aralkyl, unsubstituted or substituted aryl, $COOR_a$, $C(O)R_a$, $NR_aR_b$ and $(C_1-C_{12})$-alkyl-$NR_aR_b$; and $R_a$ and $R_b$ are independently selected from hydrogen, $(C_1-C_{12})$ alkyl, aralkyl, aryl or heterocyclyl.

In yet another aspect, the present invention provides compounds of formula 1;
wherein,
$R_1$ is hydroxy or unsubstituted $(C_1-C_{12})$-alkoxy;
$R_2$ is selected from nitro, $NH_2$, $NH-SO_2-(C_1-C_{12})$-alkyl, $NH-SO_2$-aryl or $NR_aR_b$;
wherein $R_a$ and $R_b$ are independently selected from hydrogen, $(C_1-C_{12})$-alkyl, aralkyl, aryl or heterocyclyl;
$R_3$ is hydrogen or unsubstituted $(C_1-C_{12})$-alkyl; and
n is 0 or 1.

In a further aspect, the present invention provides compounds of formula 1;
wherein,
$R_1$ is hydroxy or $(C_1-C_{12})$-alkoxy;
$R_2$ is selected from nitro, $NH_2$, $NH-SO_2-(C_1-C_{12})$-alkyl, $NH-SO_2$-aryl or $NR_aR_b$;
wherein $R_a$ and $R_b$ are independently selected from hydrogen, $(C_1-C_{12})$-alkyl, aralkyl, aryl or heterocyclyl;
$R_3$ is aryl; and
n is 0 or 1;
wherein,
$(C_1-C_{12})$-alkyl is unsubstituted or substituted with one or more groups selected from halogen, hydroxy, cyano, nitro, unsubstituted or substituted aryl and unsubstituted or substituted heterocyclyl;
alkyl of $(C_1-C_{12})$-alkoxy is unsubstituted or substituted with one or more groups selected from halogen, hydroxy, cyano, nitro, unsubstituted or substituted aryl and unsubstituted or substituted heterocyclyl;
aryl is unsubstituted or substituted with one or more groups selected from halogen, hydroxy, cyano, nitro, unsubstituted or substituted $(C_1-C_{12})$-alkyl and unsubstituted or substituted heterocyclyl;
aryl of aralkyl is unsubstituted or substituted with one or more groups selected from halogen, hydroxy, cyano, nitro, unsubstituted or substituted $(C_1-C_{12})$-alkyl, unsubstituted or substituted $(C_2-C_{12})$-alkenyl, unsubstituted or substituted $(C_2-C_{12})$-alkynyl and unsubstituted or substituted heterocyclyl;
heterocyclyl is unsubstituted or substituted with one or more groups selected from halogen, hydroxy, cyano, nitro, unsubstituted or substituted $(C_1-C_{12})$-alkyl, unsubstituted or substituted aralkyl, unsubstituted or substituted aryl, $COOR_a$, $C(O)R_a$, $NR_aR_b$ and $(C_1-C_{12})$-alkyl-$NR_aR_b$; and
$R_a$ and $R_b$ are independently selected from hydrogen, $(C_1-C_{12})$ alkyl, aralkyl, aryl or heterocyclyl.

In another aspect, the present invention provides compounds of formula 1;
wherein,
$R_1$ is hydroxy or $(C_1-C_{12})$-alkoxy;
$R_2$ is selected from nitro, $NH_2$, $NH-SO_2-(C_1-C_{12})$-alkyl, $NH-SO_2$-aryl or $NR_aR_b$;
wherein $R_a$ and $R_b$ are independently selected from hydrogen, $(C_1-C_{12})$-alkyl, aralkyl, aryl, heterocyclyl, $SO_2$-alkyl or $SO_2$-aryl;
$R_3$ is heterocyclyl; and
n is 0 or 1;
wherein,
$(C_1-C_{12})$-alkyl is unsubstituted or substituted with one or more groups selected from halogen, hydroxy, cyano, nitro, unsubstituted or substituted aryl and unsubstituted or substituted heterocyclyl;
alkyl of $(C_1-C_{12})$-alkoxy is unsubstituted or substituted with one or more groups selected from halogen, hydroxy, cyano, nitro, unsubstituted or substituted aryl and unsubstituted or substituted heterocyclyl;
aryl is unsubstituted or substituted with one or more groups selected from halogen, hydroxy, cyano, nitro, unsubstituted or substituted $(C_1-C_{12})$-alkyl and unsubstituted or substituted heterocyclyl;
aryl of aralkyl is unsubstituted or substituted with one or more groups selected from halogen, hydroxy, cyano, nitro, unsubstituted or substituted $(C_1-C_{12})$-alkyl, unsubstituted or substituted $(C_2-C_{12})$-alkenyl, unsubstituted or substituted $(C_2-C_{12})$-alkynyl and unsubstituted or substituted heterocyclyl;
heterocyclyl is unsubstituted or substituted with one or more groups selected from halogen, hydroxy, cyano, nitro, unsubstituted or substituted $(C_1-C_{12})$-alkyl, unsubstituted or substituted aralkyl, unsubstituted or substituted aryl, $COOR_a$, $C(O)R_a$, $NR_aR_b$ and $(C_1-C_{12})$-alkyl-$NR_aR_b$; and
$R_a$ and $R_b$ are independently selected from hydrogen, $(C_1-C_{12})$ alkyl, aralkyl, aryl or heterocyclyl.

Examples of compounds according to the present invention are listed below:

4-[2-(3-Methyl-[1,2,4]oxadiazol-5-yl)-vinyl]-benzene-1,2-diol;
5-[2-(3,4-Dimethoxy-phenyl)-vinyl]-3-ethyl-[1,2,4]oxadiazole;
4-[2-(3-Ethyl-[1,2,4]oxadiazol-5-yl)-vinyl]-benzene-1,2-diol;
5-[2-(3,4-Dimethoxy-phenyl)-vinyl]-3-propyl-[1,2,4]oxadiazole;
4-[2-(3-Propyl-[1,2,4]oxadiazol-5-yl)-vinyl]-benzene-1,2-diol;
3-Benzyl-5-[2-(3,4-dimethoxy-phenyl)-vinyl]-[1,2,4]oxadiazole;
4-[2-(3-Benzyl-[1,2,4]oxadiazol-5-yl)-vinyl]-benzene-1,2-diol;
5-[2-(4-Methoxy-3-nitro-phenyl)-vinyl]-3-propyl-[1,2,4]oxadiazole;
2-Methoxy-5-[2-(3-propyl-[1,2,4]oxadiazol-5-yl)-vinyl]-phenylamine;
N-{2-Methoxy-5-[2-(3-propyl-[1,2,4]oxadiazol-5-yl)-vinyl]phenyl}-methanesulfonamide;
N-{2-Hydroxy-5-[2-(3-propyl-[1,2,4]oxadiazol-5-yl)-vinyl]-phenyl}-methanesulfonamide;
2-Nitro-4-[2-(5-propyl-[1,2,4]oxadiazol-3-yl)-vinyl]-phenol;
3-[2-(4-Methoxy-3-nitro-phenyl)-vinyl]-5-propyl-[1,2,4]oxadiazole;
2-Amino-4-[2-(5-propyl-[1,2,4]oxadiazol-3-yl)-vinyl]-phenol;
4-{5-[2-(3,4-Dimethoxy-phenyl)-vinyl]-[1,2,4]oxadiazol-3-ylmethyl}-piperidine-1-carboxylic acid tert-butyl ester;
4-{5-[2-(3,4-Dimethoxy-phenyl)-vinyl]-[1,2,4]oxadiazol-3-ylmethyl}-piperidine;
4-[2-(3-Piperidin-4-ylmethyl-[1,2,4]oxadiazol-5-yl)-vinyl]-benzene-1,2-diol;
4-{5-[2-(3,4-Dimethoxy-phenyl)-vinyl]-[1,2,4]oxadiazol-3-ylmethyl}-1-isopropyl-piperidine;
4-{2-[3-(1-Isopropyl-piperidin-4-ylmethyl)-[1,2,4]oxadiazol-5-yl]-vinyl}-benzene-1,2-diol;
[2-(4-{5-[2-(3,4-Dimethoxy-phenyl)-vinyl]-[1,2,4]oxadiazol-3-ylmethyl}-piperidin-1-yl)-ethyl]-dimethyl-amine;
4-(2-{3-[1-(2-Dimethylamino-ethyl)-piperidin-4-ylmethyl]-[1,2,4]oxadiazol-5-yl}-vinyl)-benzene-1,2-diol;
1-Benzyl-4-{5-[2-(3,4-dimethoxy-phenyl)-vinyl]-[1,2,4]oxadiazol-3-ylmethyl}-piperidine;
4-{2-[3-(1-Benzyl-piperidin-4-ylmethyl)-[1,2,4]oxadiazol-5-yl]-vinyl}benzene-1,2-diol;
5-[2-(3,4-Dimethoxy-phenyl)-vinyl]-3-nonyl-[1,2,4]oxadiazole;

4-[2-(3-Nonyl-[1,2,4]oxadiazol-5-yl)vinyl]-benzene-1,2-diol;

3-Cyclopropyl-5-[2-(3,4-dimethoxy-phenyl)-vinyl]-[1,2,4]oxadiazole;

4-[2-(3-Cyclopropyl-[1,2,4]oxadiazol-5-yl)-vinyl]-benzene-1,2-diol;

5-[2-(3,4-Dimethoxy-phenyl)-vinyl]-3-pentyl-[1,2,4]oxadiazole;

4-[2-(3-Pentyl-[1,2,4]oxadiazol-5-yl)-vinyl]-benzene-1,2-diol;

5-[2-(3,4-Dimethoxy-phenyl)-vinyl]-3-hexyl-[1,2,4]oxadiazole;

4-[2-(3-Hexyl-[1,2,4]oxadiazol-vinyl]-benzyldiol;

3-Cyclohexylmethyl-5-[2-(3,4-dimethoxy-phenyl)-vinyl]-[1,2,4]oxadiazole;

4-[2-(3-Cyclohexylmethyl-[1,2,4]oxadiazol-5-yl)-vinyl]-benzene-1,2-diol;

5-[2-(3,4-Dimethoxy-phenyl)-vinyl]-3-octyl-[1,2,4]oxadiazole;

4-[2-(3-Octyl-[1,2,4]oxadiazol-5-yl)-vinyl]-benzene-1,2-diol;

5-[2-(3,4-Dimethoxy-phenyl)-vinyl]-3-heptyl-[1,2,4]oxadiazole;

4-[2-(3-Heptyl-[1,2,4]oxadiazol-5-yl)-vinyl]-benzene-1,2-diol;

3-{5-[2-(3,4-Dimethoxy-phenyl)-vinyl]-[1,2,4]oxadiazol-3-yl}-pyridine;

4-[2-(3-Pyridin-3-yl-[1,2,4]oxadiazol-5-yl)-vinyl]-benzene-1,2-diol;

3-Cycloheptyl-5-[2-(3,4-dimethoxy-phenyl)-vinyl]-[1,2,4]oxadiazole;

4-[2-(3-Cycloheptyl-[1,2,4]oxadiazol-5-yl)-vinyl]-benzene-1,2-diol;

3-Cyclohexyl-5-[2-(3,4-dimethoxy-phenyl)-vinyl]-[1,2,4]oxadiazole; and

4-[2-(3-Cyclohexyl-[1,2,4]oxadiazol-5-yl)-vinyl]-benzene-1,2-diol;

or a stereoisomer, tautomer, pharmaceutically acceptable salt, pharmaceutically acceptable solvate, pharmaceutically acceptable prodrug or pharmaceutically acceptable polymorph thereof.

In another aspect, the invention encompasses compounds:

4-[2-(3-Methyl-[1,2,4]oxadiazol-5-yl)-vinyl]benzene-1,2-diol;

4-[2-(3-Ethyl-[1,2,4]oxadiazol-5-yl)-vinyl]-benzene-1,2-diol;

4-[2-(3-Propyl-[1,2,4]oxadiazol-5-yl)-vinyl]-benzene-1,2-diol;

4-[2-(3-Benzyl-[1,2,4]oxadiazol-5-yl)-vinyl]-benzene-1,2-diol;

N-{2-Hydroxy-5-[2-(3-propyl-[1,2,4]oxadiazol-5-yl)-vinyl]-phenyl}-methanesulfonamide;

2-Nitro-4-[2-(5-propyl-[1,2,4]oxadiazol-3-yl)-vinyl]-phenol;

2-Amino-4-[2-(5-propyl-[1,2,4-]oxadiazol-3-yl)-vinyl]-phenol;

4-[2-(3-Piperidin-4-ylmethyl-[1,2,4]oxadiazol-5-yl)-vinyl]-benzene-1,2-diol;

4-{2-[3-(1-Isopropyl-piperidin-4-ylmethyl)-[1,2,4]oxadiazol-5-yl]-vinyl}-benzene-1,2-diol;

4-(2-{3-[1-(2-Dimethylamino-ethyl)-piperidin-4-ylmethyl]-[1,2,4]oxadiazol-5-yl}-vinyl)-benzene-1,2-diol;

4-{2-[3-(1-Benzyl-piperidin-4-ylmethyl)-[1,2,4]oxadiazol-5-yl]-vinyl}-benzene-1,2-diol;

4-[2-(3-Nonyl-[1,2,4]oxadiazol-5-yl)-vinyl]-benzene-1,2-diol;

4-[2-(3-Cyclopropyl-[1,2,4]oxadiazol-5-yl)-vinyl]-benzene-1,2-diol;

4-[2-(3-Pentyl-[1,2,4]oxadiazol-5-yl)-vinyl]-benzene-1,2-diol;

4-[2-(3-Hexyl-[1,2,4]oxadiazol-vinyl]-benzyldiol;

4-[2-(3-Cyclohexylmethyl-[1,2,4]oxadiazol-5-yl)-vinyl]-benzene-1,2-diol,

4-[2-(3-Octyl-[1,2,4]oxadiazol-5-yl)-vinyl]-benzene-1,2-diol;

4-[2-(3-Heptyl-[1,2,4]oxadiazol-5-yl)-vinyl]-benzene-1,2-diol;

4-[2-(3-Pyridin-3-yl-[1,2,4]oxadiazol-5-yl)-vinyl]benzene-1,2-diol;

4-[2-(3-Cycloheptyl-[1,2,4]oxadiazol-5-yl)-vinyl]-benzene-1,2-diol; and

4-[2-(3-Cyclohexyl-[1,2,4]oxadiazol-5-yl)-vinyl]-benzene-1,2-diol;

or a stereoisomer, tautomer, pharmaceutically acceptable salt, pharmaceutically acceptable solvate, pharmaceutically acceptable prodrug or pharmaceutically acceptable polymorph thereof.

The compounds of the present invention also include all stereoisomeric and tautomeric forms and mixtures thereof in all ratios and their pharmaceutically acceptable salts, solvates, prodrugs and polymorphs.

According to another aspect of present invention, the compound of formula 1 can be prepared in a number of ways including using methods well known to the person skilled in the art. Examples of methods to prepare the present compounds are described below and illustrated in Schemes 1 to 7 but are not limited thereto. It will be appreciated by persons skilled in the art that within certain of the processes described herein, the order of the synthetic steps employed may be varied and will depend inter alia on factors such as the nature of functional groups present in a particular substrate and the protecting group strategy (if any) to be adopted. Clearly, such factors will also influence the choice of reagent to be used in the synthetic steps.

The reagents, reactants and intermediates used in the following processes are either commercially available or can be prepared according to standard literature procedures known in the art. The starting compounds and the intermediates used for the synthesis of compounds of the present invention, are referred to numerically (2-31).

Throughout the process description, the corresponding substituent groups in the various formulae representing starting compounds and intermediates have the same meanings as that for the compound of formula 1 unless stated otherwise. The schemes of the present invention are referred to numerically (1-7). The processes used in various schemes of the present invention, are referred to with general symbols namely 1a, 1b, 1c, 1d, 2a, 2b, 2c, 2d, 3a, 3b, 3c, 4a, 4b, 4c, 4d, 4e, 4f, 4g, 5a, 5b, 6a, 6b, 6c, 6d, 6e, 7a, 7b and 7c.

Processes for the preparation of compounds of the present invention are set forth in the following schemes:

Scheme 1:

Scheme 1 depicts a process for the preparation of the compounds of formula 1 (referred in Scheme 1 as compound 6 ($R_1=R_2=(C_1-C_{12})$-alkoxy) and compound 7 ($R_1=R_2=OH$) wherein n and $R_3$ are as defined in formula 1). Said process includes steps 1 to 5 as described below:

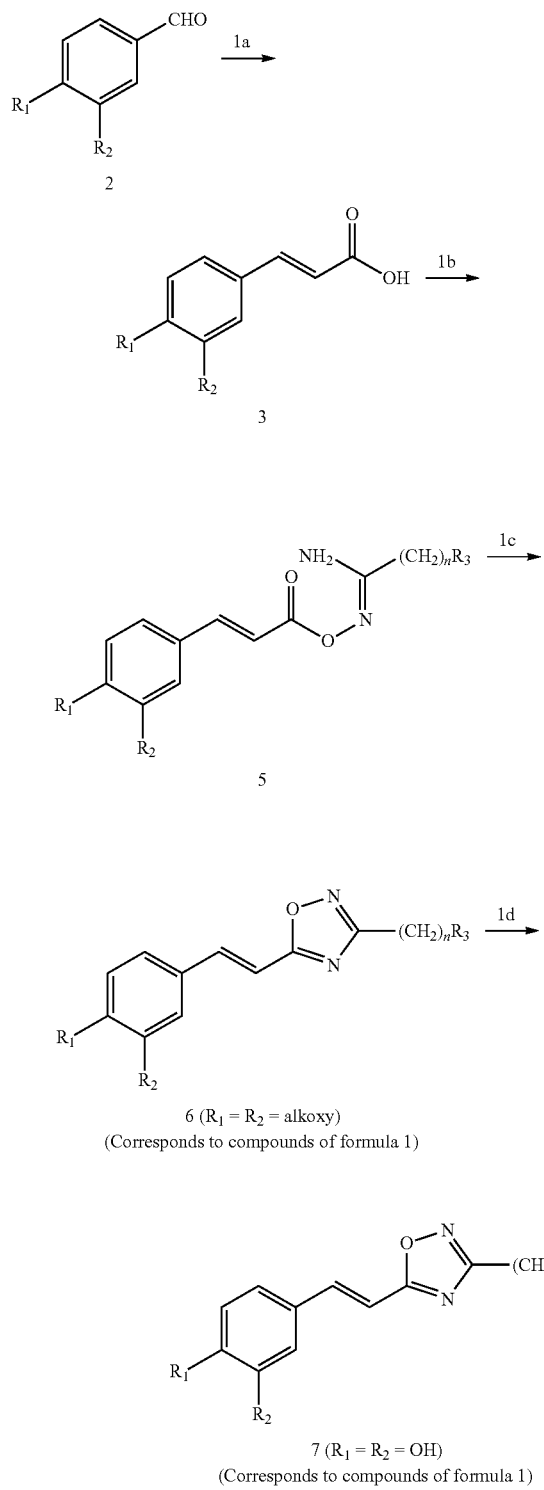

6 ($R_1 = R_2$ = alkoxy)
(Corresponds to compounds of formula 1)

7 ($R_1 = R_2$ = OH)
(Corresponds to compounds of formula 1)

Step 1
Preparation of Compound of Formula 3:

Compound of formula 2 (wherein $R_1$ and $R_2$ are $(C_1-C_{12})$-alkoxy) can be subjected to Knoevenagel condensation with malonic acid (European Journal of Medicinal Chemistry, 2002, 37, 979-984) to yield compound of formula 3 (Reaction 1a);

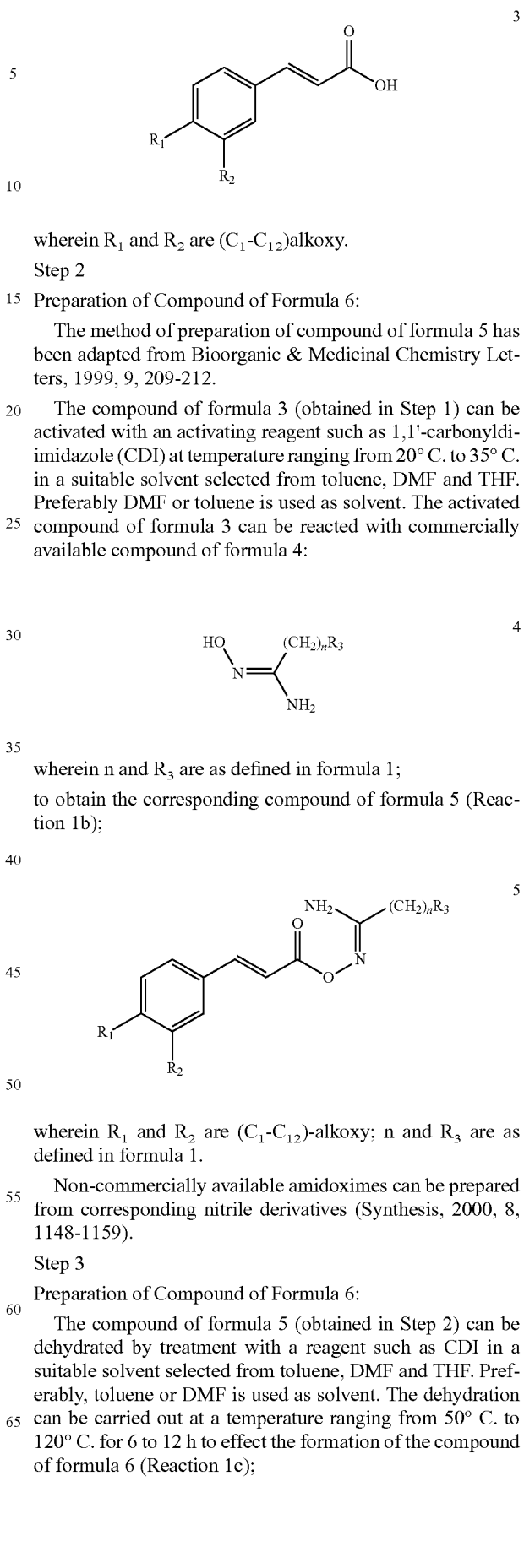

wherein $R_1$ and $R_2$ are $(C_1-C_{12})$alkoxy.

Step 2
Preparation of Compound of Formula 6:

The method of preparation of compound of formula 5 has been adapted from Bioorganic & Medicinal Chemistry Letters, 1999, 9, 209-212.

The compound of formula 3 (obtained in Step 1) can be activated with an activating reagent such as 1,1'-carbonyldiimidazole (CDI) at temperature ranging from 20° C. to 35° C. in a suitable solvent selected from toluene, DMF and THF. Preferably DMF or toluene is used as solvent. The activated compound of formula 3 can be reacted with commercially available compound of formula 4:

wherein n and $R_3$ are as defined in formula 1;
to obtain the corresponding compound of formula 5 (Reaction 1b);

wherein $R_1$ and $R_2$ are $(C_1-C_{12})$-alkoxy; n and $R_3$ are as defined in formula 1.

Non-commercially available amidoximes can be prepared from corresponding nitrile derivatives (Synthesis, 2000, 8, 1148-1159).

Step 3
Preparation of Compound of Formula 6:

The compound of formula 5 (obtained in Step 2) can be dehydrated by treatment with a reagent such as CDI in a suitable solvent selected from toluene, DMF and THF. Preferably, toluene or DMF is used as solvent. The dehydration can be carried out at a temperature ranging from 50° C. to 120° C. for 6 to 12 h to effect the formation of the compound of formula 6 (Reaction 1c);

6

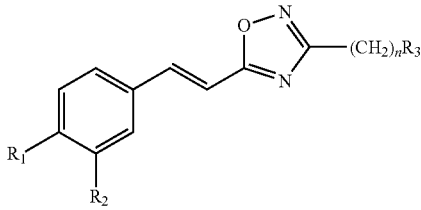

wherein $R_1$ and $R_2$ are $(C_1-C_{12})$-alkoxy; and n and $R_3$ are as defined in formula 1.

Step 4

Preparation of Compound of Formula 7:

The dealkylation of the alkoxy groups of compound of formula 6 (obtained in Step 3) can be effected with suitable dealkylating agents. For example, demethylation of methoxy groups may be carried out using demethylating agents selected from suitable Lewis acids such as boron tribromide in a suitable solvent such as dichloromethane at a temperature ranging from −78° C. to 0° C. to obtain compound of formula 7. Alternately, anhydrous $AlCl_3$/DMS or anhydrous $AlCl_3$/EtSH in a suitable solvent such as dichloromethane at a temperature ranging from 0° C. to 30° C. may be used.

7

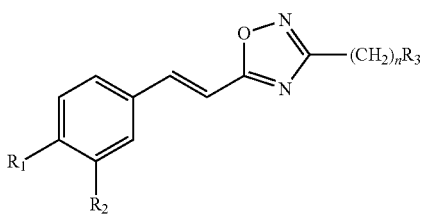

wherein $R_1=R_2=OH$; and n and $R_3$ are as defined in formula 1 (Reaction 1d). Preferably, the demethylating agent used is boron tribromide.

Step 5

The compounds of formula 6 and 7 (corresponding to the compounds of formula 1) can be optionally converted to their corresponding salts.

Scheme 2:

Scheme 2 depicts a process for the preparation of compounds of formula 1 (referred in Scheme 2 as compound 7 wherein $R_1=R_2=OH$; and n and $R_3$ are as defined in formula 1). Said process includes steps 1 to 5 as described below:

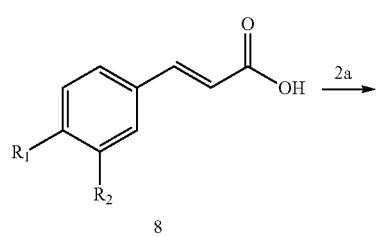

8

-continued

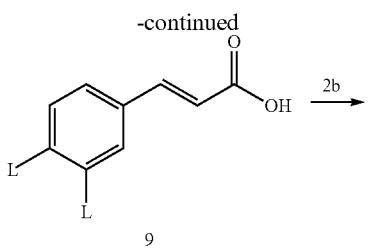

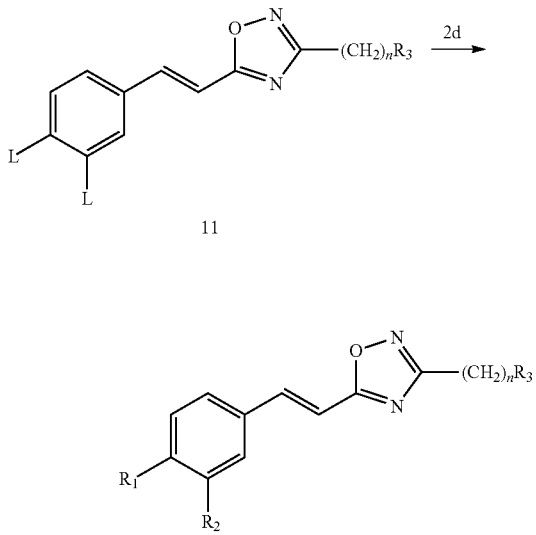

7 ($R_1 = R_2 = OH$)
(Corresponds to compound of formula 1)

Step 1

Preparation of Compound of Formula 9:

Commercially available compound of formula 8 (wherein $R_1$ and $R_2$ are OH) can be converted to compound of formula 9 (wherein L refers to a protected hydroxy group such as the t-butyldimethylsilyloxy group). For example, the OH groups can be protected by treatment with t-butyldimethylsilyl chloride (TBDMSCl) in presence of a suitable base such as imidazole (Tetrahedron Asymmetry, 1996, 8, 2371-2379) in a suitable solvent such as dry DMF over a period of 40-100 h at a temperature ranging from 20° C. to 35° C. to give a mixture of compound of formula 9 (wherein L is t-butyldimethylsilyloxy) and its corresponding ester with TBDMS. The mixture of compound of formula 9 and its TBDMS ester can be dissolved in a suitable solvent such as a mixture of THF and methanol and treated with a base such as aqueous potassium carbonate followed by treatment with an acid such as citric acid to give compound of formula 9 as the major product (Reaction 2a);

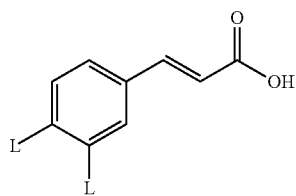

9 wherein L is protected hydroxy such as the t-butyldimethyl-silyloxy group;

Step 2
Preparation of Compound of Formula 10:

The compound of formula 9 (obtained in Step 1) can be converted to acid chloride by any suitable method well known in the art. For example, compound of formula 9 may be dissolved in a suitable solvent such as dichloromethane and treated with oxalyl chloride in the presence of catalytic amount of DMF at a temperature range of 20° C. to 35° C. to obtain the corresponding acid chloride as compound of formula 10 (Reaction 2b);

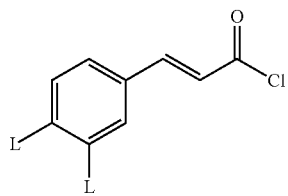

10 wherein L is protected hydroxy such as the t-butyldimethyl-silyloxy group.

Step 3
Preparation of Compound of Formula 11:

The compound of formula 10 (obtained in Step 2) can be dissolved in a suitable solvent such as xylene or toluene in the presence of a suitable base such as pyridine and treated with compound of formula 4:

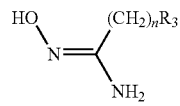

4 wherein n and $R_3$ are as defined in formula 1;
at a temperature ranging from 120° C. to 140° C. (Journal of Medicinal Chemistry, 2004, 47, 6662-6665) to obtain compound of formula 11 (Reaction 2c);

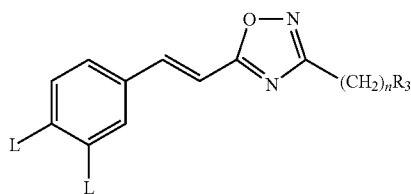

11 wherein L is protected hydroxy such as the t-butyldimethyl-silyloxy group; and n and $R_3$ are as defined in formula 1.
Preferably, a mixture of xylene and pyridine is used Step 4
Preparation of Compound of Formula 7:

Compound of formula 7 can be obtained from compound of formula 11 (obtained in Step 3) by deprotection (e.g. desilylation) of the L group by reacting with any suitable deprotecting agent. For example, t-butyldimethylsilyloxy group may be deprotected using 1.0 M TBAF solution in THF at a temperature ranging from 20° C. to 35° C. (Reaction 2d).

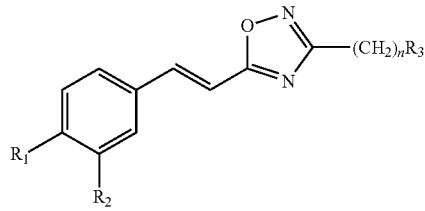

7 wherein $R_1=R_2=OH$; and n and $R_3$ are as defined in formula 1.

Step 5

Compound of formula 7 (corresponding to the compound of formula 1) can be optionally converted to its corresponding salt.

Scheme 3:

Scheme 3 depicts a process for the preparation of compounds of formula 1 (referred in Scheme 3 as compound 7 wherein $R_1=R_2=OH$; n and $R_3$ are as defined in formula 1). Said process includes steps 1 to 4 as described below:

8

12

13

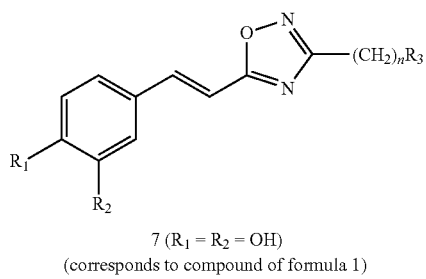

7 ($R_1 = R_2 = OH$)
(corresponds to compound of formula 1)

Step 1
Preparation of Compound of Formula 12:

Commercially available compound of formula 8 (wherein $R_1$ and $R_2$ are OH) which is also known as caffeic acid can be converted to the corresponding ester of formula 12 (wherein $R_1=R_2=OH$; and X is alkyl) by any suitable method. For example, the methyl ester of formula 12 (wherein X is methyl) may be prepared by the reaction of compound of formula 8 with methanol in presence of oxalyl chloride at a temperature ranging from 20° C. to 35° C. (Reaction 3a);

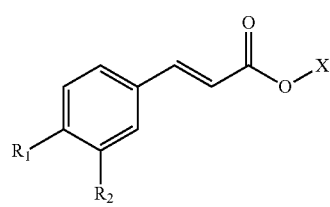

12 wherein $R_1=R_2=OH$; and X is alkyl such as methyl;

Step 2
Preparation of Compound of Formula 13:

Compound of formula 12 (obtained in Step 1) can be treated with suitable protecting agent such as TBDMSCl in the presence of a suitable base such as imidazole in a solvent such as THF or methanol, at a temperature ranging from 20° C. to 35° C. to obtain compound of formula 13 (Reaction 3b);

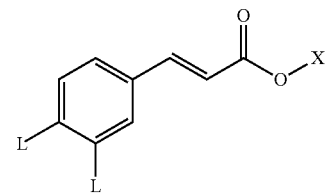

13 wherein L is protected hydroxy such as the t-butyldimethyl-silyloxy group and X is alkyl such as methyl.

Step 3
Preparation of Compound of Formula 7:

Compound of formula 13 (obtained in Step 2) can be treated with compound of formula 4:

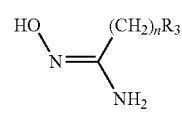

4 wherein n and $R_3$ are as defined in formula 1;
in the presence of suitable base such as sodium hydride in a suitable solvent such as THF at a temperature ranging from 40° C. to 80° C. for 6 to 8 h to obtain compound of formula 7 (Reaction 3c);

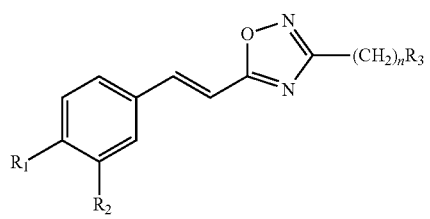

7 wherein $R_1=R_2=OH$, and n and $R_3$ are as defined in formula 1.

Step 4

Compound of formula 7 (corresponding to the compound of formula 1) can be optionally converted to its corresponding salt.

Scheme 4:

Scheme 4 depicts a process for the preparation of compound of formula 1 (referred in Scheme 4 as compound 18 ($R_1=(C_1-C_{12})$alkoxy; $R_2=NO_2$), compound 19 ($R_1=(C_1-C_{12})$-alkoxy; $R_2=NH_2$), compound 20 ($R_1=(C_1-C_{12})$alkoxy; $R_2=NHSO_2$-alkyl or $NHSO_2$-aryl), compound 21 ($R_1$=hydroxy; $R_2=NHSO_2$-alkyl or $NHSO_2$-aryl), wherein n and $R_3$ are as defined in formula 1). Said process includes steps 1 to 8 as described below:

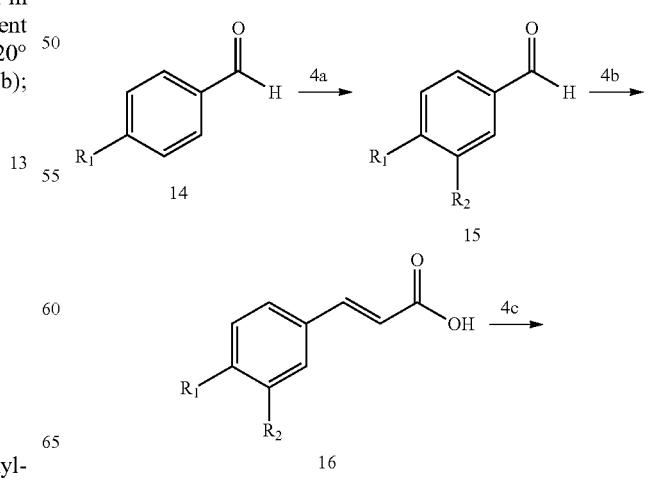

-continued

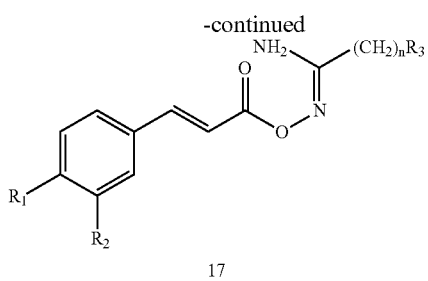

17

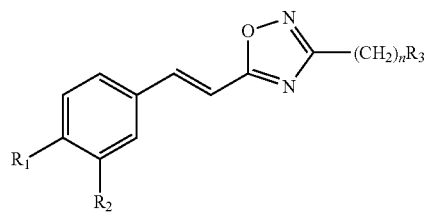

18 ($R_1$ = ($C_1$—$C_{12}$)alkoxy, $R_2$ = $NO_2$)

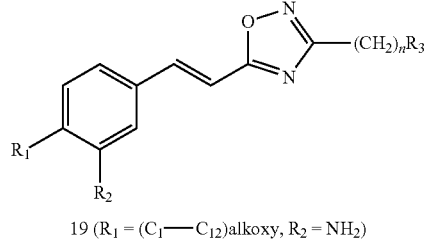

19 ($R_1$ = ($C_1$—$C_{12}$)alkoxy, $R_2$ = $NH_2$)

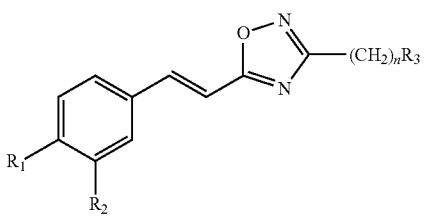

20 ($R_1$ = ($C_1$—$C_{12}$)alkoxy, $R_2$ = $NHSO_2$-alkyl or $NHSO_2$-aryl)

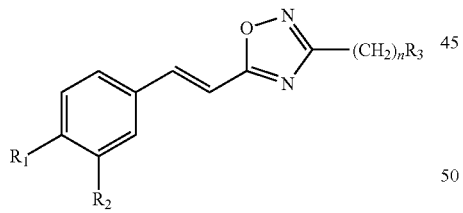

22 ($R_1$ = OH, $R_2$ = $NHSO_2$·alkyl or $NHSO_2$-aryl)

(compound(s) 18, 19, 20 and 21 correspond to the compound of formula 1)

Step 1
Preparation of Compound of Formula 15:

Compound of formula 14 (wherein $R_1$ is ($C_1$-$C_{12}$)alkoxy) i.e. 4-alkoxy benzaldehyde can be converted into compound of formula 15 (wherein $R_1$ is ($C_1$-$C_{12}$)alkoxy, and $R_2$ is nitro) by nitration using a suitable nitrating agent such as ammonium nitrate and trifluoroacetic anhydride (TFAA) at a temperature ranging from 25° C. to 30° C. Alternately, a mixture of $HNO_3$ and $H_2SO_4$ may be used as the nitrating agent (Reaction 4a);

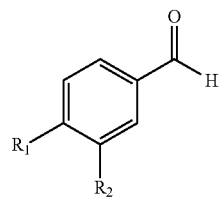

15 wherein $R_1$ is ($C_1$-$C_{12}$)alkoxy and $R_2$ is nitro.

Step 2
Preparation of Compound of Formula 16:

The compound of formula 15 (obtained in Step 1) can be subjected to Knoevenagel condensation with malonic acid to obtain compound of formula 16 (Reaction 4b);

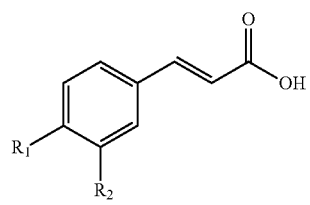

16 wherein $R_1$ is ($C_1$-$C_{12}$)alkoxy and $R_2$ is nitro.

Step 3
Preparation of Compound of Formula 17:

Compound of formula 16 (obtained in Step 2) can be dissolved in a suitable solvent such as DMF or THF and activated with a suitable reagent such as 1,1'-carbonyldiimidazole (CDI) or 1-hydroxybenzotriazole (HOBO at a temperature ranging from 20° C. to 35° C. Activated compound of formula 16 can be further treated with compound of formula 4:

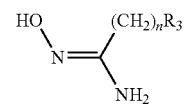

4 wherein n and $R_3$ are as defined in formula 1;
to obtain the corresponding o-acyl amidoximes as compound of formula 17 (Reaction 4c);

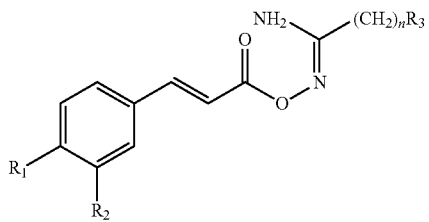

17 wherein $R_1$ is ($C_1$-$C_{12}$)alkoxy, $R_2$ is nitro, and n and $R_3$ are as defined in formula 1. Non-commercially available amidoximes can be prepared from corresponding nitrile derivatives.

Step 4
Preparation of Compound of Formula 18:

The compound of formula 17 (obtained in Step 3) can be dehydrated by treatment with a reagent such as CDI in a suitable solvent such as DMF or THF at a temperature ranging from 50° C. to 120° C., for 6 to 12 h leading to the formation of compound of formula 18 (Reaction 4d);

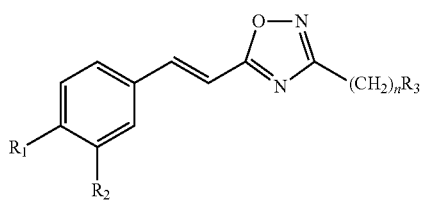

(Corresponds to the compound of formula 1)
wherein $R_1$ is $(C_1$-$C_{12})$alkoxy, $R_2$ is nitro, and n and $R_3$ are as defined in formula 1.

Step 6
Preparation of Compound of Formula 19:

Compound of formula 18 (obtained in Step 4) can be treated with a reducing agent such as stannous chloride in a suitable solvent such as ethyl acetate or methanol at a temperature ranging from 50° C. to 100° C. to obtain compound of formula 19. Alternately, Fe/HCl may be used. Preferably, stannous chloride is used as reducing agent (Reaction 4e);

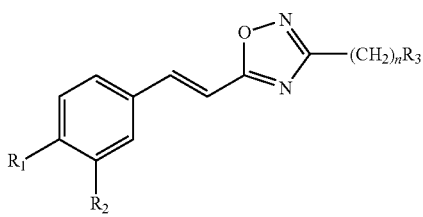

(corresponds to the compound of formula 1)
wherein $R_1$ is $(C_1$-$C_{12})$alkoxy, $R_2$ is $NH_2$, and n and $R_3$ are as defined in formula 1.

Step 6
Preparation of Compound of Formula 20:

The compound of formula 19 (obtained in Step 5) can be reacted with alkyl sulphonyl chloride (for example, methyl sulphonyl chloride) or aryl sulfonyl chloride in a solvent such as dichloromethane in presence of a suitable base such as pyridine or triethylamine at temperature ranging from 20° C. to 40° C. (Reaction 4f), to obtain compound of formula 20;

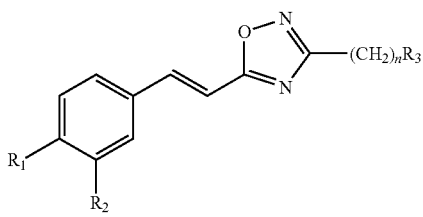

wherein $R_1$ is $(C_1$-$C_{12})$alkoxy, $R_2$ is $NHSO_2$-alkyl or $NHSO_2$-aryl, and n and $R_3$ are as defined in formula 1. Alternately, the reaction may be carried out in pyridine, which may be used as both, solvent and base, Step 7
Preparation of Compound of Formula 21:

The dealkylation of the alkoxy groups of compound of formula 20 (obtained in Step 6) can be effected with suitable dealkylating agents. For example, demethylation of methoxy groups may be carried out using demethylating agents selected from suitable Lewis acids such as boron tribromide in a suitable solvent such as dichloromethane at a temperature ranging from −78° C. to 0° C. to obtain compound of formula 21 (Reaction 4g). Alternately, anhydrous $AlCl_3$/DMS or anhydrous $AlCl_3$/EtSH in a suitable solvent such as dichloromethane at a temperature ranging from 0° C. to 30° C. may be used.

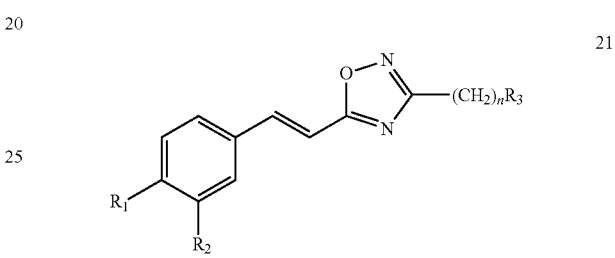

(Corresponds to the compound of formula 1)
wherein $R_1$ is OH, $R_2$ is $NHSO_2$-alkyl or $NHSO_2$-aryl, and n and $R_3$ are as defined in formula 1.

Preferably, the demethylating agent used is boron tribromide.

Step 8

Compounds of formula 18, 19, 20 and 21 (corresponding to the compounds of formula 1) can be optionally converted to their corresponding salts.

Scheme 5:

Scheme 5 depicts a process for the preparation of compound of formula 1 (referred in Scheme 5 as compound 18 ($R_1$=($C_1$-$C_{12}$)alkoxy; $R_2$=$NO_2$), compound 22 ($R_1$=hydroxy; $R_2$=$NO_2$) and compound 23 ($R_1$=hydroxy; $R_2$=$NH_2$) wherein n and $R_3$ are as defined in formula 1). Said process includes steps 1-3 as described below:

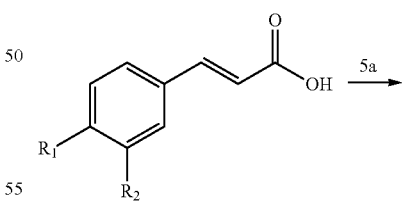

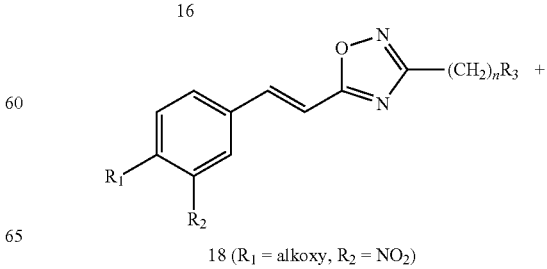

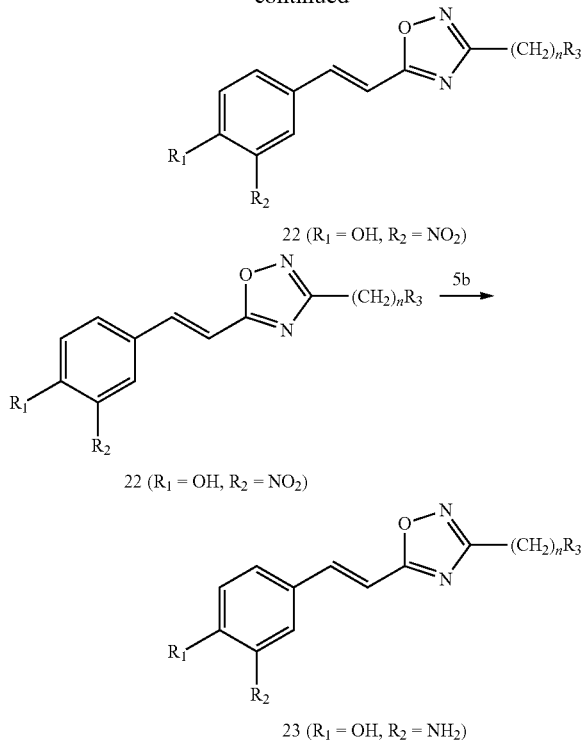

22 ($R_1$ = OH, $R_2$ = NO$_2$)

22 ($R_1$ = OH, $R_2$ = NO$_2$)

23 ($R_1$ = OH, $R_2$ = NH$_2$)

(Compounds 18, 22 and 23 correspond to the compounds of formula 1)

Step 1
Preparation of Compound of Formula 22:

Compound of formula 16 (wherein $R_1$ is ($C_1$-$C_{12}$)alkoxy and $R_2$ is nitro) can be activated using reagents such as 1,1-carbonyldiimidazole (CDI) or a combination of N,N'-dicyclohexyl carbodiimide (DCC) and 1-hydroxybenzotriazole (HOBt) in DMF over a period of 40 min at temperature ranging from 20° C. to 35° C. (Synthetic Communications, 2004, 34, 10, 1863-1870). The activated acid can be refluxed with compound of formula 4;

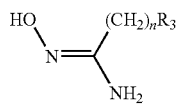

4 wherein n and $R_3$ are as defined in formula 1;
at a temperature ranging from 120° C. to 160° C. for 3-5 h to obtain compound of formula 18 (Reaction 6a);

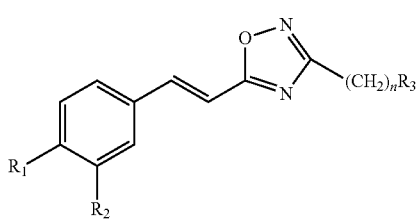

18 wherein $R_1$ is ($C_1$-$C_{12}$)alkoxy and $R_2$ is nitro;

as the major product along with minor amount of dealkylated compound of formula 22;

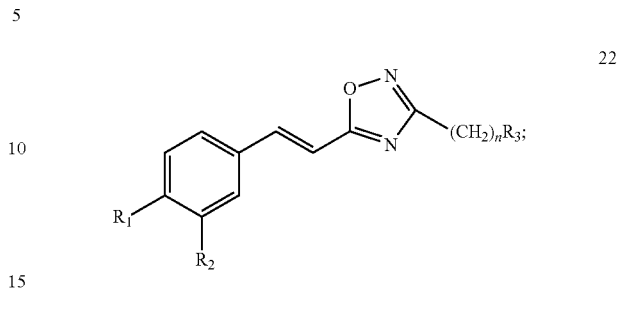

22 wherein $R_1$ is hydroxy and $R_2$ is nitro;

Step 2
Preparation of Compound of Formula 23:

Compound of formula 22 (obtained in Step 1) can be reduced with a suitable reducing agent such as stannous chloride in a suitable solvent such as ethyl acetate or methanol at a temperature ranging from 50° C. to 100° C. to obtain compound of formula 23 (Reaction 5b);

23 wherein $R_1$ is hydroxy and $R_2$ is NH$_2$.

Step 3
Compounds of formula 22 and 23 (corresponding to the compounds of formula 1) can be optionally converted to their corresponding salts.

Scheme 6:
Scheme 6 depicts a process for the preparation of the compound of formula 1 (referred in Scheme 6 as compound 27 ($R_1$=$R_2$=($C_1$-$C_{12}$)alkoxy), compound 28 ($R_1$=$R_2$=($C_1$-$C_{12}$)alkoxy) and compound 29 ($R_1$=$R_2$=hydroxy)) wherein n=1; $R_3$=

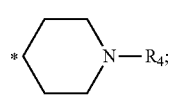

wherein * is the point of attachment and $R_4$ is selected from H, ($C_1$-$C_{12}$)alkyl or benzyl). Said process includes steps 1, 2, 2A-2D and 3-7 as described below:

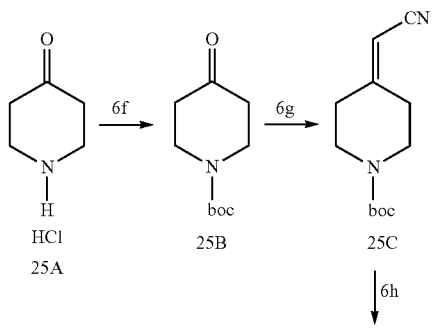
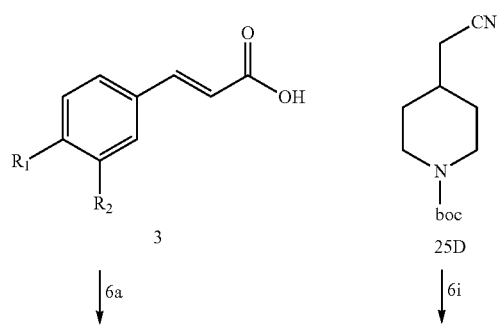
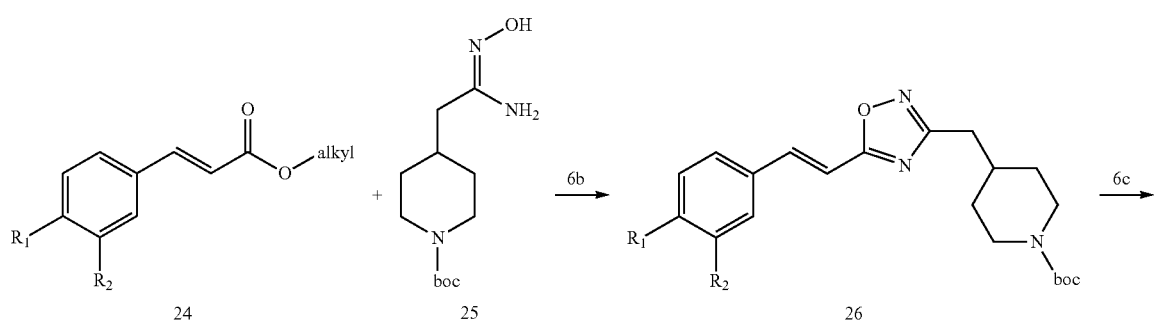
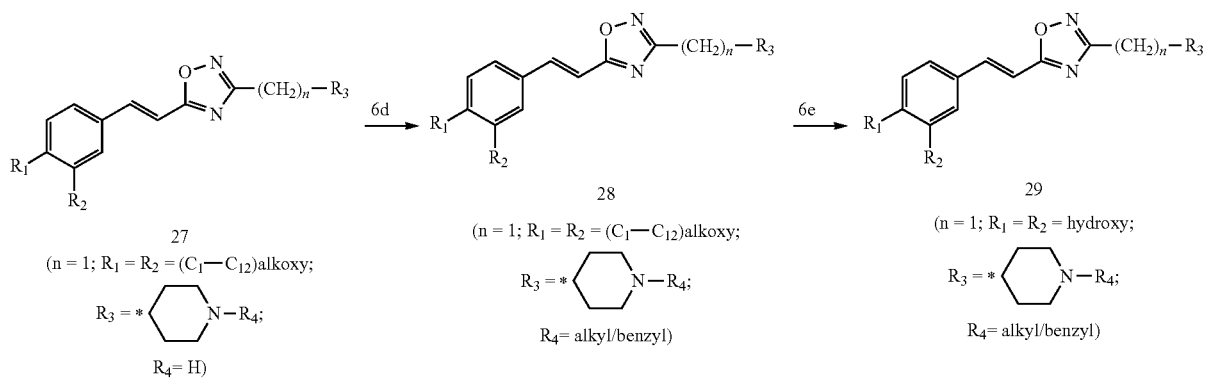

Step

Preparation of Compound of Formula 24:

Compound of formula 3 (wherein $R_1=R_2=(C_1-C_{12})$ alkoxy) can be converted to compound of formula 24, which is the corresponding alkyl ester by conventional method (Reaction 6a);

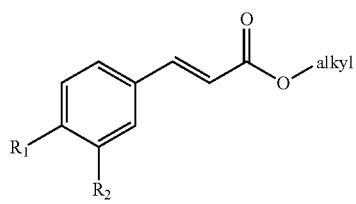

24 wherein $R_1=R_2$=alkoxy. For example, compound of formula 3 can be converted to the corresponding methyl ester, Step 2

Preparation of Compound of Formula 25:

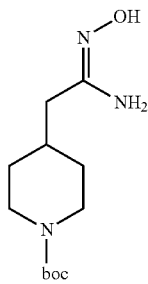

25

Step 2A

Preparation of Compound of Formula 26B:

Commercially available compound of formula 25A,

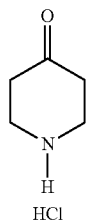

25A can be treated with t-butoxycarbamate in presence of a suitable base such as aqueous sodium hydroxide in a suitable solvent such as THF or dichloromethane at a temperature ranging from 20° C. to 35° C. to obtain compound of formula 25B (Reaction 6f).

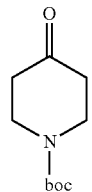

25B

Step 2B

Preparation of Compound of Formula 25C:

Compound of formula 25B can be refluxed with a cyanomethylating reagent such as cyanomethyl phosphonic acid diethylester in presence of a suitable base such as anhydrous potassium carbonate in a suitable solvent such as THF at a temperature ranging from 20° C. to 50° C. to obtain compound of formula 25C (Reaction 6g).

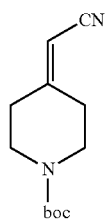

25C

Step 2C

Preparation of Compound of Formula 25D:

Compound of formula 25C can be reduced using a suitable reducing agent such as $H_2$/Pd—C in a suitable solvent such as methanol at a temperature ranging from 20° C. to 35° C. at a pressure ranging from 40-60 psi to obtain compound of formula 25D (Reaction 6h).

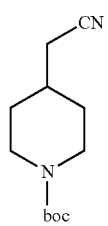

25D

Step 2D

Preparation of Compound of Formula 25:

Compound of formula 25D can be treated with hydroxylamine hydrochloride in presence of a suitable base such as anhydrous potassium carbonate in a suitable solvent such as alcohol or aqueous alcohol at a temperature ranging from 20° C. to 35° C. (Reaction 6I) to obtain compound of formula 25.

Step 3

Preparation of Compound of Formula 26:

Compound of formula 24 (obtained in Step 1) can be treated with compound of formula 26 (obtained in Step 2C); in the presence of suitable base such as sodium hydride in a suitable solvent such as THF (Journal of Medicinal Chemistry, 1993, 22, 3397-3408) at a temperature ranging from 20° C. to 60° C. to obtain compound of formula 26 (Reaction 6b);

wherein $R_1$ and $R_2$ are $(C_1$-$C_{12})$alkoxy.

Step 4

Preparation of Compound of Formula 27:

Compound of formula 26 (obtained in Step 3) can be deprotected with suitable deprotecting agent such as trifluoroacetic acid in a suitable solvent such as dichloromethane at a temperature ranging from 20° C. to 35° C. to obtain compound of formula 27 (Reaction 6c);

wherein $R_1$ and $R_2$ are $(C_1$-$C_{12})$alkoxy; and n=1; $R_3$ is wherein $R_4$ is hydrogen.

Step 5

Preparation of Compound of Formula 28:

Compound of formula 27 (obtained in Step 4) can be alkylated by heating with alkyl halide or benzyl halide in presence of a suitable base such as anhydrous $K_2CO_3$ or sodium hydride, in a suitable solvent such as dry DMF, at a temperature ranging from 25° C. to 100° C. to obtain compound of formula 28 (Reaction 6d);

wherein $R_1$ and $R_2$ are $(C_1$-$C_{12})$alkoxy; and n=1; $R_3$ is wherein $R_4$ is selected from alkyl and benzyl.

Step 6

Preparation of Compound of Formula 27A or Compound of Formula 29:

Compound of formula 28 (obtained in Step 5) can be treated with a suitable dealkylating agent, for example, in order to carry out demethylation of methoxy groups, compound of formula 28 can be treated with suitable Lewis acid such as boron tribromide in a suitable solvent such as dichloromethane at a temperature ranging from −78° C. to 0° C. to obtain compound of formula 29 (Reaction 6e). Alternately, anhydrous $AlCl_3$/DMS or anhydrous $AlCl_3$/EtSH in a suitable solvent such as dichloromethane at a temperature ranging from 0° C. to 30° C. may be used.

wherein $R_1$ and $R_2$ are hydroxy; and n=1; $R_3$ is wherein $R_4$ is selected from alkyl and benzyl.

Preferably, the demethylating agent used is boron tribromide.

Similarly, compound of formula 27 (obtained in Step 4) can be converted to compound of formula 27A;

wherein $R_1$ and $R_2$ are hydroxy; and n=1;

37

R₃ is

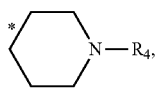

wherein R₄ is hydrogen.

Step 7

Compounds of formula 27, 27A, 28 and 29 (corresponding to the compounds of formula 1) can be optionally converted to their corresponding salts.

Scheme 7:

Scheme 7 depicts a process for the preparation of compound of formula 1 (referred in Scheme 7 as compound 27

38

($R_1=R_2=(C_1-C_{12})$alkoxy; $R_4$ is hydrogen), compound 27A ($R_1=R_2=$hydroxy; $R_4$ is hydrogen), compound 28 ($R_1=R_2=(C_1-C_{12})$alkoxy; $R_4$ is alkyl or benzyl) and compound 29 ($R_7=R_2=$hydroxy; $R_4$ is alkyl or benzyl) wherein n=1; $R_3=$

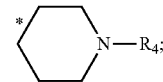

wherein * is the point of attachment.). Said process includes steps 1, 2, 2A-2D and 3-5 as described below:

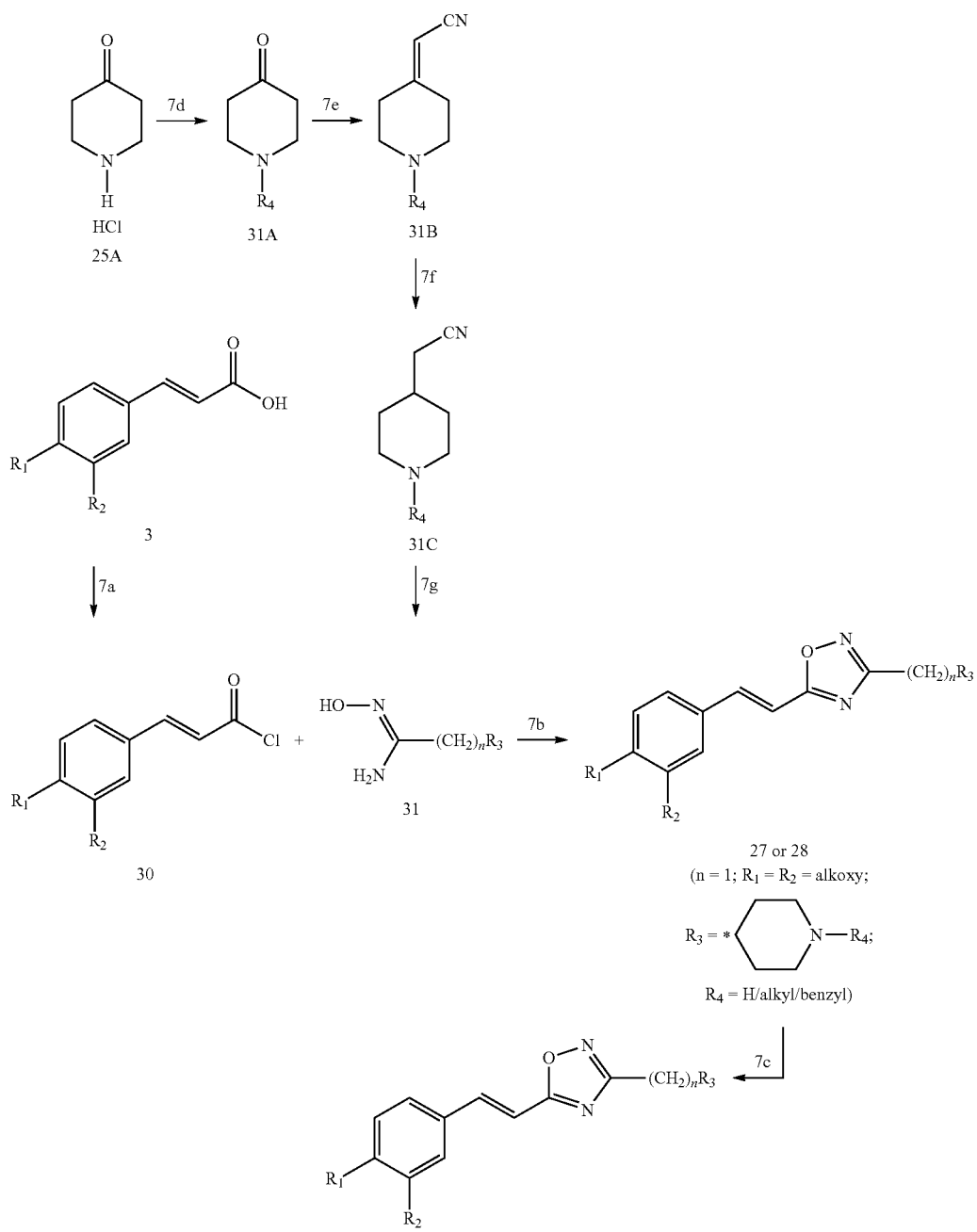

-continued
27A or 29

(n = 1; $R_1 = R_2$ = hydroxy;

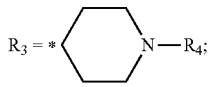

$R_4$ = H/alkyl/benzyl)

(Compounds 27, 27A, 28 and 29 correspond to the compounds of formula 1)

Step 1
Preparation of Compound of Formula 30:
Compound of formula 3 (wherein $R_1=R_2=(C_1-C_{12})$ alkoxy) can be converted to compound of formula 30, which is the corresponding acid chloride of the compound of formula 3, by using a conventional method (Reaction 7a);

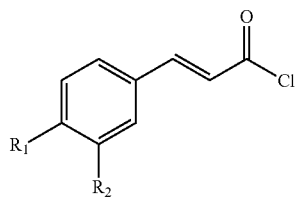

30 wherein $R_1$ and $R_2$ are $(C_1-C_{12})$alkoxy.
Step 2
Preparation of Compound of Formula 31:

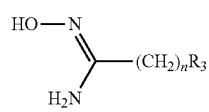

31 wherein n=1 and $R_3$ is

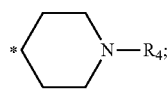

wherein * is the point of attachment and $R_4$ is selected from hydrogen, alkyl and benzyl.
Step 2A
Preparation of Compound of Formula 31A:
Commercially available compound of formula 25A;

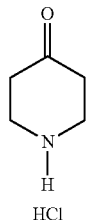

25A can be treated with $R_4$—X (wherein $R_4$ is selected from alkyl and benzyl and X is halide) in presence of suitable base such as anhydrous potassium carbonate in a suitable solvent such as dry DMF at a temperature ranging from 20° C. to 35° C. to obtain compound of formula 31A (Reaction 7d).

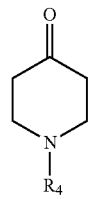

31A

Step 2B
Preparation of Compound of Formula 31B:
Compound of formula 25A or 31A can be refluxed with a cyanomethylating reagent such as cyanomethyl phosphonic acid diethylester in presence of a suitable base such as anhydrous potassium carbonate in a suitable solvent such as THF at a temperature ranging from 20° C. to 35° C. to obtain compound of formula 31B (Reaction 7e).

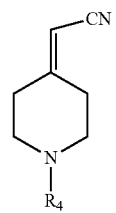

31B

Step 2C
Preparation of Compound of Formula 31C:
Compound of formula 31B in a suitable solvent such as methanol can be treated with suitable reducing agent such as magnesium turnings (Journal of Medicinal Chemistry, 1999, 42, 730-741) at a temperature ranging from 0° C. to 10° C. to obtain compound of formula 31C (Reaction 7f).

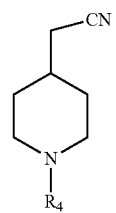

31C

Step 2D
Preparation of Compound of Formula 31:

Compound of formula 31C can be treated with hydroxylamine hydrochloride in presence of a suitable base such as anhydrous potassium carbonate in a suitable solvent such as alcohol or aqueous alcohol at a temperature ranging from 20° C. to 35° C. (Reaction 7g) to obtain compound of formula 31;

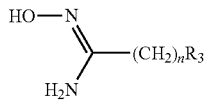

31 wherein n=1 and R₃ is

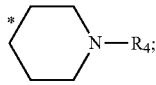

wherein * is the point of attachment and $R_4$ is selected from hydrogen, $(C_1-C_{12})$alkyl and benzyl.

Step 3
Preparation of Compound of Formula 27 or Compound of Formula 28:

Compound of formula 30 (obtained in Step 1) can be treated with compound of formula 31 (obtained in Step 2D) in a suitable solvent such as xylene or toluene in presence of a suitable base such as pyridine at a temperature ranging from 120° C. to 140° C. to obtain compound of formula 27 or compound of formula 28 (Reaction 7b);

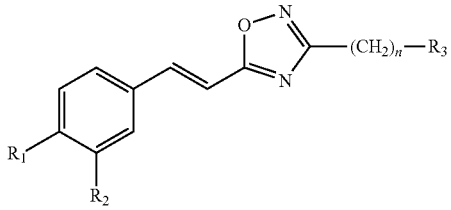

27 or 28 wherein $R_1$ and $R_2$ are $(C_1-C_{12})$alkoxy; n=1; $R_3$ is

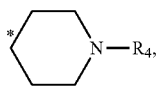

wherein in compound 27, $R_4$ is hydrogen and in compound 28, $R_4$ is selected from alkyl and benzyl.

Alternatively, base such as sodium acetate in a suitable solvent such as aqueous ethanol may be used.

Step 4
Preparation of Compound of Formula 27A or Compound of Formula 29:

Compound of formula 27 (obtained in Step 3) can be treated with a suitable dealkylating agent, for example, in order to carry out demethylation of methoxy groups, compound of formula 27 can be treated with suitable Lewis acid such as boron tribromide in a suitable solvent such as dichloromethane at a temperature ranging from −78° C. to 0° C. to obtain compound of formula 27A (Reaction 7c). Alternately, anhydrous $AlCl_3$/DMS or anhydrous $AlCl_3$/EtSH in a suitable solvent such as dichloromethane at a temperature ranging from 0° C. to 30° C. may be used.

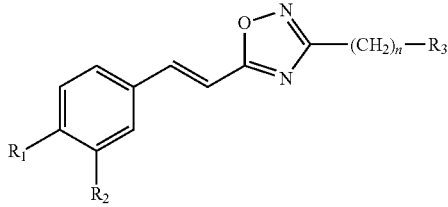

27A wherein $R_1$ and $R_2$ are hydroxy; n=1; and $R_3$ is

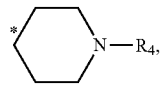

wherein $R_4$ is hydrogen.

Similarly, compound of formula 28 can be converted to compound of formula 29 (Reaction 7c);

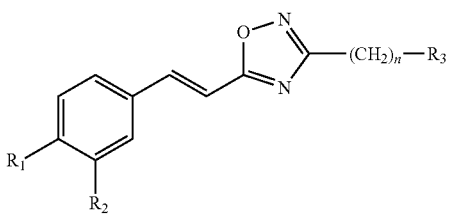

29 wherein $R_1$ and $R_2$ are hydroxy; n=1; and $R_3$ is

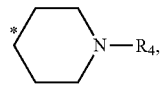

wherein $R_4$ is selected from alkyl and benzyl.

Preferably, the demethylating agent used is boron tribromide.

Step 5

Compounds of formula 27, 27A, 28 and 29 (corresponding to the compounds of formula 1) can be optionally converted to their corresponding salts.

The present invention also includes within its scope all isotopically labeled forms of compounds of formula 1, wherein one or more atoms of compounds of formula 1 are replaced by their respective isotopes. Examples of isotopes that may be incorporated into the compounds disclosed herein include, but are not limited to, isotopes of hydrogen such as $^2H$ and $^3H$, carbon such as $^{11}C$, $^{13}C$ and $^{14}C$, nitrogen such as $^{13}N$ and $^{15}N$, oxygen such as $^{15}O$, $^{17}O$ and $^{18}O$, chlorine such as $^{36}Cl$, fluorine such as $^{18}F$ and sulphur such as $^{35}S$.

Substitution with heavier isotopes, for example, replacing one or more key carbon-hydrogen bonds with carbon-deuterium bond may show certain therapeutic advantages, for example, longer metabolism cycles, improved safety or greater effectiveness.

Isotopically labeled forms of compounds of formula 1, can be prepared by conventional techniques known to those skilled in the art or by processes analogous to those described above and in the subsequent section on examples by using an appropriate isotopically labeled reagent instead of non-labeled reagent.

The compounds of the present invention can also be utilized in the form of their pharmaceutically acceptable salts or solvates thereof. The pharmaceutically acceptable salts of the compounds of the present invention are in particular salts, which can be used physiologically.

The term "pharmaceutically acceptable salts" is meant to include salts of the active compounds which are prepared with acids or bases, depending on the particular substituents found on the compounds described herein. When compounds of the present invention contain relatively acidic functionalities, base addition salts can be obtained by contacting the compounds with a sufficient amount of the desired base, either neat or in a suitable inert solvent. Examples of pharmaceutically acceptable base addition salts include sodium, potassium, calcium, magnesium, ammonium or organic base salt, or a similar salt. Examples of pharmaceutically acceptable organic base addition salts include those derived from organic bases like lysine, arginine, guanidine, diethanolamine and the like.

When compounds of the present invention contain relatively basic functionalities, acid addition salts can be obtained by contacting the compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric or hydriodic acids and the like, as well as the salts derived from organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, glucuronic or galacturonic acids and the like. Certain specific compounds of the present invention contain both basic and acidic functionalities that allow the compounds to be converted into either base or acid addition salts.

The compounds may be regenerated by contacting the salt with a base or acid and isolating the parent compound in the conventional manner. The compound differs from the various salt forms in certain physical properties. An example of physical properties that may differ is solubility in polar solvents.

Certain compounds of the present invention can exist in unsolvated forms as well as solvated forms, including hydrated forms. Certain compounds of the present invention may exist in multiple crystalline or amorphous forms. In general, all physical forms are suitable for the uses contemplated by the present invention and are intended to be within the scope of the present invention.

Various polymorphs of compounds of formula 1 can be prepared by crystallization of the compounds under different conditions. The different conditions are, for example, using different solvents or their mixtures for crystallization; crystallization at different temperatures; various modes of cooling, ranging from very fast to very slow cooling during crystallizations. Polymorphs can also be obtained by heating or melting the compound followed by gradual or fast cooling. The presence of polymorphs can be determined by IR (Infrared) spectroscopy, solid probe NMR (Nuclear Magnetic Resonance) spectroscopy, differential scanning calorimetry, powder X-ray diffraction or such other techniques.

Those skilled in the art will recognize that stereocentres exist in compounds of formula 1. Accordingly, the present invention includes all possible stereoisomers and geometric isomers of formula 1 and includes not only racemic compounds but also the optically active isomers as well. When a compound of formula 1 is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art for example *Chiral reagents for Asymmetric Synthesis* by Leo A. Paquette; John Wiley & Sons Ltd (2003).

Additionally, in situations wherein tautomers of the compounds of formula 1 are possible, the present invention is intended to include all tautomeric forms of the compounds.

The present invention also envisages prodrugs of the compound of formula 1. Prodrug derivatives of any compound of the invention are derivatives of said compounds which following administration release the parent compound in vivo via some chemical or physiological process, e.g., a prodrug on being brought to the physiological pH or through enzyme action is converted to the parent compound. The preferable prodrugs are those that are converted intracellularly, more preferably where the cellular converting location is the site of therapeutic action. For instance, preferred produgs are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters such as the pivaloyloxymethyl ester and the like conventionally used in the art (An introduction to Medicinal Chemistry, Graham. L. Patrick, Second Edition, Oxford University Press, pg 239-248; Prodrugs: Challenges and Rewards, Part 1 and Part 2, AAPS Press, Edited by Valentino J. Stella, Renald T. Borchardt, Michael J. Hagemon, Reza Oliyai, Hans Maag, Jefferson W. Tilley)

The present invention furthermore relates to pharmaceutical compositions that contain an effective amount of at least one compound of formula 1 or its physiologically tolerable salt in addition to a customary pharmaceutically acceptable carrier, and to a process for the production of a pharmaceutical compositions, which includes bringing at least one compound of formula 1, into a suitable administration form using a pharmaceutically suitable and physiologically tolerable excipient and, if appropriate, further suitable active compounds, additives or auxiliaries.

As used herein, the term "pharmaceutically acceptable carrier" refers to a material that is non-toxic, inert, solid, semi-solid or liquid filler, diluent, encapsulating material or formulation auxiliary of any type which is compatible with a subject, preferably a mammal, more preferably a human, and is suitable for delivering an active agent to the target site without terminating the activity of the agent.

The present invention also envisages the use of a compound of formula 1 or a pharmaceutically acceptable salt of the compound in combination with other pharmaceutically active compounds. For instance, a pharmaceutical composition including a compound of formula 1 or a pharmaceutically acceptable salt can be administered to a mammal, in particular a human, with any other anti-cancer compound, for instance, with first and second generation Bcr-Abl inhibitors such as imatinib and dasatinib, in mixtures with one another or in the form of pharmaceutical preparations.

The term, "therapeutically effective amount" as used herein means an amount of compound or composition comprising compound of formula 1, effective in producing the desired therapeutic response in a particular patient suffering from cancer. The therapeutically effective amount of the compound or composition will vary with the particular condition being treated, the age and physical condition of the end user, the severity of the condition being treated, the duration of the treatment, the nature of concurrent therapy, the specific compound or composition employed, the particular pharmaceutically acceptable carrier utilized, and like factors.

The term "subject" as used herein refers to an animal, preferably a mammal, and most preferably a human.

The term "mammal" used herein refers to warm-blooded vertebrate animals of the class Mammalia, including humans, characterized by a covering of hair on the skin and, in the female, milk-producing mammary glands for nourishing the young. The term mammal includes animals such as cat, dog, rabbit, bear, fox, wolf, monkey, deer, mouse, pig as well as human.

As used herein, the terms "treatment" "treat" and "therapy" and the like refer to alleviate, slow the progression, attenuation or cure of existing disease or condition (e.g., cancer). Treatment also includes treating the symptoms of the disease or condition.

Representative cancer that can be treated by the compounds of the present invention are selected from, but not limited to bladder cancer, breast cancer, colorectal cancer, endometrial cancer, head and neck cancer, lung cancer, lymphoma, melanoma, non-small-cell lung cancer, ovarian cancer, prostate cancer, testicular cancer, renal cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors, non-Hodgkin's lymphoma, osteosarcoma, malignant fibrous histiocytoma of bone, retinoblastoma, rhabdomyosarcoma, soft tissue sarcomas, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer and small-cell lung cancer.

In another aspect, the cancer that can be treated by the compounds of the present invention are selected from leukemia, acute lymphoblastic leukemia, acute myeloid leukemia, acute lymphocytic leukemia, adult acute myeloid leukemia, chronic lymphocytic leukemia, chronic myeloid leukemia, and hairy cell leukemia.

In yet another aspect, the cancer that can be treated is chronic myeloid leukemia.

In a further aspect, the cancer that can be treated by the compounds of the present invention is chronic myeloid leukemia that is resistant to treatment with imatinib mesylate.

In one aspect, the present invention provides a method of treatment of cancer, comprising administering a therapeutically effective amount of a compound of formula 1, to a mammal in need thereof.

In another aspect, the present invention provides a method of treatment of cancer selected from leukemia, acute lymphoblastic leukemia, acute myeloid leukemia, acute lymphocytic leukemia, adult acute myeloid leukemia, chronic lymphocytic leukemia, chronic myeloid leukemia, and hairy cell leukemia; comprising administering a therapeutically effective amount of a compound of formula 1, to a mammal in need thereof.

In yet another aspect, the present invention provides a method of treatment of chronic myeloid leukemia; comprising administering a therapeutically effective amount of a compound of formula 1, to a mammal in need thereof.

In a further aspect, the present invention provides a method of treatment of chronic myeloid leukemia resistant to treatment with imatinib mesylate; comprising administering a therapeutically effective amount of a compound of formula 1, to a mammal in need thereof.

In another aspect, the present invention provides a method of reducing the proliferation of cells that are resistant to treatment with imatinib mesylate; comprising providing said cells with a therapeutically effective amount of the compound of formula 1.

In another aspect, the present invention provides a method of reducing the proliferation of cells that are resistant to treatment with imatinib mesylate; comprising administering to a mammal in need thereof, a therapeutically effective amount of the compound of formula 1.

In one aspect of the invention, the resistance of the cells to treatment with imatinib mesylate is caused by Bcr-Abl mutation.

In another aspect of the invention, the cells resistant to imatinib mesylate are selected from Ba/F3Bcr-Abl/T315I, Ba/F3Bcr-Abl/E255K, Ba/F3Bcr-Abl/H396P, Ba/F3Bcr-Abl/M351T, Ba/F3Bcr-Abl/F359V, Ba/F3Bcr-Abl/E255V, Ba/F3Bcr-Abl/F317L, Ba/F3Bcr-Abl/H396R, Ba/F3Bcr-Abl/M244V, Ba/F3Bcr-Abl/Q252H, Ba/F3Bcr-Abl/Y253F, and Ba/F3Bcr-Abl/Y253H.

In another aspect, the present invention provides a method for inhibiting TGFβ; comprising administering to a mammal in need thereof, a therapeutically effective amount of a compound of formula 1.

In a further aspect, the present invention provides a method for reducing proliferation of CML stem cells mediated by inhibition of TGFβ; comprising administering to a mammal in need thereof, a therapeutically effective amount of a compound of formula 1.

In another aspect, the present invention provides a method for reducing proliferation of CML stem cells mediated by inhibition of TGFβ; comprising providing said CML stem cells with a therapeutically effective amount of a compound of formula 1.

In another aspect, the present invention provides use of a compound of formula 1 for the treatment of cancer.

In another aspect, the present invention provides use of a compound of formula 1 for the treatment of cancer selected from leukemia, acute lymphoblastic leukemia, acute myeloid leukemia, acute lymphocytic leukemia, adult acute myeloid leukemia, chronic lymphocytic leukemia, chronic myeloid leukemia, and hairy cell leukemia.

In yet another aspect, the present invention provides use of a compound of formula 1 for the treatment of chronic myeloid leukemia.

In a further aspect, the present invention provides use of a compound of formula 1 for the treatment of chronic myeloid leukemia, that is resistant to treatment with imatinib mesylate.

In another aspect, the present invention provides use of a compound of formula 1 for inhibition of TGFβ.

In yet another aspect, the present invention provides use of a compound of formula 1 for reducing proliferation of CML (chronic myeloid leukemia) stem cells mediated by inhibition of TGFβ.

In a further aspect, the present invention provides use of a compound of formula 1; for the manufacture of a medicament for the treatment of cancer.

In another aspect, the present invention provides use of a compound of formula 1; for the manufacture of a medicament for the treatment of cancer selected from leukemia, acute lymphoblastic leukemia, acute myeloid leukemia, acute lymphocytic leukemia, adult acute myeloid leukemia, chronic lymphocytic leukemia, chronic myeloid leukemia, and hairy cell leukemia.

In yet another aspect, the present invention provides use of a compound of formula 1; for the manufacture of a medicament for the treatment of chronic myeloid leukemia (CML).

In a further aspect, the present invention provides use of a compound of formula 1; for the manufacture of a medicament for the treatment of chronic myeloid leukemia (CML), that is resistant to treatment with imatinib mesylate.

In one aspect, the compounds of the present invention are used in a method for reducing the population of imatinib mesylate sensitive (e.g., K-562 or Ba/F3Bcr-Abl/WT) and imatinib mesylate resistant chronic myeloid leukemia (CML) cells in-vitro, wherein said cells are selected from Ba/F3Bcr-Abl/T315I, Ba/F3Bcr-Abl/E255K, Ba/F3Bcr-Abl/M351T, Ba/F3Bcr-Abl/F359V, Ba/F3Bcr-Abl/E255V, Ba/F3 Bcr-Abl/F317V, Ba/F3Bcr-Abl/H396R, Ba/F3Bcr-Abl/H396P, Ba/F3Bcr-Abl/M244V, Ba/F3Bcr-Abl/Q252H, Ba/F3Bcr-Abl/Y253F or Ba/F3Bcr-Abl/Y253H.

The in-vivo efficacy of the compounds of the present invention in imatinib mesylate-sensitive and imatinib mesylate-resistant tumor models can be evaluated by using cell lines such as Ba/F3 transfectants expressing full-length wild type Bcr-Abl (Ba/F3Bcr-Abl/WT) or mutated Bcr-Abl (Ba/F3Bcr-Abl/T315I) in xenograft models of SCID (Severely Combined Immune-Deficient) mice.

In another aspect, the treatment methods and methods for reducing cellular proliferation described herein use the pharmaceutical compositions described above can be administered by the following administration routes, modes, etc.

Pharmaceutical Compositions and Methods

The compositions can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of ointments or creams or transdermally, in the form of patches, or in other ways, for example in the form of aerosols or nasal sprays.

As used herein, the term "pharmaceutically acceptable" means that the carrier, diluent, excipients, and/or salt must be compatible with the other ingredients of the formulation, and not deleterious to the recipient thereof.

The pharmaceutical preparations according to the invention are prepared in a manner known and familiar to one skilled in the art. Pharmaceutically acceptable inert inorganic and/or organic carriers and/or additives can be used in addition to the compound(s) of formula 1, and/or its (their) physiologically tolerable salt(s). For the production of pills, tablets, coated tablets and hard gelatin capsules it is possible to use, for example, lactose, corn starch or derivatives thereof, gum arabica, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

The pharmaceutical preparations normally contain about 1 to 99%, for example, about 5 to 70%, or from about 10 to about 30% by weight of the compound of the formula 1 or its physiologically tolerable salt. The amount of the compound of the formula 1 or its physiologically tolerable salt in the pharmaceutical preparations normally is from about 5 to 500 mg. The dose of the compounds of this invention, which is to be administered, can cover a wide range. The dose to be administered daily is to be selected to suit the desired effect. A suitable dosage is about 0.01 to 100 mg/kg/day of the compound of formula 1 or their physiologically tolerable salt, for example, about 0.1 to 50 mg/kg/day of a compound of formula 1 or a pharmaceutically acceptable salt of the compound. If required, higher or lower daily doses can also be administered.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

In addition to the compound of the formula 1 or its physiologically acceptable salt and carrier substances, the pharmaceutical preparations can contain additives such as, for example, fillers, antioxidants, dispersants, emulsifiers, defoamers, flavors, preservatives, solubilizers or colorants. They can also contain two or more compounds of formula 1 or their physiologically tolerable salts. Furthermore, in addition to at least one compound of formula 1 or its physiologically tolerable salt, the pharmaceutical preparations can also contain one or more other therapeutically or prophylactically active ingredients.

It is understood that modifications that do not substantially affect the activity of the various aspects of this invention are included. Accordingly, the following examples are intended to illustrate but not to limit the present invention.

The following abbreviations or terms are used throughout the specification and the appended claims:

$AlCl_3$/DMS: Aluminium chloride-dimethyl sulfide complex
$AlCl_3$/EtSH: Aluminium chloride-ethanethiol complex
$CD_3OD$: Deuteriated methanol
$CDCl_3$: Deuteriated chloroform
CDI: 1,1'-Carbonyldiimidazole
$CO_2$: Carbon dioxide
° C.: degree Centigrade
DCC: N,N'-Dicyclohexyl carbodimide
DMF: N,N-Dimethylformamide
DMSO: Dimethylsulfoxide
DMSO-$d_6$: Deuteriated dimethylsulfoxide
Fe/HCl: iron in hydrochloric acid
g: gram(s)
h: hour(s)
HCl: Hydrochloric acid
$HNO_3$: Nitric acid
$H_2SO_4$: Sulfuric acid HOBt: 1-Hydroxybenzotriazole
K₂CO₃: Potassium carbonate
MeOH: Methanol
mg: milligram(s)
min: minute(s)
mL: milliliter
µL: microliter
mmol: millimole
µM: micromolar
NaCl: Sodium chloride
nM: nanometer
Pd/C: Palladium over activated carbon
Room temperature: 20-35° C.
TBAF: Tributyl ammonium fluoride
TBDMS-Cl: Tetrabutyl dimethyl silyl chloride
THF: Tetrahydrofuran

EXAMPLE 1

4-[2-(3-Methyl-[1,2,4]oxadiazol-5-yl)-vinyl]-benzene-1,2-diol

Step 1: Preparation of 3-[3,4-Bis-(tert-butyl-dimethyl-silanyloxy)-phenyl]-acrylic Acid Methyl Ester A mixture of methyl ester of caffeic acid (13 g, 66.94 mmol) and imidazole (15.95 g, 23.43 mmol) was dissolved in dry DMF (70 mL) at room temperature. Tetrabutyl dimethyl silyl chloride (TBDMS-Cl) (35.31 g, 23.43 mmol) was dissolved in dry DMF (40 mL) and added dropwise to the reaction mixture, which was stirred for about 16-18 h at room temperature. After completion of the reaction, approximately 200 mL of ice water was added. The mixture was extracted with diethyl ether (100 mL) and the combined organic layers were washed with water (2×50 mL) followed by brine (50 mL). The organic phase obtained was dried over anhydrous sodium sulphate and concentrated to dryness. The crude product obtained was purified by crystallisation using petroleum ether to afford the title compound.

Yield: 23.68 g (83.70%); $^1$HNMR (CDCl$_3$, 300 MHz): δ 7.57 (d, 1H), 7.01 (m, 2H), 6.83 (d, 1H), 6.23 (d, 1H), 3.79 (s, 3H), 0.99 (s, 9H), 0.98 (s, 9H), 0.21 (s, 6H), 0.20 (s, 6H).

Step 2: Preparation of 4-[2-(3-Methyl-[1,2,4]oxadiazol-5-yl)-vinyl]-benzene-1,2-diol A solution of N-hydroxy-acetamidine (0.17 g, 2.29 mmol) in dry tetrahydrofuran (5 mL) was added slowly into the suspension of 60% sodium hydride (0.14 g, 3.5 mmol) in dry tetrahydrofuran (5 mL) under nitrogen atmosphere at 0° C. to 10° C. The reaction mixture was stirred for 30 min at room temperature. 3-[3,4-Bis-(tert-butyl-dimethyl-silanyloxy)-phenyl]-acrylic acid methyl ester (compound of Example 1, Step 1; 0.5 g, 1.18 mmol) in dry tetrahydrofuran (5 mL) was added into the reaction mixture and heated at 60° C. for 8 h. The reaction mixture was cooled at 0° C. and quenched with MeOH (2 mL) to destroy excess sodium hydride. The reaction mixture was extracted with ethyl acetate (2×10 mL) and the combined organic layers were washed with water (2×10 mL) followed by brine (10 mL). The organic phase obtained was dried over anhydrous sodium sulphate and concentrated to dryness. The crude product obtained was purified by column chromatography (silica gel, chloroform-methanol) to afford the title compound.

Yield: 0.11 g (42.62%); $^1$HNMR (CD$_3$OD, 300 MHz): δ 7.65 (d, 1H), 7.11 (d, 1H), 7.02 (dd, 1H), 6.83 (d, 2H), 6.80 (d, 1H), 2.36 (s, 3H).

EXAMPLE 2

4-[2-(3-Ethyl-[1,2,4]oxadiazol-5-yl)-vinyl]-benzene-1,2-diol

Method A

Step 1 (Method a): Preparation of 3-(3,4-Dimethoxy-phenyl)-acrylic acid 3,4-Dimethoxybenzaldehyde (25 g, 0.15 mol), malonic acid (32.87 g, 0.31 mol) and piperidine (1 mL) were dissolved in pyridine (100 mL) under stirring. The reaction mixture was heated at 80° C. for 3 h, after which the temperature was further increased to 120° C. and maintained at this temperature for 3 h. The reaction mixture was cooled, diluted with water (70 mL) and pH of the solution was adjusted to 9 by addition of 10% aqueous sodium hydroxide solution. The mixture was extracted with ethyl acetate (3×150 mL). The pH of the aqueous layer was adjusted to 2 by addition of aqueous HCl (1:1) and the resulting solid was filtered and dried to afford the title compound.

Yield: 26 g (83.0%); $^1$H NMR (DMSO-d$_6$, 300 MHz): δ 7.51 (d, 1H), 7.30 (s, 1H), 7.19 (d, 1H), 6.96 (d, 1H), 6.44 (d, 1H), 3.79 (s, 61-1); MS (ES−): 207 (M−1).

Step 1 (Method b): Preparation of 3-(3,4-Dimethoxy-phenyl)-acrylic acid

To a solution of 1000 g (6.024 mol) of 3,4-dimethoxybenzaldehyde in 3 L pyridine, 1378.3 g (13.25 mol) of malonic acid and 100 mL of piperidine were added. The resulting mixture was stirred at 105° C. to 110° C. for 6-8 h. After completion of the reaction, the reaction mixture was cooled to 25° C. to 30° C. and slowly quenched the reaction mixture into 10 L of 5% sodium hydroxide solution at 25° C. to 30° C. (pH: 9-10). The reaction mixture was washed with ethyl acetate (2×5 L) and the organic layer separated was washed with 2 L of 5% sodium hydroxide solution. The aqueous layers were combined and cooled to 15° C. to 20° C. The aqueous layer was acidified slowly with 2.5 L of 50% sulphuric acid below 20° C. (pH: 1-2). After an additional 30-45 min stirring at 15° C. to 20° C., the solid obtained was collected by filtration, washed with 10 L of water followed by 4 L of n-hexane. The partially dried compound was unloaded into trays and dried at 55° C. to 60° C. for 8-10 h to give 1110 g of the title compound.

Yield: 1110 g (88%); $^1$H NMR (DMSO-d$_6$, 300 MHz): δ 7.51 (d, 1H), 7.30 (s, 1H), 7.19 (d, 1H), 6.96 (d, 1H), 6.44 (d, 1H), 3.79 (s, 6H); MS (ES−): 207 (M−1).

Step 2: Preparation of 5-[2-(3,4-Dimethoxy-phenyl)-vinyl]-3-ethyl-[1,2,4]oxadiazole 3-(3,4-Dimethoxy-phenyl)-acrylic acid (compound of Example 2, Method A, Step 1; 4 g, 19.21 mmol) was dissolved in DMF (30 mL) to which 1,1'-Carbonyldiimidazole (CDI) (4.04 g, 24.97 mmol) was added and the reaction mixture was stirred at room temperature. At the end of 3 h, N-hydroxy-propionamidine (2.03 g, 23.05 mmol) was added and the reaction mixture was stirred at room temperature for 8 h. After completion of the reaction, additional CDI (4.04 g, 24.97 mmol) was added and the reaction mixture was refluxed at 110° C. to 120° C. for 8 h to effect cyclodehydration. After evaporation of DMF, the residue obtained was cooled to room temperature followed by addition of water (25 mL) and extracted with ethyl acetate (3×15 mL). The combined organic layers were washed with water (2×10 mL) and brine (10 mL), dried over anhydrous sodium sulfate and concentrated to afford the title compound.

Yield: 1.5 g (30.0%); $^1$H NMR (CD$_3$OD, 300 MHz): δ 7.73 (d, 1H), 7.28 (d, 1H), 7.21 (dd, 1H), 6.98 (m, 2H), 3.91 (s, 3H), 3.86 (s, 3H), 2.74 (q, 2H), 1.31 (t, 3H).

Step 3: Preparation of 4-[2-(3-Ethyl-[1,2,4]oxadiazol-5-yl)-vinyl]-benzene-1,2-diol 5-[2-(3,4-Dimethoxy-phenyl)-vinyl]-3-ethyl-[1,2,4]oxadiazole (compound of Example 2, Method A, Step 2; 0.3 g, 1.15 mmol) was dissolved in dichloromethane (6 mL) and cooled to −78° C. A solution of boron tribromide (0.41 mL, 4.40 mmol) in dichloromethane (4 mL), which was cooled to −50° C., was added slowly over a period of 30 min. After 3 h, the reaction mixture was allowed to warm to room temperature and stirred for 12 h. After the completion of the reaction, the mixture was quenched by dropwise addition of methanol (5 mL) at 0° C. and stirred for 30 min at room temperature. The solvent was evaporated and the residue obtained was redissolved in 10% methanol in chloroform at 0° C., and stirred with solid sodium carbonate to obtain pH ~9. The solvent was evaporated and the crude product obtained was purified by column chromatography (silica gel, 0.5% methanol in chloroform) to afford the title compound.

Yield: 0.06 g (23.0%); MS (ES−): 231 (M−1).

Method B

Step 1: Preparation of 3-[3,4-Bis-(tert-butyl-dimethyl-silanyloxy)-phenyl]-acrylic acid A mixture of caffeic acid (100 g, 0.555 mol) and imidazole (340.09 g, 4.99 mol) was dissolved in dry DMF (1 L) at room temperature to which TBDMS-Cl (376.48 g, 2.49 mol) was added. The reaction mixture was stirred at room temperature over a period of 72 h. After completion of the reaction, approximately 700 mL of ice-water was added. The mixture was extracted with diethyl ether (4×200 mL) and the combined organic layers were washed with water (2×100 mL) followed by brine (50 mL). The organic phase obtained was dried over anhydrous sodium sulphate and concentrated to dryness. The crude product obtained was dissolved in methanol (300 mL) and tetrahydrofuran (500 mL). Solid potassium carbonate was added and the resulting mixture was stirred for 45 min at room temperature to adjust pH of the solution obtained to ~8. The reaction mixture was cooled to 0° C. and pH was adjusted to 6 by addition of saturated aqueous solution of citric acid. The reaction mixture was extracted with diethyl ether (3×300 mL) and the combined organic layers were washed with water (2×100 mL) and brine (1×50 mL). The organic phase obtained was dried over anhydrous sodium sulphate and concentrated to afford the title compound.

Yield: 222 g (97.86%); $^1$HNMR (CDCl$_3$, 300 MHz): δ 7.64 (d, 1H), 7.04 (m, 2H), 6.85 (d, 1H), 6.24 (d, 1H), 1.00 (s, 9H), 0.98 (s, 9H), 0.22 (s, 6H), 0.20 (s, 6H); MS (ES+): 409 (M+1).

Step 2: Preparation of {2-[3,4-Bis-(tert-butyl-dimethyl-silanyloxy)-phenyl]-vinyl}-3-ethyl-[1,2,4]oxadiazole 3-[3,4-Bis-(tert-butyl-dimethyl-silanyloxy)-phenyl]-acrylic acid (compound of Example 2, Method B, Step 1; 1 g, 2.44 mmol) was dissolved in dichloromethane (10 mL) and oxalyl chloride (0.31 mL, 3.66 mmol) was added at room temperature in presence of catalytic amount of DMF. The resulting mixture was stirred at room temperature for 3 h followed by evaporation of dichloromethane to afford the acid chloride. The crude acid chloride and N-hydroxy-propionamidine (0.27 g, 3.17 mmol) were dissolved in 3:1 xylene/pyridine (15 mL; 5 mL) followed by reflux at 130° C. to 140° C. After 4 h, pyridine and xylene were evaporated and the resulting reaction mixture was cooled to room temperature. The resulting mixture was extracted with ethyl acetate (10 mL) and saturated sodium bicarbonate solution (10 mL). The organic phase obtained was dried over anhydrous sodium sulphate and concentrated to obtain a crude product, which was purified by column chromatography (silica gel, 0.5% ethyl acetate in petroleum ether) to afford the title compound.

Yield: 0.370 g (33.03%); $^1$H NMR (CDCl$_3$, 300 MHz): δ 7.66 (d, 1H), 7.06 (m, 2H), 6.84 (d, 1H), 6.77 (d, 1H), 2.78 (q, 2H), 1.36 (t, 3H), 0.99 (s, 9H), 0.98 (s, 9H), 0.227 (s, 6H), 0.220 (s, 6H); MS (ES+): 461 (M+1).

Step 3: Preparation of 4-[2-(3-Ethyl-[1,2,4]oxadiazol-5-yl)-vinyl]-benzene-1,2-diol {2-[3,4-Bis-(tert-butyl-dimethyl-silanyloxy)-phenyl]-vinyl}-3-ethyl-[1,2,4]oxadiazole (compound of Example 2, Method B, Step 2; 0.35 g, 0.75 mmol) was dissolved in THF (10 mL) followed by addition of 1 M solution of TBAF (tetra butyl ammonium fluoride) in THF (0.77 mL, 2.25 mmol) at room temperature over a period of 5 min. After stirring at room temperature for 3 h, the solvent was evaporated and the reaction mixture was allowed to cool to room temperature. The reaction mixture was diluted with water (5 mL) and stirred for 10 min followed by extraction with ethyl acetate (2×10 mL). The combined organic layers were washed with water (2×10 mL) and brine (10 mL). The organic phase obtained was dried over anhydrous sodium sulfate and concentrated to obtain a crude product, which was purified by column chromatography (silica gel, 0.5% methanol in chloroform) to afford the title compound.

Yield: 0.030 g (17.04%); $^1$H NMR (CD$_3$OD, 300 MHz): δ 7.67 (d, 1H), 7.11 (d, 1H), 7.02 (dd, 1H), 6.83 (d, 1H), 6.80 (d, 2H), 2.74 (q, 2H), 1.32 (t, 3H); MS (ES−): 231 (M−1).

EXAMPLE 3

4-[2-(3-Propyl-[1,2,4]oxadiazol-5-yl)-vinyl]-benzene-1,2-diol

Method A

Step 1: Preparation of 5-[2-(3,4-Dimethoxy-phenyl)-vinyl]-3-propyl-[1,2,4]oxadiazole 3-(3,4-Dimethoxy-phenyl)-acrylic acid (compound of Example 2, Method A, Step 1; 3.5 g, 16.80 mmol) was dissolved in dry DMF (35 mL). 1,1'-Carbonyldiimidazole (CDI) (3.0 g, 18.48 mmol) was added and the reaction mixture was stirred at room temperature. At the end of 3 h, N-hydroxybutyramidine (1.88 g, 18.48 mmol) was added and the reaction mixture was stirred at room temperature for 8 h. After completion of the reaction, additional CDI (2.99 g, 18.48 mmol) was added and the reaction mixture was refluxed at 110° C. to 120° C. for 7 h to effect cyclodehydration. DMF was evaporated and the residue obtained was cooled to room temperature followed by addition of water (20 mL). The resulting mixture was extracted with ethyl acetate (3×15 mL). The combined organic layers were washed with water (2×10 mL) and brine (10 mL). The organic phase obtained was dried over anhydrous sodium sulfate and concentrated to afford the title compound.

Yield: 1.4 g (30.36%); $^1$H NMR (CD$_3$OD, 300 MHz): δ 7.74 (d, 1H), 7.29 (d, 1H), 7.22 (dd, 1H), 7.0 (m, 2H), 3.88 (s, 3H), 3.85 (s, 3H), 2.69 (t, 2H), 1.78 (m, 2H), 1.00 (t, 3H); MS (ES+): 275 (M+1).

Step 2: Preparation of 4-[2-(3-Propyl-[1,2,4]oxadiazol-5-yl)-vinyl]-benzene-1,2-diol 5-[2-(3,4-Dimethoxy-phenyl)-vinyl]-3-propyl-[1,2,4] oxadiazole (compound of Example 3, Method A, Step 1; 1.28 g, 4.66 mmol) was dissolved in dichloromethane (15 mL) and cooled to −78° C. A solution of boron tribromide (4.42 mL, 4.66 mmol) in dichloromethane (5 mL), which was cooled to 0° C., was added slowly over a period of 25 min. After 2 h, the reaction mixture was allowed to warm to room temperature (25° C.) and stirred for 2 h. At the end of the reaction, the mixture was quenched by dropwise addition of methanol (15 mL) at 0° C. and stirred for 20 min at room temperature. The solvent was evaporated and the residue obtained was redissolved in 10% methanol in chloroform at 0° C. and stirred with solid sodium carbonate to obtain pH ~8. The solvent was evaporated and the crude product obtained was purified by column chromatography (silica gel, 0.5% methanol in chloroform) to afford the title compound.

Yield: 0.25 g (21.92%); $^1$H NMR (CD$_3$OD, 300 MHz): δ 7.67 (d, 1H), 7.11 (d, 1H), 7.02 (dd, 1H), 6.83 (d, 1H), 6.80 (d, 1H), 2.69 (t, 2H), 1.78 (m, 2H), 0.99 (t, 3H); MS (ES−): 245 (M−1).

Method B

Step 1: Preparation of 5-{2-[3,4-Bis-(tert-butyl-dimethyl-silanyloxy)-phenyl]-vinyl}-3-propyl-[1,2,4]oxadiazole 3-[3,4-Bis-(tert-butyl-dimethyl-silanyloxy)-phenyl]-acrylic acid (compound of Example 2, Method B, Step 1; 122 g, 298.51 mmol) was dissolved in dichloromethane (900 mL) followed by a catalytic amount of DMF and oxalyl chloride (38.60 mL, 447.76 mmol). The resulting mixture was stirred at room temperature for 4 h followed by evaporation of dichloromethane to afford the acid chloride. The crude acid chloride and N-hydroxy-butyramidine (42.68 g, 417.91 mmol) were dissolved in 2:1 toluene:pyridine (800 mL:400 mL) followed by heating at 110° C. to 120° C. After heating for about 16-18 h, pyridine and toluene were evaporated and the reaction mixture was cooled to room temperature. The reaction mixture was diluted with water (300 mL) and stirred for 10 min. The aqueous layer was extracted with ethyl acetate (3×250 mL). The combined organic layers were washed with water (2×10 mL) and brine (10 mL). The organic phase obtained was dried over anhydrous sodium sulfate and concentrated to obtain a crude product, which was purified by column chromatography (silica gel, 0.5% ethyl acetate in petroleum ether) to afford the title compound.

Yield: 38 g (26.81%); $^1$H NMR (CDCl$_3$, 300 MHz): δ 7.62 (d, 1H), 7.02 (m, 2H), 6.81 (d, 1H), 6.73 (d, 1H), 2.69 (t, 2H), 1.77 (m, 2H), 0.98 (t, 9H), 0.97 (s, 12H), 0.20 (s, 6H), 0.19 (s, 6H); MS (ES+): 475 (M+1).

Step 2: Preparation of 4-[2-(3-Propyl-[1,2,4]oxadiazol-5-yl)-vinyl]-benzene-1,2-diol 5-{2-[3,4-Bis-(tert-butyl-dimethyl-silanyloxy)-phenyl]-vinyl}-3-propyl-[1,2,4]oxadiazole (compound of Example 3, Method B, Step 1; 38 g, 80.03 mmol) was dissolved in THF (300 mL) followed by addition of 1 M solution of TBAF in THF (139 mL, 480.18 mmol) over a period of 10 min. After stirring at room temperature for 3 h, the solvent was evaporated and the reaction mixture was allowed to cool to room temperature. The reaction mixture was diluted with water (100 mL) and stirred for 10 min followed by extraction with ethyl acetate (3×50 mL). The combined organic layers were washed with water (2×50 mL) and brine (50 mL). The organic phase obtained was dried over anhydrous sodium sulfate and concentrated to obtain a crude product, which was purified by column chromatography (silica gel, 1.0% methanol in chloroform) to afford the title compound.

Yield: 9.5 g (48.22%); $^1$H NMR (CD$_3$OD, 300 MHz): δ 9.38 (bs, 2H), 7.62 (d, 1H), 7.12 (s, 1H), 7.07 (d, 1H), 6.91 (d, 1H), 6.77 (d, 1H), 2.64 (t, 2H), 1.68 (m, 2H), 0.91 (t, 3H); MS (ES+): 247 (M+1).

Method C

4-[2-(3-Propyl-[1,2,4]oxadiazol-5-yl)-vinyl]-benzene-1,2-diol

A solution of N-hydroxy-butyramidine (0.24 g, 2.34 mmol) in tetrahydrofuran (5 mL) was added slowly into the suspension of 60% sodium hydride (0.14 g, 3.5 mmol) in dry tetrahydrofuran (5 mL) under nitrogen atmosphere at 0° C. to 10° C. The mixture was stirred for 30 min at room temperature. 3-[3,4-Bis-(tert-butyl-dimethyl-silanyloxy)-phenyl]-acrylic acid methyl ester (compound of Example 1, Step 1; 0.5 g, 1.18 mmol) in dry tetrahydrofuran (5 mL) was added into the reaction mixture and heated at 60° C. for 8 h. The reaction mixture was cooled at 0° C. and quenched with methanol (2 mL) to destroy excess sodium hydride. The reaction mixture was extracted with ethyl acetate (2×10 mL) and the combined organic layers were washed with water (2×10 mL) followed by brine (10 mL). The organic phase obtained was dried over anhydrous sodium sulphate and concentrated to dryness. The crude product obtained was purified by column chromatography (silica gel, chloroform-methanol) to afford the title compound.

Yield: 0.12 g (41.38%); $^1$HNMR (CD$_3$OD, 300 MHz): δ 7.68 (d, 1H), 7.11 (bs, 1H), 7.01 (d, 1H), 6.8 (m, 2H), 2.69 (t, 2H), 1.77 (q, 2H), 1.0 (t, 3H).

EXAMPLE 4

4-[2-(3-Benzyl-[1,2,4]oxadiazol-5-yl)-vinyl]-benzene-1,2-diol

Method A

Step 1: Preparation of 3-Benzyl-5-[2-(3,4-dimethoxy-phenyl)-vinyl]-[1,2,4]oxadiazole 3-(3,4-Dimethoxy-phenyl)-acrylic acid (compound of Example 2, Method A, Step 1; 2.0 g, 9.6 mmol) was dissolved in DMF (20 mL) to which 1,1'-carbonyldiimidazole (CDI) (1.71 g, 10.56 mmol) was added and the reaction mixture was stirred at room temperature. At the end of 3 h, N-hydroxy-2-phenyl-acetamidine (1.58 g, 10.56 mmol) was added and the reaction mixture was stirred at room temperature for 8 h. After the completion of the reaction, additional CD (1.71 g, 10.56 mmol) was added and the reaction mixture was refluxed at 110° C. to 120° C. for 8 h to effect cyclodehydration. DMF was evaporated and the residue obtained was cooled to room temperature followed by addition of water (15 mL). The resulting mixture was extracted with ethyl acetate (3×10 mL). The combined organic layers were washed with water (2×10 mL) and brine (10 mL). The organic phase obtained was dried over anhydrous sodium sulfate and concentrated to afford the title compound.

Yield: 12 g (38.83%); NMR (CD$_3$OD, 300 MHz): δ 7.75 (d, 1H), 7.33 (m, 4H), 7.27 (m, 3H), 7.00 (m, 2H), 4.08 (s, 2H), 3.88 (s, 6H); MS (ES+): 345 (M+Na).

Step 2: Preparation of 4-[2-(3-Benzyl-[1,2,4]oxadiazol-5-yl)-vinyl]-benzene-1,2-diol 3-Benzyl-5-[2-(3,4-dimethoxy-phenyl)-vinyl-]-[1,2,4] oxadiazole (compound of Example 4, Method A, Step 1; 0.180 g, 0.55 mmol) was dissolved in dichloromethane (7 mL) and cooled to −78° C. A solution of boron tribromide (0.41 mL, 4.40 mmol) in dichloromethane (4 mL), which was cooled to 0° C., was added slowly over a period of 15 min. After 3 h, the reaction mixture was warmed to room temperature and stirred for 3 h. After completion of the reaction, the mixture was quenched by dropwise addition of methanol (15 mL) at 0° C. and stirred for 20 min at room temperature. The solvent was evaporated and the residue obtained was redissolved in 10% methanol in chloroform at 0° C., followed by stirring with solid sodium carbonate to maintain pH ~8. The solvent was evaporated and the crude product obtained was purified by column chromatography (silica gel, 0.5% methanol in chloroform) to afford the title compound.

Yield: 0.05 g (30.48%); $^1$H NMR (CD$_3$OD, 300 MHz): δ 7.66 (d, 1H), 7.31 (m, 4H), 7.24 (m, 1H), 7.09 (d, 1H), 7.00 (dd, 1H), 6.81 (d, 1H), 6.79 (d, 1H), 4.06 (s, 2H); MS (ES−): 293 (M−1).

Method B

Step 1: Preparation of 3-Benzyl-5-{2-[3,4-bis-(tert-butyl-dimethyl-silanyloxy)-phenyl]-vinyl}-[1,2,4] oxadiazole 3-[3,4-Bis-(tert-butyl-dimethyl-silanyloxy)-phenyl]-acrylic acid (compound of Example 2, Method B, Step 1; 17 g, 41.59 mmol) was dissolved in dichloromethane (150 mL) and oxalyl chloride (5.38 mL, 62.38 mmol) was added at room temperature in presence of catalytic amount of DMF. The resulting mixture was stirred at room temperature for 3 h followed by evaporation of dichloromethane to afford the acid chloride. The crude acid chloride and N-hydroxy-2-phenyl-acetamidine (7.49 g, 49.90 mmol) were dissolved in 2:1 xylene:pyridine (100 mL: 50 mL) followed by reflux at 130° C. to 140° C. After heating for about 16-18 h, pyridine and xylene were evaporated and the resulting mixture was cooled to room temperature. The resulting mixture was diluted with water (50 mL) and stirred for 10 min. The aqueous layer was extracted with ethyl acetate (3×35 mL). The combined organic layers were washed with water (2×50 mL) and brine (50 mL). The organic phase obtained was dried over anhydrous sodium sulfate and concentrated to obtain a crude product, which was purified by column chromatography (silica gel, 0.5% ethyl acetate in petroleum ether) to afford the title compound.

Yield: 4.65 g (21.38%); $^1$H NMR (CDCl$_3$, 300 MHz): δ 7.66 (d, 1H), 7.37 (m, 3H), 7.30 (m, 2H), 7.05 (m, 2H), 6.85 (d, 1H), 6.77 (d, 1H), 4.11 (s, 2H), 1.01 (s, 9H), 1.00 (s, 9H), 0.24 (s, 6H), 0.23 (s, 6H); MS (ES+): 523 (M+1).

Step 2: Preparation of 4-[2-(3-Benzyl-[1,2,4]oxadiazol-5-yl)-vinyl]benzene-1,2-diol 3-Benzyl-5-{2-[3,4-bis-(tert-butyl-dimethyl-silanyloxy)-phenyl]-vinyl}-[1,2,4]oxadiazole (compound of Example 4, Method B, Step 1) (4.60 g, 8.79 mmol) was dissolved in THF (30 mL) and cooled to 5° C. This was followed by addition of 1 M solution of TBAF in THF (12.72 mL, 43.95 mL) over a period of 15 min and allowed to warm to room temperature. After 3 h stirring at room temperature, the solvent was evaporated and the reaction mixture was allowed to cool to room temperature. The reaction mixture was diluted with water (30 mL) and stirred for 10 min followed by extraction with ethyl acetate (3×20 mL). The combined organic layers were washed with water (2×10 mL) and brine (10 mL). The organic phase obtained was dried over anhydrous sodium sulfate and concentrated to obtain a crude product, which was purified by column chromatography (silica gel, 0.5% methanol in chloroform) to afford the title compound.

Yield: 1.62 g (62.79%); $^1$H NMR (CD$_3$OD, 300 MHz): δ 7.68 (d, 1H), 7.33 (d, 4H), 7.27 (m, 1H), 7.11 (d, 1H), 7.02 (dd, 1H), 6.82 (m, 2H), 4.07 (s, 2H); MS (ES−): 293 (M−1).

EXAMPLE 5

4-Methoxy-3-nitro-benzaldehyde

4-Methoxy-benzaldehyde (1 g, 7.34 mmol) was added to a mixture of ammonium nitrate (0.58 g, 7.34 mmol) and trifluoroacetic anhydride (3.56 mL, 25.69 mmol), which was cooled to 0° C. The reaction mixture was stirred at 0° C. for 15 min and then allowed to stir at room temperature for about 7 h. Ice was added and stirred for 30 min. The solid obtained was filtered, washed with cold water (3×5 mL) and dried.

Yield: 1.100 (82.70%); $^1$H NMR (DMSO-d$_6$, 300 MHz): δ 9.93 (s, 1H), 8.40 (d, 1H), 8.17 (dd, 1H), 7.55 (d, 1H), 4.02 (s, 3H).

EXAMPLE 6

3-(4-Methoxy-3-nitro-phenyl)-acrylic acid 4-methoxy-3-nitro-benzaldehyde (compound of Example 5; 1.05 g, 5.79 mmol) and malonic acid (1.32 g, 1.27 mmol) were dissolved in pyridine (20 mL) under stirring and piperidine (1 mL) was added to the pyridine solution. The reaction mixture was heated at 75° C. to 80° C. for 3 h, after which the temperature was further increased to 120° C. and maintained at this temperature for 6 h. At the end of the reaction, pyridine was evaporated, followed by addition of aqueous HCl (1:1) to obtain pH ~4. The solid obtained was filtered, washed with cold water and dried.

Yield: 1.0 g (83.01%); $^1$H NMR (DMSO-d$_6$, 300 MHz): δ 12.37 (bs, 1H), 8.22 (d, 1H), 7.99 (dd, 1H), 7.57 (d, 1H), 7.37 (d, 1H), 6.54 (d, 1H), 3.94 (s, 3H); MS (ES−): 222 (M−1).

EXAMPLE 7

5-[2-(4-Methoxy-3-nitro-phenyl)-vinyl]-3-propyl-[1,2,4]oxadiazole 3-(4-Methoxy-3-nitro-phenyl)-acrylic acid (compound of Example 6; 0.95 g, 4.25 mmol) was dissolved in DMF (15 mL) to which CDI (0.82 g, 5.10 mmol) was added and the reaction mixture was stirred at room temperature. After 45 min, N-hydroxy-butyramidine (0.52 g, 5.10 mmol) was added. The reaction mixture was stirred at room temperature for about 16-18 h. After completion of the reaction, additional CDI (0.82 g, 5.10 mmol) was added and the reaction mixture was refluxed at 110° C. to 120° C. for 6 h to effect cyclodehydration. DMF was evaporated and the reaction mixture was cooled to room temperature. Water (10 mL) was added to the reaction mixture followed by extraction with ethyl acetate (2×10 mL). The combined organic layers were washed with water (2×10 mL) and brine (10 mL). The organic phase obtained was dried over anhydrous sodium sulfate and concentrated to obtain a crude product, which was purified by column chromatography (silica gel, 0.25% ethyl acetate in petroleum ether) to afford the title compound.

Yield: 0.150 g (12.19%); $^1$H NMR (CD$_3$OD, 300 MHz): δ 8.14 (d, 1H), 7.92 (dd, 1H), 7.77 (d, 1H), 7.34 (d, 1H), 7.11 (d, 1H), 3.99 (s, 3H), 2.71 (t, 2H), 1.77 (m, 2H), 0.99 (t, 3H); MS (ES+): 290 (M+1).

EXAMPLE 8

2-Methoxy-5-[2-(3-propyl-[1,2,4]oxadiazol-5-yl)-vinyl]-phenylamine

5-[2-(4-Methoxy-3-nitro-phenyl)-vinyl]-3-propyl-[1,2,4]oxadiazole (compound of Example 7; 0.140 g, 0.48 mmol) was dissolved in ethyl acetate (10 mL) to which stannous chloride (0.43 g, 1.93 mmol) was added and the reaction mixture was stirred at room temperature. After 8 h, additional stannous chloride (0.32 g, 1.44 mmol) was added and the reaction mixture was stirred at room temperature for about 16-18 h. The pH of the reaction mixture was adjusted to 11 by addition of 10% sodium hydroxide and extracted with ethyl acetate (2×5 mL). The combined organic layers were washed with water (2×10 mL) and brine (10 mL). The organic phase obtained was dried over anhydrous sodium sulfate and concentrated to obtain a crude product, which was purified by column chromatography (silica gel, 0.5% methanol in chloroform) to afford the title compound.

Yield: 0.100 g (80%); $^1$H NMR (CD$_3$OD, 300 MHz): δ 7.68 (d, 1H), 7.1 (d, 1H), 6.99 (dd, 1H), 6.86 (m, 2H), 3.89 (s, 3H), 2.69 (t, 2H), 1.77 (m, 2H), 1.00 (t, 3H); MS (ES+): 260 (M+1).

EXAMPLE 9

N-{2-Methoxy-5-[2-(3-propyl-[1,2,4]oxadiazol-5-yl)-vinyl]-phenyl}-methane sulfonamide 2-Methoxy-5-[2-(3-propyl-[1,2,4]oxadiazol-5-yl)-vinyl]-phenylamine (compound of Example 8; 0.08 g, 3.08 mmol) was dissolved in dichloromethane (10 mL) followed by addition of pyridine (0.047 mL, 0.60 mmol) and methanesulfonyl chloride (0.034 mL, 0.45 mmol) at room temperature. After stirring for 8 h, dichloromethane was evaporated and the reaction mixture was cooled to room temperature. The crude residue obtained was purified by column chromatography (silica gel, petroleum ether) to afford the title compound.

Yield: 0.08 g (76.92%); $^1$H NMR (CD$_3$OD, 500 MHz): δ 9.29 (m, 2H), 9.08 (dd, 1H), 8.67 (d, 1H), 8.52 (d, 1H), 5.51 (s, 3H), 4.50 (s, 3H), 4.25 (t, 2H), 3.35 (m, 2H), 2.55 (t, 3H).

EXAMPLE 10

N-{2-Hydroxy-5-[2-(3-propyl-[1,2,4]oxadiazol-5-yl)-vinyl]-phenyl}-methanesulfonamide N-{2-Methoxy-5-[2-(3-propyl-[1,2,4]oxadiazol-5-yl)-vinyl]-phenyl}-methane sulfonamide (compound of Example 9; 0.08 g, 0.23 mmol) was dissolved in dichloromethane (7 mL) and cooled to −78° C. A solution of boron tribromide in dichloromethane (0.15 mL, 1.61 mmol) was cooled to −78° C. and slowly added to the reaction mixture. After 1.5 h, the reaction mixture was warmed to room temperature and stirred for 3 h. At the end of 3 h, the mixture was quenched by dropwise addition of methanol (5 mL) at 0° C. and stirred for 20 min at room temperature. The solvent was evaporated, and the residue was redissolved in a mixture of 10% methanol in chloroform at 0° C. Solid sodium carbonate was added to this solution to adjust pH to 8. The solvent was evaporated and the crude product obtained was purified by column chromatography (silica gel, 0.5% methanol in chloroform) to afford the title compound.

Yield: 0.05 g (65.78%); $^1$H NMR (CD$_3$OD, 300 MHz): δ 7.69 (d, 1H), 7.63 (d, 1H), 7.38 (dd, 1H), 6.88 (m, 2H), 2.93 (s, 3H), 2.66 (t, 2H), 1.74 (m, 2H), 0.96 (t, 3H).

EXAMPLE 11

2-Nitro-4-[2-(5-propyl-[1,2,4]oxadiazol-3-yl)-vinyl]-phenol (minor) and 3-[2-(4-Methoxy-3-nitro-phenyl)-vinyl]-5-propyl-[1,2,4]oxadiazole (major; compound of Example 7)

3-(4-Methoxy-3-nitro-phenyl)-acrylic acid (compound of Example 6; 1 g, 4.48 mmol), DCC (1.01 g, 4.92 mmol) and HOBt (0.50 g, 4.92 mmol) were dissolved in DMF (15 mL) and stirred at room temperature for 40 min. N-Hydroxybutyramidine was added to the reaction mixture at room temperature and the resulting slurry was stirred at 135° C. to 140° C. After 18 h, DMF was evaporated and the reaction mixture was cooled to room temperature. The mixture was diluted with water (7 mL) followed by extraction with ethyl acetate (3×5 mL). The combined organic layers were washed with water (2×10 mL) and brine (10 mL). The organic phase obtained was dried over anhydrous sodium sulfate and concentrated to obtain a crude product, which was purified by column chromatography (silica gel, 0.5% ethyl acetate in petroleum ether) to afford 3-[2-(4-methoxy-3-nitro-phenyl)-vinyl]-5-propyl-[1,2,4]oxadiazole (compound of Example 7) as the major product and 2-nitro-4-[2-(5-propyl-[1,2,4]oxadiazol-3-yl)-vinyl]phenol (compound of Example 11) as the minor product.

2-Nitro-4-[2-(5-propyl-[1,2,4]oxadiazol-3-yl)-vinyl]-phenol

Yield: 0.350 g (28.18%); $^1$H NMR (CD$_3$OD): δ 8.35 (d, 1H), 7.98 (dd, 1H), 7.80 (d, 1H), 7.21 (d, 1H), 7.13 (d, 1H), 2.71 (t, 2H), 1.78 (m, 2H), 1.00 (t, 3H).

3-[2-(4-Methoxy-3-nitro-phenyl)-vinyl]-5-propyl-[1,2,4]oxadiazole

Yield: 0.250 g (19.23%); $^1$H NMR (CD$_3$OD, 300 MHz): δ 8.14 (d, 1H), 7.92 (dd, 1H), 7.77 (d, 1H), 7.34 (d, 1H), 7.11 (d, 1H), 3.99 (s, 3H), 2.71 (t, 2H), 1.82 (m, 2H), 1.15 (t, 3H).

EXAMPLE 12

2-Amino-4-[2-(5-propyl-[1,2,4]oxadiazol-3-yl)-vinyl]-phenol

2-Nitro-4-[2-(5-propyl-[1,2,4]oxadiazol-3-yl)-vinyl]-phenol (compound of Example 11; 0.2 g, 0.72 mmol) was dissolved in ethyl acetate (5 mL) to which stannous chloride was added and the reaction mixture was stirred at room temperature for 12 h. The reaction mixture was cooled to 0° C. followed by addition of aqueous sodium hydroxide solution to adjust pH to 10. The reaction mixture was extracted with ethyl acetate (2×5 mL). The combined organic layers were washed with water (2×10 mL) and brine (10 mL). The organic phase obtained was dried over anhydrous sodium sulfate and concentrated to obtain a crude product, which was purified by column chromatography (silica gel, 0.5 methanol in chloroform) to afford the title compound.

Yield: 0.130 g (73.86%); $^1$H NMR (CD$_3$OD, 300 MHz): δ 7.65 (d, 1H), 7.08 (d, 1H), 6.89 (dd, 1H), 6.81 (d, 1H), 6.72 (d, 1H), 2.68 (t, 2H), 1.78 (m, 2H), 0.99 (t, 3H).

EXAMPLE 13

4-Oxo-piperidine-1-carboxylic acid tert-butyl ester

Aqueous 2N sodium hydroxide (81 mL, 162.7 mmol) was added slowly at 0° C. into a solution of 4-piperidonehydrochloride (10 g, 65 mmol) in THF (50 mL) and stirred for 15 min. t-Butoxycarbamate (17.04 g, 78 mmol) was added slowly into the reaction mixture and stirred for 4 h. The reaction mixture was concentrated to dryness, diluted with ethyl acetate (2×50 mL) and washed with water (2×50 mL) and brine (50 mL). The organic phase obtained was dried over anhydrous sodium sulphate and concentrated to afford the title compound.

Yield: 12.7 g (98.44%); $^1$H NMR (CDCl$_3$, 300 MHz): δ 3.68 (t, 4H), 2.40 (t, 4H), 1.45 (s, 9H); MS (ES+); 200 (M+1).

EXAMPLE 14

4-Cyanomethylene-piperidine-1-carboxylic acid tert-butyl ester

A mixture of 4-oxo-piperidine-1-carboxylic acid tert-butyl ester (compound of Example 13; 13.5 g, 67 mmol), anhydrous potassium carbonate (11.22 g, 81 mmol) and cyanomethyl phosphonic acid diethylester (15.6 g, 88 mmol) in THF (70 mL) was heated at reflux for 12 h. THF was evaporated and the residue was dissolved in chloroform (2×50 mL). The resulting solution was washed with water (2×50 mL) and brine (50 mL). The organic phase obtained was dried over anhydrous sodium sulphate and concentrated to afford the title compound.

Yield: 7.9 g (50.64%); $^1$H NMR (DMSO-d$_6$, 300 MHz): δ 5.55 (s, 1H), 3.41 (t, 4H), 2.41 (t, 2H), 2.29 (t, 2H), 1.39 (s, 9H); MS (ES+): 223 (M+1).

EXAMPLE 15

4-Cyanomethyl-piperidine-1-carboxylic acid tert-butyl ester

4-Cyanomethylene-piperidine-1-carboxylic acid tert-butyl ester (compound of Example 14; 6.9 g, 31.0 mmol) and Pd/C (0.7 g) in ethanol (150 mL) was maintained under hydrogen atmosphere for 8 h. The reaction mixture was filtered through Celite and the solvent was evaporated to afford the title compound.

Yield: 6.4 g (91.95%); $^1$H NMR (MeOD, 300 MHz): δ 4.06 (m, 2H), 2.74 (m, 2H), 2.41 (d, 2H), 1.86 (m, 1H), 1.77 (m, 2H), 1.42 (s, 9H), 1.21 (m, 2H). MS (ES+): 225 (M+1).

EXAMPLE 16

4-(N-Hydroxycarbamimidoylmethyl)-piperidine-1-carboxylic acid tert-butyl ester

4-Cyanomethyl-piperidine-1-carboxylic acid tert-butyl ester (compound of Example 15; 2.3 g, 10.2 mmol), anhydrous potassium carbonate (2.27 g, 16.4 mmol) and hydroxylamine hydrochloride (2.14 g, 30.8 mmol) in ethanol:water (25:4 mL) was stirred at room temperature for 48 h. The reaction mixture was filtered, solvent evaporated and the residue obtained was purified by column chromatography (silica gel, 8% ethyl acetate in petroleum ether) to afford the title compound.

Yield: 2.14 g (81.36%); $^1$H NMR (MeOD, 300 MHz): δ 4.04 (m, 2H), 2.73 (m, 2H), 1.99 (d, 2H), 1.77 (m, 1H), 1.67 (m, 2H), 1.44 (s, 9H), 1.10 (m, 2H); MS (ES+): 258 (M+1).

EXAMPLE 17

3-(3,4-Dimethoxy-phenyl)-acrylic acid methyl ester 3-(3,4-Dimethoxy-phenyl)-acrylic acid (compound of Example 2 (Step 1); 1.0 g, 4.8 mmol) was dissolved in methanol (10 mL) in the presence of catalytic amount of sulfuric acid. The reaction mixture was stirred at room temperature for 4 h. The reaction mixture was cooled at 5° C. and quenched with saturated sodium carbonate solution (2 mL). The solid obtained was filtered and dried.

Yield: 1.0 g (93.72%); $^1$HNMR (CDCl$_3$, 300 MHz): δ 7.65 (d, 1H), 7.23 (d, 1H), 7.18 (dd, 1H), 6.99 (d, 1H), 6.43 (d, 1H), 3.85 (s, 3H), 3.84 (s, 3H), 3.78 (s, 3H); MS (ES+): 223 (M+1).

EXAMPLE 18

4-{5-[2-(3,4-Dimethoxy-phenyl)-vinyl]-[1,2,4]oxadiazol-3-ylmethyl}-piperidine-1-carboxylic acid tert-butyl ester 4-(N-Hydroxycarbamimidoylmethyl)-piperidine-1-carboxylic acid tert-butyl ester (compound of Example 16; 5.0 g, 22.5 mmol) was added to a suspension of 60% sodium hydride (2.25 g, 56.3 mmol) in dry THF (25 mL) and the reaction mixture was stirred at 25° C. for 0.5 h. 3-(3,4-Dimethoxy-phenyl)-acrylic acid methyl ester (compound of Example 17; 11.57 g, 45 mmol) was added into the reaction mixture and the reaction mixture was refluxed for 12 h. The reaction mixture was quenched with water (30 mL) and the solvent was evaporated. The residue obtained was dissolved in chloroform (50 mL) and washed with water (2×30 mL). The organic phase obtained was dried over anhydrous sodium sulfate and concentrated to afford the title compound.

Yield: 4.9 g (53.48%); MS (ES+): 452.2 (M+Na).

EXAMPLE 19

4-{5-[2-(3,4-Dimethoxy-phenyl)-vinyl]-[1,2,4]oxadiazol-3-ylmethyl}-piperidine

Trifluoroacetic acid (5 mL) was added slowly into a solution of 4-{5-[2-(3,4-dimethoxy-phenyl)-vinyl]-[1,2,4]oxadiazol-3-ylmethyl}-piperidine-1-carboxylic acid tert-butyl ester (compound of Example 18; 4.5 g, 10.4 mmol) in dichloromethane (25 mL) and was stirred at 25° C. for 15 h. The solvent was evaporated and the residue was extracted into chloroform (2×25 mL). The combined organic layers were washed with saturated sodium carbonate solution (2×25 mL) and water (1×25 mL). The organic phase obtained was dried over anhydrous sodium sulphate and concentrated to afford the title compound.

Yield: 3.1 g (89.79%); $^1$H NMR (CDCl$_3$, 300 MHz): δ 7.69 (d, 1H), 7.13 (dd, 1H), 7.06 (d, 1H), 6.86 (d, 1H), 6.80 (d, 1H), 3.91 (s, 3H), 3.90 (s, 3H), 3.21 (m, 2H), 2.70 (m, 5H), 2.01 (m, 1H), 1.81 (m, 2H), 1.44 (m, 2H); MS (ES+): 330 (M+1).

EXAMPLE 20

4-[2-(3-Piperidin-4,1-methyl-[1,2,4]oxadiazol-5-yl)-vinyl]-benzene-1,2-diol

Boron tribromide (0.43 mL, 4.55 mmol) was added dropwise to a cooled solution of 4-{5-[2-(3,4-dimethoxy-phenyl)-vinyl]-[1,2,4]oxadiazol-3-ylmethyl}-piperidine (compound of Example 19; 0.25 g, 035 mmol) in dichloromethane (10 mL) at −78° C. The reaction mixture was allowed to warm to room temperature and stirred for 6 h. The reaction mixture was quenched with methanol (5 mL) and the organic solvent was evaporated. The residue obtained was dissolved in 8% methanolic ammonia (5 mL) and the inorganic solid obtained was removed by filtration. The filtrate was concentrated and purified by column chromatography (silica gel, 3% methanol in chloroform) to afford the title compound.

Yield: 0.050 g (21.86%); MS (ES+): 302 (M+1).

EXAMPLE 21

4-{5-[2-(3,4-Dimethoxy-phenyl)-vinyl]-[1,2,4]oxadiazol-3-ylmethyl}-1-isopropyl-piperidine Isopropyl bromide (0.13 mL, 1.45 mmol) was added slowly into a mixture of 4-{5-[2-(3,4-dimethoxy-phenyl)-vinyl]-[1,2,4]oxadiazol-3-ylmethyl}-piperidine (compound of Example 19; 0.4 g, 1.21 mmol) and anhydrous potassium carbonate (0.25 g, 1.82 mmol) in dry DMF (10 mL). The reaction mixture was heated at 55° C. to 60° C. for 4 h. The reaction mixture was cooled to room temperature and ice water (5 mL) was added into it. The solid obtained was filtered and dried.

Yield: 0.175 g (38.88%); $^1$H NMR (CDCl$_3$, 300 MHz): δ 7.70 (d, 1H), 7.14 (dd, 1H), 7.08 (d, 1H), 6.89 (d, 1H), 6.83 (d, 1H), 3.92 (s, 3H), 3.91 (s, 3H), 3.07 (m, 2H), 2.99 (m, 1H), 2.70 (d, 2H), 2.35 (m, 2H), 1.91 (m, 3H), 1.58 (m, 2H), 1.14 (d, 6H); MS (ES+): 372 (M+1).

EXAMPLE 22

4-{2-[3-(1-Isopropyl-piperidin-4-ylmethyl)-[1,2,4]oxadiazol-5-yl]-vinyl}-benzene-1,2-diol Boron tribromide (0.229 mL, 2.42 mmol) was added dropwise to a cooled solution of 4-{5-[2-(3,4-Dimethoxy-phenyl)-vinyl]-[1,2,4]oxadiazol-3-ylmethyl}-1-isopropyl-piperidine (compound of Example 21; 0.15 g, 0.4 mmol) in dichloromethane (5 mL) at −78° C. The reaction mixture was warmed to room temperature and stirred for 6 h. The reaction mixture was quenched with methanol (2 mL) and the organic solvent was evaporated. The residue obtained was dissolved in 8% methanolic ammonia (5 mL) and the inorganic solid obtained was removed by filtration. The filtrate was concentrated and purified by column chromatography (silica gel, 3% methanol in chloroform) to afford the title compound.

Yield: 0.019 g (13.69%); MS (ES+): 344 (M+1).

EXAMPLE 23

[2-(4-{5-[2-(3,4-Dimethoxy-phenyl)-vinyl]-[1,2,4]oxadiazol-3-ylmethyl}-piperidin-1-yl)-ethyl]-dimethyl-amine N,N-Dimethylethyl chloride (0.21 g, 1.45 mmol) was added slowly into a solution of 4-{5-[2-(3,4-dimethoxy-phenyl)-vinyl]-[1,2,4]oxadiazol-3-ylmethyl}-piperidine (compound of Example 19; 0.4 g, 1.21 mmol) and anhydrous potassium carbonate (0.37 g, 1.82 mmol) in dry DMF (10 mL). The mixture was heated at 55° C. to 60° C. for 4 h. The reaction mixture was cooled to room temperature and ice water (5 mL) was added into it. The solid obtained was filtered and dried to afford the title compound.

Yield: 0.160 g (32.91%); MS (ES+): 401 (M+1).

EXAMPLE 24

4-(2-{3-[1-(2-Dimethylamino-ethyl)-piperidin-4-ylmethyl]-[1,2,4]oxadiazol-5-yl}-vinyl)-benzene-1,2-diol Boron tribromide (0.14 mL, 1.49 mmol) was added dropwise to a cooled solution of [2-(4-{5-[2-(3,4-dimethoxy-phenyl)-vinyl]-[1,2,4]oxadiazol-3-ylmethyl}-piperidin-1-yl)-ethyl]-dimethyl-amine (compound of Example 23; 0.10 g, 0.25 mmol) in dichloromethane (5 mL) at −78° C. The reaction mixture was warmed to room temperature and stirred for 6 h. The reaction mass was quenched with methanol (2 mL) and the organic solvent was evaporated. The residue obtained was dissolved in 8% methanolic ammonia (5 mL) and the inorganic solid obtained was removed by filtration. The filtrate was concentrated and purified by column chromatography (silica gel, 3% methanol in chloroform) to afford the title compound.

Yield: 0.050 g (53.78%); $^1$H NMR (DMSO-d$_6$, 300 MHz): δ 7.60 (d, 1H), 7.11 (d, 1H), 7.07 (dd, 1H), 6.91 (d, 1H), 6.75 (d, 1H), 2.84 (m, 2H), 2.58 (d, 2H), 2.35 (s, 4H), 2.14 (s, 6H), 1.95 (m, 3H), 1.69 (m, 2H), 1.41 (m, 2H); MS (ES+): 373 (M+1).

EXAMPLE 25

Benzyl-piperidin-4-one

A mixture of 4-piperidone monohydrate hydrochloride (2.5 g, 14.56 mmol) and anhydrous potassium carbonate (7 g, 50.64 mmol) in dry DMF (25 mL) was stirred for 30 min at room temperature. Benzyl bromide (2 mL, 16.82 mmol) was added dropwise into the reaction mixture and heated at 65° C. for 14 h. The reaction mixture was cooled to room temperature, filtered and quenched with ice water (25 mL). The resulting mixture was extracted in ethyl acetate (2×20 mL) and the combined organic layers were washed with water (2×15 mL) followed by brine (20 mL). The organic phase obtained was dried over anhydrous sodium sulphate and evaporated. The crude product obtained was purified by crystallisation using 2% methanol in chloroform to afford the title compound.

Yield: 2.5 g (89.28%); $^1$HNMR (CDCl$_3$, 300 MHz): δ 7.34 (m, 4H), 7.29 (m, 1H), 3.62 (s, 2H), 2.75 (t, 4H), 2.46 (t, 4H).

EXAMPLE 26

1-Benzylpiperidin-4-ylideneacetonitrile

A mixture of diethyl cyanomethylphosphonate (2.06 g, 11.62 mmol) and anhydrous potassium carbonate (1.6 g, 11.62 mmol) in dry THF (10 mL) was stirred at room temperature for 15 min and then refluxed for 20 min. After cooling to room temperature, benzyl-piperidin-4-one (compound of Example 25; 2 g, 10.56 mmol) was added and the mixture was heated at reflux for 16 h (~70° C.). The reaction mixture was cooled to room temperature, filtered and quenched with ice water (25 mL). The resulting mixture was extracted with ethyl acetate (2×20 mL) and the combined organic layers were washed with water (2×15 mL) followed by brine (20 mL). The organic phase obtained was dried over anhydrous sodium sulphate and concentrated to obtain a crude product, which was purified by crystallisation using 2% ethyl acetate in hexane to afford the title compound.

Yield: 2.14 g (95.41%); MS (ES+): 213 (M+1).

EXAMPLE 27

2-(1-Benzylpiperidin-4-yl)acetonitrile

To a solution of benzylpiperidin-4-ylideneacetonitrile (compound of Example 26; 1 g, 4.7 mmol) in methanol (50 mL), magnesium turnings (4.58 g, 188.3 mmol) was added at 0° C. The reaction mixture was stirred at 5° C. to 10° C. for 4 h. The magnesium salts were dissolved by addition of concentrated hydrochloric acid, and the mixture was basified with 10N sodium hydroxide solution. The precipitate was filtered and extracted with ethyl acetate (2×20 mL). The combined organic layers were washed with water (2×15 mL) followed by brine (10 mL). The organic phase obtained was dried over anhydrous sodium sulphate and evaporated to afford the title compound.

Yield: 0.82 g (82%); $^1$HNMR (CDCl$_3$, 300 MHz): δ 7.32 (m, 5H), 3.52 (s, 2H), 2.92 (bm, 2H), 2.30 (d, 2H), 2.0 (m, 2H), 1.80 (m, 2H), 1.69 (m, 1H), 1.43 (m, 2H).

EXAMPLE 28

2-(1-Benzyl-piperidin-4-yl)-N-hydroxy-acetamidine

Sodium metal (0.8 g, 34.78 mmol) was dissolved in dry methanol (10 mL) at 0-10° C. and this solution was added slowly into a suspension of hydroxylamine hydrochloride (2.43 g, 34.96 mmol) in methanol (10 mL) at room temperature. The reaction mixture was stirred for 10 min until a clear solution was obtained, 2-(1-Benzylpiperidin-4-yl)acetonitrile (compound of Example 27; 3 g, 13.99 mmol) in dry methanol (20 mL) was added into the resulting reaction mixture and heated at 75° C. for 13 h. The solvent was evaporated at 50° C. to 55° C. and the crude product obtained was purified by column chromatography (silica gel, chloroform-methanol) to afford the title compound.

Yield: 2.3 g (66.66%); $^1$HNMR (CDCl$_3$, 300 MHz): δ 7.30 (d, 4H), 7.24 (m, 1H), 4.5 (s, 2H), 3.52 (s, 2H), 2.88 (d, 2H), 2.03 (d, 2H), 1.97 (t, 2H), 1.70 (d, 2H), 1.55 (m, 1H), 1.36 (m, 2H); MS (ES+): 248 (M+1).

EXAMPLE 29

N-[2-(1-Benzyl-piperidin-4-yl)-hydroxylamino-ethyl]-3-(3,4-dimethoxy-phenyl)-acrylamide A solution of 3,4-dimethoxycinnamic acid (compound of Example 17; 0.484 g, 2.32 mmol) in dichloromethane (10 mL) was converted to its acid chloride using oxalyl chloride (0.3 mL, 3.49 mmol). The organic solvent was evaporated. The resulting acid chloride was redissolved in dry pyridine (5 mL) and 2-(1-benzyl-piperidin-4-yl)-N-hydroxy-acetamidine (compound of Example 28; 0.6 g, 2.55 mmol) was added to the acid chloride solution. The reaction mixture was stirred at 25° C. for 12 h, pyridine was evaporated and the residue was dissolved in ethyl acetate (2×10 mL). The organic layer was washed with water (2×5 mL), dried over anhydrous sodium sulphate and concentrated to obtain a crude product, which was purified by column chromatography (silica gel, 2% methanol in chloroform) to afford the title compound.

Yield: 0.120 g (21.60%); $^1$HNMR (CDCl$_3$, 300 MHz): δ 7.72 (d, 1H, 7.29 (m, 4H), 7.23 (m, 1H), 7.11 (dd, 1H), 7.04 (d, 1H), 6.86 (d, 1H), 6.38 (d, 1H), 4.70 (s, 1H), 3.90 (s, 6H), 3.48 (s, 2H), 2.87 (m, 2H), 2.21 (d, 2H), 1.95 (t, 2H), 1.74 (d, 2H), 1.64 (m, 1H), 1.37 (m, 2H); MS (ES+): 436 (M−1).

EXAMPLE 30

1-Benzyl-4-{5-[2-(3,4-dimethoxy-phenyl)-vinyl]-[1,2,4]oxadiazol-3-ylmethyl}-piperidine Sodium acetate (0.082 g, 1.005 mmol) was dissolved in water and added to a stirred solution of N-[2-(1-benzyl-piperidin-4-yl)-1-hydroxylamino-ethyl]-3-(3,4-dimethoxy-phenyl)-acrylamide (compound of Example 29; 0.4 g, 0.914 mmol) in ethanol (3 mL) and water. The resulting mixture was heated at 80° C. to 85° C. for 5 h. Ethanol was evaporated and the residue obtained was dissolved in chloroform (3 mL) and the undissolved solid was filtered. The filtrate was evaporated to obtain a crude product, which was purified by column chromatography (silica gel, chloroform-methanol) to afford the title compound.

Yield: 0.06 g (15.64%); $^1$HNMR (CDCl$_3$, 300 MHz): δ 7.72 (d, 1H), 7.30 (m, 4H), 7.23 (m, 1H), 7.12 (dd, 1H), 7.09 (d, 1H), 6.89 (d, 1H), 6.81 (d, 1H), 3.93 (s, 6H), 3.50 (s, 2H), 2.89 (m, 2H), 2.68 (d, 2H), 1.99 (t, 2H), 1.85 (m, 1H), 1.70 (m, 2H), 1.36 (m, 2H); MS (ES+): 420 (M+1).

EXAMPLE 31

4-{2-[3-(1-Benzyl-piperidin-4-ylmethyl)-[1,2,4]oxadiazol-5-yl]-vinyl}-benzene-1,2-diol Boron tribromide (0.056 mL, 0,595 mmol) was added drop wise to a cooled solution of 1-benzyl-4-{5-[2-(3,4-dimethoxy-phenyl)-vinyl]-[1,2,4]oxadiazol-3-ylmethyl}-piperidine (compound of Example 30; 0.05 g, 0.12 mol) in dichloromethane (3 mL) at −78° C. The reaction mixture was warmed to room temperature and stirred for 6 h. The reaction mixture was quenched with methanol (2 mL) and the organic solvent was evaporated. The residue was suspended in methanolic ammonia (2 mL) and the undissolved solid was filtered. The filtrate was evaporated to obtain a crude product, which was purified by column chromatography (silica gel, 3% methanol in chloroform) to afford the title compound.

Yield: 0.015 g (32.15%); $^1$HNMR (CDCl$_3$, 300 MHz); 67.67 (d, 1H), 7.46 (m, 5H), 7.22 (dd, 1H), 7.14 (d, 1H), 7.01 (m, 1H), 6.82 (d, 1H), 3.51 (m, 2H), 3.04 (m, 2H), 2.75 (m, 2H), 2.27 (t, 2H), 2.01 (m, 2H), 1.60 (m, 3H); MS (ES+): 392 (M+1).

EXAMPLE 32

N-hydroxy-decanimidamide

To a solution of 0.68 g (9.76 mmol) of hydroxylamine hydrochloride in 11 mL of isopropyl alcohol, 1206 g (14.3 mmol) of sodium bicarbonate was added. The resulting mixture was stirred at 25° C. to 30° C. for 10-15 min. 1.0 g (6.52 mmol) of decanitrile was added and stirred at 80° C. to 85° C. for 3-4 h. After the reaction was complete, the reaction mixture was cooled to 25° C. to 30° C., filtered and the residue was washed with 2 mL of isopropyl alcohol. The filtrate was collected and distilled out completely to yield a residue which was washed with toluene to yield the title compound.

Yield: 1.1 g (90%).

EXAMPLE 33

5-[2-(3,4-Dimethoxy-phenyl)-vinyl]-3-nonyl-[1,2,4]oxadiazole

To a solution of 0.547 g (2.6 mmol) of 3-(3,4-dimethoxyphenyl)-acrylic acid (compound of Example 2; Step 1) in 8 mL of toluene, 0.46 g (2.8 mmol) of 1,1-carbonyldiimidazole was added in portions at 25° C. to 30° C. under inert atmosphere. To the thick mixture, 1 mL of toluene was added and the resulting mixture was stirred at 25° C. to 30° C. for 60 to 90 min. A solution of N-hydroxy-decanimidamide (compound of Example 32; 1.0 g, 5.3 mmol) in 3 mL of toluene was added to the above reaction mixture at 25° C. to 30° C. The reaction mixture was stirred at 25° C. to 30° C. under nitrogen for 12-14 h and further at 100° C. to 105° C. for 6-8 h. After completion of the reaction, the mixture was cooled to 25° C. to 30° C. and quenched with 10 mL of chilled water under stirring at 25° C. to 30° C. The organic layer was separated, and the aqueous layer was washed with 5 mL of toluene. The combined organic layers was washed with 5 mL of 1N HCl solution, 5 of 5% sodium bicarbonate solution and 5 mL of 10% sodium chloride solution. The organic layer was distilled to yield a crude material, which was purified by column chromatography (silica gel, chloroform-methanol) to yield the title compound.

Yield: 0.2 g (23%).

EXAMPLE 34

4-[2-(3-Nonyl-[1,2,4]oxadiazol-5-yl)-vinyl]-benzene-1,2-diol

To a cooled solution of 0.06 mL of boron tribromide (0.6 mmol) in 2 mL dichloromethane, 5-[2-(3,4-dimethoxy-phenyl)-vinyl]-3-nonyl-[1,2,4]oxadiazole (compound of Example 33; 0.1 g, 0.27 mmol) dissolved in 8 mL of dichloromethane was added over a period of 15-20 min at −45° C. to −40° C. The reaction mixture was stirred at −45 to −40° C. for 15-20 min and allowed to attain a temperature of 25° C. to 30° C. over a period of 1 h. The reaction mixture was further stirred at 25° C. to 30° C. for 4-5 h. After the completion of the reaction, the reaction mixture was quenched in 20 mL of chilled 5% sodium bicarbonate solution at a temperature below 20° C. (pH 8-9). 10 mL of ethyl acetate was added to the reaction mixture to dissolve the solid and stirred for 10-15 min. The organic layer was separated and the aqueous layer was washed with 10 mL of 10% sodium chloride solution. The organic layer was collected and distilled to obtain a crude material, which was purified by column chromatography (silica gel, chloroform-methanol) to yield the title compound.

Yield: 0.025 g (27%); $^1$H NMR (DMSO-$d_6$, 300 MHz): δ 9.64 (s, 1H), 9.17 (s, 1H), 7.61 (d, 1H), 7.12 (5H), 7.07 (d, 1H), 6.91 (d, 1H), 6.76 (d, 1H), 2.65 (t, 2H), 1.63 (m, 2H), 1.24 (m, 12H), 0.83 (t, 3H); MS (ES−): 329 (M−1).

EXAMPLE 35

N-Hydroxy-cyclopropanecarboximidamide

To a solution of 3.11 g (44.7 mmol) of hydroxylamine hydrochloride in 22 mL of isopropyl alcohol, 5.50 g (65.5 mmol) of sodium bicarbonate was added. The resulting mixture was stirred at 25° C. to 30° C. for 10-15 min. 2.0 g (29.8 mmol) of cyclopropanecarbonitrile was added and stirred at 80° C. to 85° C. for 3-4 h. After the reaction was completed, the reaction mixture was cooled to 25° C. to 30° C., filtered and washed with 6 mL of isopropyl alcohol. The filtrate was collected and distilled out completely to yield the title compound.

Yield: 2.1 g (70%).

EXAMPLE 36

3-Cyclopropyl-5-[2-(3,4-dimethoxy-phenyl)-vinyl]-[1,2,4]oxadiazole

To a solution of 2.74 g (13.2 mmol) of 3-(3,4-dimethoxyphenyl)-acrylic acid (compound of Example 2; Step 1) in 20 mL of toluene, 2.18 g (13.4 mmol) of 1,1-carbonyldiimidazole was added in portions at 25° C. to 30° C. under inert atmosphere. To the thickened mixture, 5 mL of toluene was added and the resulting mixture was stirred at 25° C. to 30° C. for 60 to 90 min. A solution of N-hydroxy-cyclopropanecarboximidamide (compound of Example 35; 2.1 g, 26.9 mmol) in 10 mL of toluene was added to the above reaction mixture as one portion at 25° C. to 30° C. The reaction mixture was stirred at 25° C. to 30° C. under nitrogen for 12-14 h, followed by stirring at 100° C. to 105° C. for 6-8 h. After completion of the reaction, the reaction mixture was cooled to 25° C. to 30° C. and quenched with 20 mL of chilled water under stirring at 25° C. to 30° C. The organic layer was separated, and the aqueous layer was washed with 10 mL of toluene. The organic layers were combined and washed with 20 mL of 1N HCl solution, 10 mL of 5% sodium bicarbonate solution and 10 mL of 10% sodium chloride solution. The organic layer was distilled completely to obtain a crude material, which was purified by column chromatography (silica gel, chloroform-methanol) to yield the title compound.

Yield: 0.1 g (3.6%).

EXAMPLE 37

4-[2-(3-Cyclopropyl-[1,2,4]oxadiazol-5-yl)-vinyl]-benzene-1,2-diol

To a cooled solution of 0.79 mL of 1M boron tribromide (0.79 mmol) in 2 mL dichloromethane, 0.1 g (0.34 mmol) of cyclopropyl-5-[2-(3,4-dimethoxy-phenyl)-vinyl]-[1,2,4]oxadiazole (compound of Example 36) dissolved in 1 mL of dichloromethane was added, over a period of 15-20 min at −40° C. to −45° C. The reaction mixture was stirred at −40° C. to −45° C. for 30-45 min and allowed to attain 25° C. to 30° C. slowly, over a period of 1 h. The reaction mixture was further stirred at 25° C. to 30° C. for 4-5 h. After the completion of the reaction, the reaction mixture was quenched with 10 mL of chilled 5% sodium bicarbonate solution, below 20° C. (pH: 8-9). 10 mL of ethyl acetate was added to the reaction mass to dissolve the solid and stirred for 10-15 min. The organic layer was separated and the aqueous layer was washed with 10 mL of 10% sodium chloride solution. The organic layer was collected and distilled to obtain a crude material, which was purified by column chromatography (silica gel, chloroform-methanol) to yield the title compound.

Yield: 0.016 g (17.9%); $^1$H NMR (DMSO-$d_6$, 300 MHz): δ 9.46 (s, 2H), 7.56 (d, 1H), 7.10 (d, 1H) 7.07 (d, 1H), 6.86 (d, 1H), 6.75 (d, 1H), 2.08 (m, 1H), 1.04 (m, 2H), 0:89 (m, 2H); MS (ES−): 243 (M−1).

EXAMPLE 38

N-hydroxy hexanimidamide

To a solution of 0.107 g (15.4 mmol) of hydroxylamine hydrochloride in 11 mL of isopropyl alcohol, 1.90 g (22.64 mmol) of sodium bicarbonate was added. The resulting mixture was stirred at 25° C. to 30° C. for 10-15 min. 1.0 g (10.2 mmol) of hexanenitrile was added and stirred at 80° C. to 85° C. for 3-4 h. After the reaction period, the reaction mixtures was cooled to 25° C. to 30° C., filtered and washed with 2 mL of isopropyl alcohol. The filtrate was collected and distilled out completely to obtain a crude residue. The residue with chased with 5 mL of toluene, to yield the title compound.

Yield: 1.0 g (74.6%).

EXAMPLE 39

5-[2-(3,4-Dimethoxy-phenyl)-vinyl]-3-pentyl-[1,2,4] oxadiazole

To a solution of 0.70 g (3.39 mmol) of 3-(3,4-dimethoxy-phenyl)-acrylic acid (compound of Example 2; Step 1) in 6 mL of toluene, 0.59 g (3.69 mmol) of 1,1-carbonyldiimidazole was added in portions at 25° C. to 30° C. under an inert atmosphere. To the thickened reaction mixture, 5 mL of toluene was added and the resulting mixture was stirred at 25° C. to 30° C. for 60 to 90 min. A solution of N-hydroxy-hexan-imidamide (compound of Example 38; 0.9 g, 6.9 mmol) diluted with 5 mL of toluene was added to the above reaction mixture at 25° C. to 30° C. The reaction mass was stirred at 25° C. to 30° C. under nitrogen for 12-14 h, followed by stirring at 100° C. to 105° C. for 6-8 h. After the completion of the reaction, the reaction mixture was cooled to 25° C. to 30° C. and quenched with 10 mL of chilled water under stirring at 25° C. to 30° C. The organic layer was separated, and the aqueous layer was washed with 5 mL of toluene. The organic layers were combined and washed with 10 mL of 1N HCl solution, 10 mL of 5% sodium bicarbonate solution and 10 mL of 10% sodium chloride solution. The organic layer was distilled completely to obtain a crude material, which was purified by column chromatography (silica gel, chloroform-methanol) to yield the title compound.

Yield: 0.3 g (28.9%).

EXAMPLE 40

4-[2-(3-Pentyl-[1,2,4]oxadiazol-5-yl)-vinyl]-benzene-1,2-diol

To a cooled solution of 1M boron tribromide (1.52 mL, 1.5 mmol) in 2 mL dichloromethane, 0.2 g (0.6 mmol) of 5-[2-(3,4-dimethoxy-phenyl)-vinyl]-3-pentyl-[1,2,4]oxadiazole (compound of Example 39) dissolved in 1 mL of dichloromethane was added over a period of 15-20 min at −40° C. to −45° C. The reaction mixture was stirred at −40 to −45° C. for 30-45 min and allowed to attain 25° C. to 30° C. slowly, over a period of 1 h. The reaction mixture was further stirred at 25° C. to 30° C. for 4-5 h. After the completion of the reaction, the reaction mixture was quenched with 10 mL of chilled 5% sodium bicarbonate solution, below 20° C. (pH: 8-9). 10 mL of ethyl acetate was added to the reaction mixture to dissolve the solid and stirred for 10-15 min. The organic layer was separated and the aqueous layer was washed with 10 mL of 10% sodium chloride solution. The organic layer was collected and distilled to obtain a crude residue, which was purified by column chromatography (silica gel, chloroform-methanol) to yield the title compound.

Yield: 0.025 g (13.8%); $^1$H NMR (CDCl$_3$-d$_6$, 300 MHz): δ 7.66 (d, 1H), 7.14 (s, 1H), 7.04 (m, 1H), 6.90 (d, 1H), 6.78 (d, 1H), 6.01 (s, 2H), 2.74 (t, 2H), 1.77 (m, 2H), 1.35 (m, 4H), 0.91 (t, 3H); MS (ES−): 273 (M−1).

EXAMPLE 41

N-hydroxy-heptanimidamide

To a solution of 0.93 g (13.4 mmol) of hydroxylamine hydrochloride in 11 mL of isopropyl alcohol, 1.66 g (19.78 mmol) of sodium bicarbonate was added. The resulting mixture was stirred at 25° C. to 30° C. for 10-15 min. 1.0 g (8.9 mmol) of hexanenitrile was added and stirred at 80° C. to 85° C. for 3-4 h. After completion of the reaction, the reaction mixture was cooled to 25° C. to 30° C., filtered and washed with 2 mL of isopropyl alcohol. The filtrate was collected and distilled out completely to obtain a crude residue, which was chased with 5 mL of toluene, to yield the title compound.

Yield: 1.0 g (77.5%).

EXAMPLE 42

5-[2-(3,4-Dimethoxy-phenyl)-vinyl]-3-hexyl-[1,2,4] oxadiazole

To a solution of 0.63 g (2.08 mmol) of 3-(3,4-dimethoxy-phenyl)-acrylic acid (compound of Example 2; Step 1) in 6 mL of toluene, 0.540 g (3.33 mmol) of 1,1-carbonyldiimidazole was added in portions at 25° C. to 30° C. under inert atmosphere. To the thickened reaction mixture, 5 mL of toluene was added and the resulting mixture was stirred at 25° C. to 30° C. for 60 to 90 min. A solution of N-hydroxy-heptanimidamide (compound of Example 41; 0.9 g, 6.2 mmol) in 5 mL of toluene was added to the above reaction mixture at 25° C. to 30° C. The reaction mixture was stirred at 25° C. to 30° C. under nitrogen for 12-14 h, followed by stirring at 100° C. to 105° C. for 6-8 h. After completion of the reaction, the reaction mixture was cooled to 25° C. to 30° C. and quenched with 10 mL of chilled water under stirring at 25° C. to 30° C. The organic layer was separated, and the aqueous layer was washed with 5 mL of toluene. The organic layers were combined and washed with 10 mL of 1N HCl solution, 10 mL of 5% sodium bicarbonate solution and 10 mL of 10% sodium chloride solution. The organic layer was distilled completely to obtain a crude residue, which was purified using column chromatography (silica gel, chloroform-methanol) to yield the title compound.

Yield: 0.2 g (21%)

EXAMPLE 43

4-[2-(3-Hexyl-[1,2,4]oxadiazol-vinyl]-benzyldiol

To a cooled solution of 1.44 mL of 1M boron tribromide (1.4 mmol) in 2 mL dichloromethane, 0.2 g (0.6 mmol) of 5-[2-(3,4-dimethoxy-phenyl)-vinyl]-3-hexyl-[1,2,4]oxadia-zole (compound of Example 42) dissolved in 2 mL of dichloromethane was added over a period of 15-20 min at −40° C. to −45° C. The reaction mixture was stirred at −40 to −45° C. for 30-45 min and allowed to attain 25° C. to 30° C. slowly, over a period of 1 h. The reaction mixture was further stirred at 25° C. to 30° C. for 4-5 h. After the completion of the reaction, the reaction mixture was quenched with 10 mL of chilled 5% sodium bicarbonate solution, below 20° C. (pH: 8-9). 10 mL of ethyl acetate was added to the reaction mass to dissolve the solid and stirred for 10-15 min. The organic layer was separated and the aqueous layer was washed with 10 mL of 10% sodium chloride solution. The organic layer was collected and distilled to obtain a crude residue, which was purified by column chromatography (silica gel, chloroform-methanol) to yield the title compound.

Yield: 0.117 g (64%); $^1$H NMR (CDCl$_3$-d$_6$, 300 MHz): δ 8.16 (s, 1H), 7.97 (s, 1H), 7.55 (d, 1H), 7.04 (d, 1H), 6.89 (m, 1H), 6.79 (d, 1H), 6.67 (d, 1H), 2.63 (t, 2H), 1.66 (m, 2H), 1.27 (m, 6H), 0.79 (t, 3H); MS (ES−): 287 (M−1).

EXAMPLE 44

2-cyclohexyl-N-hydroxyacetimidamide

To a solution of 0.846 g (8.1 mmol) of hydroxylamine hydrochloride in 11 mL of isopropyl alcohol, 1.499 g (17.8 mmol) of sodium bicarbonate was added. The resulting mixture was stirred at 25° C. to 30° C. for 10-15 min. 1.0 g (8.1 mmol) of 2-cyclohexylacetonitrile was added and stirred at 80° C. to 85° C. for 3-4 h. After completion of the reaction, the reaction mixture was cooled to 25° C. to 30° C., filtered and washed with 2 mL of isopropyl alcohol. The filtrate was collected and distilled out completely to obtain a crude residue. The residue was chased with 5 mL of toluene to yield the title compound.

Yield: 0.6 g (47%).

EXAMPLE 45

3-Cyclohexylmethyl-5-[2-(3,4-dimethoxy-phenyl)-vinyl]-[1,2,4]oxadiazole

To a solution of 0.39 g (1.88 mmol) of 3-(3,4-dimethoxy-phenyl)-acrylic acid (compound of Example 2; Step 1) in 6 mL of toluene, 0.333 g (2.00 mmol) of 1,1-carbonyldiimidazole was added in portions at 25° C. to 30° C. under inert atmosphere. To the thickened mixture, 5 mL of toluene was added and the resulting mixture was stirred at 25° C. to 30° C. for 60 to 90 min. A solution of 2-cyclohexyl-N-hydroxyacetimidamide (compound of Example 44; 0.6 g, 3.8 mmol) in 5 mL of toluene was added to the above reaction mixture at 25° C. to 30° C. The reaction mass was stirred at 25° C. to 30° C. under nitrogen for 12-14 h, followed by stirring at 100° C. to 105° C. for 6-8 h. After completion of the reaction, the reaction mixture was cooled to 25° C. to 30° C. and quenched with 10 mL of chilled water under stirring at 25° C. to 30° C. The organic layer was separated, and the aqueous layer was washed with 5 mL of toluene. The organic layers were combined and washed with 10 mL of 1N HCl solution, 10 mL of 5% sodium bicarbonate solution and 10 mL of 10% sodium chloride solution. The organic layer was distilled completely to obtain a crude residue, which was purified by column chromatography (silica gel, chloroform-methanol) to yield the title compound.

Yield: 0.22 g (35%).

EXAMPLE 46

4-[2-(3-Cyclohexylmethyl-[1,2,4]oxadiazol-5-yl)-vinyl]-benzene-1,2-diol

To a cooled solution of 0.14 mL of 1M boron tribromide (1.5 mmol) in 2 mL dichloromethane, 0.216 g (0.658 mmol) of 3-cyclohexylmethyl-5-[2-(3,4-dimethoxy-phenyl)-vinyl]-[1,2,4]oxadiazole (compound of Example 45) dissolved in 1 mL of dichloromethane was added over a period of 15-20 min at −45° C. to −40° C. The reaction mixture was stirred at −45° C. to −40° C. for 30-45 min and allowed to attain 25° C. to 30° C. slowly, over a period of 1 h. The reaction mixture was further stirred at 25° C. to 30° C. for 4-5 h. After the completion of the reaction, the reaction mixture was quenched with 10 mL of chilled 5% sodium bicarbonate solution, below 20° C. (pH: 8-9). 10 mL of ethyl acetate was added to the reaction mass to dissolve the solid and stirred for 10-15 min. The organic layer was separated and the aqueous layer was washed with 10 mL of 10% sodium chloride solution. The organic layer was collected and distilled to obtain a crude residue, which was purified by column chromatography (silica gel, chloroform-methanol) to yield the title compound.

Yield: 0.10 g (50.8%); $^1$H NMR (CDCl$_3$-d$_8$, 300 MHz): δ 9.38 (s, 2H), 7.62 (d, 1H), 7.12 (d, 1H), 7.08 (m, 1H), 6.92 (d, 1H), 6.77 (d, 1H), 2.55 (m, 2H), 1.64 (m, 6H), 1.17 (m, 3H), 0.97 (m, 2H); MS (ES−): 299 (M−1).

EXAMPLE 47

N-hydroxynonanimidamide

To a solution of 0.74 g (10.7 mmol) of hydroxylamine hydrochloride in 11 mL of isopropyl alcohol, 1.327 g (17.8 mmol) of sodium bicarbonate was added. The resulting mixture was stirred at 25° C. to 30° C. for 10-15 min. 1.0 g (7.1 mmol) of nonanenitrile was added and stirred at 80° C. to 85° C. for 3-4 h. After the reaction period, the reaction mixture was cooled to 25° C. to 30° C., filtered and washed with 2 mL of isopropyl alcohol. The filtrate was collected and distilled out completely to obtain a crude residue. The residue with chased with 5 mL of toluene below 45° C., under vacuum, to yield the title compound.

Yield: 1.1 g (89.4%).

EXAMPLE 48

5-[2-(3,4-Dimethoxy-phenyl)-vinyl]-3-octyl-[1,2,4]oxadiazole

To a solution of 0.59 g (2.84 mmol) of 3-(3,4-dimethoxy-phenyl)-acrylic acid (compound of Example 2; Step 1) in 6 mL of toluene, 0.503 g (3.1 mmol) of 1,1-carbonyldiimidazole was added in portions at 25° C. to 30° C. under inert atmosphere. To the thickened mixture, 5 mL of toluene was added and the resulting mixture was stirred at 25° C. to 30° C. for 60 to 90 min. A solution of N-hydroxynonanimidamide (compound of example 47; 1.0 g, 3.8 mmol) diluted with 5 mL of toluene was added to the above reaction mixture at 25° C. to 30° C. The reaction mixture was stirred at 25° C. to 30° C. under nitrogen for 12-14 h, followed by stirring at 100° C. to 105° C. for 6-8 h. After completion of the reaction, the reaction mixture was cooled to 25° C. to 30° C. and quenched with 10 mL of chilled water under stirring at 25° C. to 30° C. The organic layer was separated, and the aqueous layer was washed with 5 mL of toluene. The organic layers were combined and washed with 10 mL of 1N HCl solution, 10 mL of 5% sodium bicarbonate solution and 10 mL of 10% sodium chloride solution. The organic layer was distilled to obtain a crude residue, which was purified by column chromatography (silica gel, chloroform-methanol) to yield the title compound.

Yield: 0.2 g (20.5%)

EXAMPLE 49

4-[2-(3-Octyl-[1,2,4]oxadiazol-5-yl)-vinyl]-benzene-1,2-diol

To a cooled solution of 0.997 mL of 1M boron tribromide (0.9 mmol) in 2 mL dichloromethane, 0.150 g (0.433 mmol) of 5-[2-(3,4-dimethoxy-phenyl)-vinyl]-3-octyl-[1,2,4]oxadiazole (compound of Example 48) dissolved in 1 mL of dichloromethane was added over a period of 15-20 min at −45° C. to −40° C. The reaction mixture was stirred at −45° C. to −40° C. for 30-45 min and allowed to attain 25° C. to 30° C. slowly, over a period of 1 h. The reaction mass was further stirred at 25° C. to 30° C. for 4-5 h. After completion of the reaction, the reaction mixture was quenched in 10 mL of chilled 5% sodium bicarbonate solution, below 20° C. (pH: 8-9). 10 mL of ethyl acetate was added to the reaction mixture to dissolve the solid and stirred for 10-15 min. The organic layer was separated and the aqueous layer was washed with 10 mL of 10% sodium chloride solution. The organic layer was collected and distilled to obtain a crude residue, which was purified by column chromatography (silica gel, chloroform-methanol) to yield the title compound.

Yield: 0.050 g (36.6%) $^1$H NMR (CDCl$_3$-d$_6$, 300 MHz): δ 7.67 (d, 1H), 7.17 (s, 1H), 7.03 (d, 1H), 6.89 (d, 1H), 6.78 (d, 1H), 2.74 (t, 2H), 128 (m, 12H), 0.86 (m, 3H); MS (ES−): 315 (M−1).

EXAMPLE 50

N-hydroxyoctanimidamide

To a solution of 1.66 g (23.9 mmol) of hydroxylamine hydrochloride in 11 mL of isopropyl alcohol, 2.95 g (35.1 mmol) of sodium bicarbonate was added. The resulting mixture was stirred at 25° C. to 30° C. for 10-15 min. 2.0 g (15.97 mmol) of octanenitrile was added and stirred at 80° C. to 85° C. for 3-4 h. After completion of the reaction, the reaction mixture was cooled to 25° C. to 30° C., filtered and washed with 2 mL of isopropyl alcohol. The filtrate was collected and distilled to obtain a crude residue. The residue was chased with 5 mL of toluene, to yield the title compound.

Yield: 2.1 g (83%)

EXAMPLE 51

5-[2-(3,4-Dimethoxy-phenyl)-vinyl]-3-heptyl-[1,2,4]oxadiazole

To a solution of 1.35 gm (6.5 mmol) of 3-(3,4-dimethoxy-phenyl)-acrylic acid (compound of Example 2; Step 1) in 6 mL of toluene, 1.14 gm (7.0 mmol) of 1,1-carbonyldiimidazole was added lot wise at 25° C. to 30° C. under inert atmosphere. The mass becomes thick and 5 mL of toluene was added and the resulting mixture was stirred at 25° C. to 30° C. for 60 to 90 min. A solution of N-hydroxyoctanimidamide (compound of Example 50; 2.1 g, 13.2 mmol) in 5 mL of toluene was added to the above reaction mixture as one lot at 25° C. to 30° C. The reaction mixture was stirred at 25° C. to 30° C. under nitrogen for 12-14 h, followed by stirring at 100° C. to 105° C. for 6-8 h. After completion of the reaction, the reaction mixture was cooled to 25° C. to 30° C. and quenched with 10 mL of chilled water under stirring at 25° C. to 30° C. The organic layer was separated, and the aqueous layer was washed with 5 mL of toluene. The organic layers were combined and washed with 10 mL of 1N HCl solution, 10 mL of 5% sodium bicarbonate solution and 10 mL of 10% sodium chloride solution. The organic layer was distilled to obtain a crude residue, which was purified by column chromatography (silica gel, chloroform-methanol) to yield the title compound.

Yield: 0.34 g (15.9° A))

EXAMPLE 52

4-[2-(3-Heptyl-[1,2,4]oxadiazol-5-yl)-vinyl]-benzene-1,2-diol

To a cooled solution of 2.09 mL of 1M boron tribromide (2.0 mmol) in 2 mL dichloromethane, 0.300 g (0.9 mmol) of 5-[2-(3,4-dimethoxy-phenyl)-vinyl]-3-heptyl-[1,2,4]oxadiazole (compound of Example 51) dissolved in 1 mL of dichloromethane was added over a period of 15-20 min at −45° C. to −40° C. The reaction mixture was stirred at −45° C. to −40° C. for 30-45 min and allowed to attain a temperature of 25° C. to 30° C. slowly, over a period of 1 h. The reaction mixture was further stirred at 25° C. to 30° C. for 4-5 h. After completion of the reaction, the reaction mixture was quenched in 10 mL of chilled 5% sodium bicarbonate solution, below 20° C. (pH: 8-9). 10 mL of ethyl acetate was added to the reaction mass to dissolve the solid and stirred for 10-15 min. The organic layer was separated and the aqueous layer was washed with 10 mL of 10% sodium chloride solution. The organic layer was collected and distilled to obtain a crude residue, which was purified by column chromatography (silica gel, chloroform-methanol) to yield the title compound.

Yield: 0.132 g (48%); $^1$H NMR (DMSO-d$_6$, 300 MHz): δ 8.06 (s, 2H), 7.53 (d, 1H), 7.01 (d, 1H), 6.85 (m, 1H), 617 (d, 1H), 6.64 (d, 1H), 2.61 (t, 2H), 1.64 (m, 2H), 1.23 (m, 8H), 0.76 (m, 3H); MS (ES−): 301 (M−1).

EXAMPLE 53

N-hydroxy-nicotinimidamide

To a solution of 5.012 g (72.1 mmol) of hydroxylamine hydrochloride in 55 mL of isopropyl alcohol, 8.8 g (105.7 mmol) of sodium bicarbonate was added. The resulting mixture was stirred at 25° C. to 30° C. for 10-15 min. 5.0 g (48 mmol) of 3-cyanopyridine was added and stirred at 80° C. to 85° C. for 3-4 h. After completion of the reaction, the reaction mixture was cooled to 25° C. to 30° C., filtered and washed with 10 mL of isopropyl alcohol. The filtrate was collected and distilled to obtain a crude residue, which was chased with 5 mL of toluene to yield the title compound.

Yield: 6.0 g (91%).

EXAMPLE 54

3-{5-[2-(3,4-Dimethoxy-phenyl)-vinyl]-[1,2,4]oxadiazol-3-yl}-pyridine

To a solution of 4.35 g (20.95 mmol) of 3-(3,4-dimethoxy-phenyl)-acrylic acid (compound of Example 2; Step 1) in 35 mL of toluene, 3.703 g (22.8 mmol) of 1,1-carbonyldiimidazole was added in portions at 25° C. to 30° C. under inert atmosphere. To the thickened mixture, 15 mL of toluene was added and the resulting mixture was stirred at 25° C. to 30° C. for 60 to 90 min. A solution of N-hydroxy-nicotinimidamide (compound of Example 53; 6 g, 43.7 mmol) in 5 mL of toluene was added to the above reaction mixture at 25° C. to 30° C. The reaction mixture was stirred at 25° C. to 30° C. under nitrogen for 12-14 h, followed by stirring at 100° C. to 105° C. for 6-8 h. After completion of the reaction, the reaction mixture was cooled to 25° C. to 30° C. and quenched with 10 mL of chilled water under stirring at 25° C. to 30° C. The organic layer was separated, and the aqueous layer was washed with 5 mL of toluene. The organic layers were combined and washed with 10 mL of 1N HCl solution, 10 mL of 5% sodium bicarbonate solution and 10 mL of 10% sodium chloride solution. The organic layer was distilled completely to obtain a crude residue, which was purified by column chromatography (silica gel, chloroform-methanol) to yield the title compound.

Yield: 1.2 g (13.5%).

EXAMPLE 55

4-[2-(3-Pyridin-3-yl-[1,2,4]oxadiazol-5-yl)-vinyl]-benzene-1,2-diol

To a cooled solution of 0.35 mL of 1M boron tribromide (3.7 mmol) in 2 mL dichloromethane, 0.500 g (1.6 mmol) of 3-{5-[2-(3,4-dimethoxy-phenyl)-vinyl]-[1,2,4]oxadiazol-3-yl}-pyridine (compound of Example 54) dissolved in 5 mL of dichloromethane was added over a period of 15-20 min at −45° C. to −40° C. The reaction mixture was stirred at −45° C. to −40° C. for 30-45 min and allowed to attain a temperature of 25° C. to 30° C. slowly, over a period of 1 h. The reaction mixture was further stirred at 25° C. to 30° C. for 4-5 h. After completion of the reaction, the reaction mixture was quenched in 10 mL of chilled 5% sodium bicarbonate solution, below 20° C. (pH: 8-9). 10 mL of ethyl acetate was added to the reaction mixture to dissolve the solid and stirred for 10-15 min. The organic layer was separated and the aqueous layer was washed with 10 mL of 10% sodium chloride solution. The organic layer was collected and distilled to obtain a crude residue, which was purified by column chromatography (silica gel, chloroform-methanol) to yield the title compound.

Yield: 0.20 g (44.4%); $^1$H NMR (DMSO-$d_6$, 300 MHz): δ 9.25 (s, 1H), 8.84 (d, 1H), 8.53 (d, 1H), 7.76 (m, 2H), 7.13 (m, 3H), 6.80 (d, 1H); MS (ES−): 280 (M−1).

EXAMPLE 56

N-cycloheptanecarboximidamide

To a solution of 1.69 g (24.3 mmol) of hydroxylamine hydrochloride in 22 mL of isopropyl alcohol, 2.99 g (35.7 mmol) of sodium bicarbonate was added. The resulting mixture was stirred at 25° C. to 30° C. for 10-15 min. 2.0 g (16.2 mmol) of cycloheptanecarbonitrile was added and stirred at 80° C. to 85° C. for 3-4 h. After the completion of the reaction, the reaction mixture was cooled to 25° C. to 30° C., filtered and washed with 10 mL of isopropyl alcohol. The filtrate was collected and distilled to obtain a crude residue, which was chased with 5 mL of toluene to yield the title compound.

Yield: 2.0 g (79.3%).

EXAMPLE 57

3-Cycloheptyl-5-[2-(3,4-dimethoxy-phenyl)-vinyl]-[1,2,4]oxadiazole

To a solution of 1.30 g (6.2 mmol) of 3-(3,4-dimethoxy-phenyl)-acrylic acid (compound of Example 2; Step 1) in 22 mL of toluene, 1.098 g (6.7 mmol) of 1,1-carbonyldiimidazole was added in portions at 25° C. to 30° C. under inert atmosphere. To the thickened mixture, 22 mL of toluene was added and the resulting mixture was stirred at 25° C. to 30° C. for 60 to 90 min. A solution of N-cycloheptanecarboximidamide (compound of Example 56; 2 g, 12.8 mmol) in 5 mL of toluene was added to the above reaction mixture at 25° C. to 30° C. The reaction mixture was stirred at 25° C. to 30° C. under nitrogen for 12-14 h, followed by stirring at 100° C. to 105° C. for 6-8 h. After completion of the reaction, the reaction mixture was cooled to 25° C. to 30° C. and quenched with 10 mL of chilled water under stirring at 25° C. to 30° C. The organic layer was separated, and the aqueous layer was washed with 5 mL of toluene. The organic layers were combined and washed with 10 mL of 1N HCl solution, 10 mL of 5% sodium bicarbonate solution and 10 mL of 10% sodium chloride solution. The organic layer was distilled completely to obtain a crude residue, which was purified by column chromatography (silica gel, chloroform-methanol) to yield the title compound.

Yield: 1.5 g (72.6%).

EXAMPLE 58

4-[2-(3-Cycloheptyl-[1,2,4]oxadiazol-5-yl)-vinyl]-benzene-1,2-diol

To a cooled solution of 1 mL of 1M boron tribromide (10.5 mmol) in 2 mL dichloromethane, 1.5 g (4.5 mmol) of 3-cycloheptyl-5-[2-(3,4-dimethoxy-phenyl)-vinyl]-[1,2,4]oxadiazole (compound of Example 57) dissolved in 15 mL of dichloromethane was added over a period of 15-20 min at −45° C. to −40° C. The reaction mixture was stirred at −45° C. to −40° C. for 30-45 min and allowed to attain a temperature of 25° C. to 30° C. slowly, over a period of 1 h. The reaction mixture was further stirred at 25° C. to 30° C. for 4-5 h. After completion of the reaction, the reaction mixture was quenched with 10 mL of chilled 5% sodium bicarbonate solution, below 20° C. (pH: 8-9). 10 mL of ethyl acetate was added to the reaction mixture to dissolve the solid and stirred for 10-15 min. The organic layer was separated and the aqueous layer was washed with 10 mL of 10% sodium chloride solution. The organic layer was collected and distilled to obtain a crude residue, which was purified by column chromatography (silica gel, chloroform-methanol) to yield the title compound.

Yield: 0.35 g (25.6%); $^1$H NMR (CDCl$_3$-$d_6$, 300 MHz): δ 9.58 (s, 1H), 9.21 (s, 1H), 7.61 (d, 1H), 7.11 (d, 1H), 7.06 (m, 1H), 6.91 (d, 1H), 6.77 (d, 1H), 2.95 (m, 1H), 1.96 (m, 2H), 1.71 (m, 5H), 1.57 (m, 5H); MS (ES−): 299 (M−1).

EXAMPLE 59

N-hydroxycyclohexanecarboximidamide

To a solution of 1.9 g (27.4 mmol) of hydroxylamine hydrochloride in 22 mL of isopropyl alcohol, 3.3 g (40.3 mmol) of sodium bicarbonate was added. The resulting mixture was stirred at 25° C. to 30° C. for 10-15 min. 2.0 g (18.3 mmol) of cyclohexanecarbonitrile was added and stirred at 80° C. to 85° C. for 3-4 h. After the reaction period, the reaction mass was cooled to 25° C. to 30° C., filtered and washed with 10 mL of isopropyl alcohol. The filtrate was collected and distilled out completely to obtain a crude residue. The residue was chased with 5 mL of toluene, to yield the title compound.

Yield: 2.0 g (76.9%)

EXAMPLE 60

3-Cyclohexyl-5-[2-(3,4-dimethoxy-phenyl)-vinyl]-[1,2,4]oxadiazole

To a solution of 1.43 g (6.9 mmol) of 3-(3,4-dimethoxy-phenyl)-acrylic acid (compound of Example 2; Step 1) in 22 mL of toluene, 1.21 g (7.5 mmol) of 1,1-carbonyldiimidazole was added in portions at 25° C. to 30° C. under inert atmosphere. To the thickened mixture, 22 mL of toluene was added and the resulting mixture was stirred at 25° C. to 30° C. for 60 to 90 min. A solution of N-hydroxycyclohexanecarboximidamide (compound of Example 59; 2 g, 14 mmol) in 5 mL of toluene was added to the above reaction mixture at 25° C. to 30° C. The reaction mixture was stirred at 25° C. to 30° C. under nitrogen for 12-14 h, followed by stirring at 100° C. to 105° C. for 6-8 h. After completion of the reaction, the reaction mixture was cooled to 25° C. to 30° C. and quenched with 10 mL of chilled water under stirring at 25° C. to 30° C. The organic layer was separated, and the aqueous layer was washed with 5 mL of toluene. The organic layers were combined and washed with 10 mL of 1N HCl solution, 10 mL of 5% sodium bicarbonate solution and 10 mL of 10% sodium chloride solution. The organic layer was distilled completely to obtain a crude residue, which was purified by column chromatography (silica gel, chloroform-methanol) to yield the title compound.

Yield: 0.8 g (37.2%)

EXAMPLE 61

4-[2-(3-Cyclohexyl-[1,2,4]oxadiazol-5-yl)-vinyl]-benzene-1,2-diol

To a cooled solution of 0.55 mL of 1M boron tribromide (5.8 mmol) in 2 mL dichloromethane, 0.8 g (2.5 mmol) of 3-cyclohexyl-5-[2-(3,4-dimethoxy-phenyl)-vinyl]-[1,2,4]oxadiazole (compound of Example 60) dissolved in 8 mL of dichloromethane was added over a period of 15-20 min at −45° C. to −40° C. The reaction mixture was stirred at −45° C. to −40° C. for 30-45 min and allowed to attain a temperature of 25° C. to 30° C. slowly, over a period of 1 h. The reaction mixture was further stirred at 25° C. to 30° C. for 4-5 h. After completion of the reaction, the reaction mixture was quenched with 10 mL of chilled 5% sodium bicarbonate solution, below 20° C. (pH: 8-9). 10 mL of ethyl acetate was added to the reaction mixture to dissolve the solid and stirred for 10-15 min. The organic layer was separated and washed with 10 mL of 10% sodium chloride solution. The organic layer was distilled to obtain a crude residue, which was purified by column chromatography (silica gel, chloroform-methanol) to yield the title compound.

Yield: 0.28 g (38.8%); $^1$H NMR (CDCl$_3$-d$_6$, 300 MHz): δ 9.38 (s, 2H), 7.61 (d, 1H), 7.11 (d, 1H), 7.06 (m, 1H), 6.91 (d, 1H), 6.77 (d, 1H), 2.75 (m, 1H), 1.92 (m, 2H), 1.7 (m, 3H), 1.49 (m, 2H), 1.33 (m, 3H); MS (ES−): 285 (M−1).

Biological Evaluation:

The efficacy of the compounds of the present invention in inhibiting the imatinib mesylate sensitive cell line K-562 and Ba/F3Bcr-Abl/WT and imatinib mesylate resistant cell lines, Ba/F3Bcr-Abl/T315I, Ba/F3Bcr-Abl/E255K, Ba/F3 Bcr-Abl/H396P, Ba/F3Bcr-Abl/M351T, Ba/F3Bcr-Abl/F359V, Ba/F3Bcr-Abl/E255V, Ba/F3Bcr-Abl/F317L, Ba/F3Bcr-Abl/H396R, Ba/F3Bcr-Abl/M244V, Ba/F3 Bcr-Abl/Q252H, Ba/F3Bcr-Abl/Y253F and Ba/F3Bcr-Abl/Y253H can be determined by number of pharmacological assays described below. The exemplified pharmacological assays, which follow, have been carried out with imatinib mesylate, and compounds of the present invention.

Several imatinib-resistant cell lines were procured from Dr. Brian Druker's laboratory, Howard Hughes Medical Institute, Oregon Health and Science University (OHSU) Cancer Institute, Portland, Oreg., USA, the details of which are provided in the Table 1. K562 cell line was procured from ATCC, USA. These cell lines were maintained under optimum conditions of growth as suggested by the respective suppliers.

TABLE 1

Description of imatinib sensitive and imatinib resistant cell lines

| Sr. No | Cell line | Source | Ph status | Medium of propagation (FBS %) |
|---|---|---|---|---|
| 1 | Ba/F3 Bcr-Abl/WT | OHSU | + ve wild type | RPMI-1640 (10%) |
| 2 | Ba/F3 Bcr-Abl/T315I | OHSU | + ve mutated | RPMI-1640 (10%) |
| 3 | Ba/F3 Bcr-Abl/E255K | OHSU | + ve mutated | RPMI-1640 (10%) |
| 4 | Ba/F3 Bcr-Abl/H396P | OHSU | + ve mutated | RPMI-1640 (10%) |
| 5 | Ba/F3 Bcr-Abl/M351T | OHSU | + ve mutated | RPMI-1640 (10%) |
| 6 | Ba/F3 Bcr-Abl/F359V | OHSU | + ve mutated | RPMI-1640 (10%) |
| 7 | Ba/F3 Bcr-Abl/E255V | OHSU | + ve mutated | RPMI-1640 (10%) |
| 8 | Ba/F3 Bcr-Abl/F317L | OHSU | + ve mutated | RPMI-1640 (10%) |
| 9 | Ba/F3 Bcr-Abl/H396R | OHSU | + ve mutated | RPMI-1640 (10%) |
| 10 | Ba/F3 Bcr-Abl/M244V | OHSU | + ve mutated | RPMI-1640 (10%) |
| 11 | Ba/F3 Bcr-Abl/Q252H | OHSU | + ve mutated | RPMI-1640 (10%) |
| 12 | Ba/F3 Bcr-Abl/Y253F | OHSU | + ve mutated | RPMI-1640 (10%) |
| 13 | Ba/F3 Bcr-Abl/Y253H | OHSU | + ve mutated | RPMI-1640 (10%) |
| 14 | K562 | ATCC | + ve wild type | RPMI-1640 (10%) |

The following abbreviations are used throughout the specification and/or the appended claims:
ATCC: American Type Culture Collection
OHSU: Oregon Health and Science University, Oregon, USA
RPMI: Roswell Park Memorial Institute
PBS: Phosphate buffered saline
PI: Propidium Iodide
+ve: Positive
TGFβ: Transforming Growth Factor-β

EXAMPLE 62

In-Vitro Assay

Cell Proliferation and Cytotoxicity CCK-8 Assay:

The assay was carried out as in reference, Biological and Pharmaceutical Bulletin, 1996, 19, 1518.

Cell Counting Kit-8 (CCK-8) assay is a sensitive colorimetric assay for the determination of number of viable cells in cell proliferation and cytotoxicity assays. Cell Counting Kit-8 (CCK-8) utilizes Dojindo's highly water-soluble tetrazolium salt. The amount of the formazan dye generated by dehydrogenases in cells is directly proportional to the number of living cells.

Source of Cell Lines and Compound Preparation:

Imatinib mesylate was purchased from Natco Pharma, India. For the compounds of the present invention and standard imatinib mesylate, 10 mM stock was prepared in DMSO.

The cell lines described in Table 1 were used to test the antiproliferative activity of the compounds of the present invention.

Method:

Cells were seeded at a density of ~5×10$^3$ per well (0.09 mL) in a transparent 96-well tissue culture plate (NUNC, USA) and allowed to incubate at 37° C., 5% CO$_2$ incubator for 2-6 h. Different concentrations of compounds of the present invention were added to the wells of the culture plate in triplicate. Imatinib mesylate was used as a standard. Plates were further incubated in an incubator at 37° C. in presence of 5% CO$_2$ for 72 h. 10 µL of the CCK-8 solution was added to each well and plate was incubated for 1-4 h in the incubator. The absorbance was measured at 450 nm using a microplate reader. The percent inhibition and IC$_{50}$ were calculated in comparison with control values.

The results are provided in the following Tables 2 and 3. Anti-proliferative activity of compounds, expressed as $IC_{50}$ values in μM for different cell lines with imatinib mesylate resistant mutations (Ba/F3Bcr-Abl/E255K, Ba/F3 Bcr-Abl/E255V, Ba/F3 Bcr-Abl/F317L, Ba/F3Bcr-Abl/F359V, Ba/F3Bcr-Abl/H396R, Ba/F3Bcr-Abl/H396P, Ba/F3Bcr-Abl/M244V, Ba/F3 Bcr-Abl/M351T, Ba/F3Bcr-Abl/Q252H, Ba/F3Bcr-Abl/Y253F, Ba/F3Bcr-Abl/Y253H and Ba/F3 Bcr-Abl/T315I) are given in Table 3.

Anti-proliferative activity of the compounds of the present invention, expressed as $IC_{50}$ values in μM, in imatinib mesylate sensitive (Ba/F3Bcr-Abl/Wild Type) and resistant (Ba/F3Bcr-Abl/T315I) cell lines are represented graphically in FIG. 1.

Figure 2:
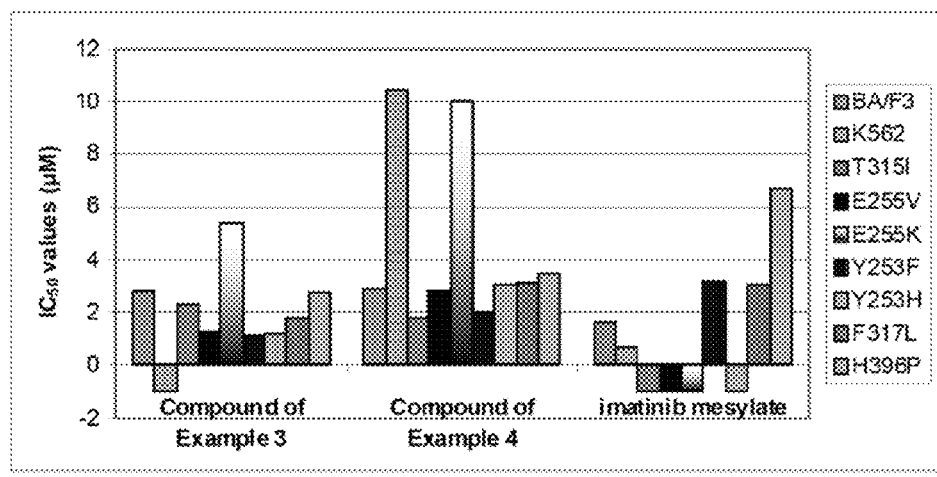
FIG. 2 shows inhibitory concentrations ($IC_{50}$) for compounds of the present invention in imatinib mesylate resistant cell lines.

Anti-proliferative activity of compounds, expressed as $IC_{50}$ values in μM for several cell lines with imatinib mesylate resistant mutations (Ba/F3, T315I, E255K, E255V, Y253F, Y253H, F317L and H396P) are represented graphically in FIG. 2.

Table 2: Inhibitory Concentrations ($IC_{50}$) for Compounds of the Present Invention in Imatinib Mesylate Sensitive and Resistant Cell Lines

TABLE 2

Inhibitory concentrations ($IC_{50}$) for compounds of the present invention in imatinib mesylate sensitive and resistant cell lines

| Sr. No | Compounds | Cell lines (IC50 in μM) | | |
|---|---|---|---|---|
| | | K562 | Ba/F3 Bcr-Abl/WT | Ba/F3 Bcr-Abl/T315I |
| | | imatinib sensitive | imatinib resistant | |
| 1 | imatinib mesylate | + | + | ++ |
| 2 | Compound of Example 1 | ++ | ++ | ++ |
| 3 | Compound of Example 2 | + | + | + |
| 4 | Compound of Example 3 | ++ | + | + |
| 5 | Compound of Example 4 | ++ | + | + |
| 6 | Compound of Example 10 | +++ | ++ | ++ |
| 7 | Compound of Example 12 | ++ | ++ | + |
| 8 | Compound of Example 20 | ++ | ++ | ++ |
| 9 | Compound of Example 22 | ++ | ++ | ++ |
| 10 | Compound of Example 24 | ++ | ++ | ++ |
| 11 | Compound of Example 31 | ++ | ++ | ++ |
| 12 | Compound of Example 34 | ++ | + | + |
| 13 | Compound of Example 37 | + | + | + |
| 14 | Compound of Example 40 | + | + | + |
| 15 | Compound of Example 43 | + | + | + |
| 16 | Compound of Example 46 | + | + | + |
| 17 | Compound of Example 49 | + | + | + |
| 18 | Compound of Example 52 | + | + | + |
| 19 | Compound of Example 55 | ++ | + | + |
| 20 | Compound of Example 58 | ++ | + | + |
| 21 | Compound of Example 61 | ++ | + | + |

+ 0-10 μM;
++ 11-100 μM;
+++ >100 μM.

TABLE 3

Cytotoxic inhibitory activity of compounds of the present invention in imatinib mesylate resistant cell lines

| Sr No | Cell-lines | Cytotoxic Inhibitory Potential ($IC_{50}$) μM | | |
|---|---|---|---|---|
| | | Compound of Example 3 | Compound of Example 4 | imatinib mesylate |
| 1 | Ba/F3 Bcr-Abl/E255K | 5.4 | >10 | 8.7 |
| 2 | Ba/F3 Bcr-Abl/E255V | 2.1 ± 0.75 | 4 ± 1.4 | 8.4 |
| 3 | Ba/F3 Bcr-Abl/F317L | 1.95 ± 0.21 | 2.85 ± 0.35 | 2.0 |
| 4 | Ba/F3 Bcr-Abl/F359V | 2 ± 0.42 | 3 ± 0.7 | 2.1 |
| 5 | Ba/F3 Bcr-Abl/H396P | 2 ± 0.98 | 2.6 ± 1.2 | 4.3 |
| 6 | Ba/F3 Bcr-Abl/H396R | 2.25 ± 0.77 | 3.05 ± 0.07 | 2.1 |
| 7 | Ba/F3 Bcr-Abl/M244V | 2.1 | 2.3 | 1.8 |
| 8 | Ba/F3 Bcr-Abl/M351T | 5.7 ± 1.7 | 7.5 ± 0.7 | 2.1 |
| 9 | Ba/F3 Bcr-Abl/Q252H | 2.6 ± 0.84 | 3.65 ± 0.65 | 2.0 |
| 10 | Ba/F3 Bcr-Abl/Y253F | 1.5 ± 0.56 | 2.1 ± 0.14 | 3.9 |
| 11 | Ba/F3 Bcr-Abl/Y253H | 1.7 ± 0.78 | 2.5 ± 0.75 | 9.2 |
| 12 | Ba/F3 Bcr-Abl/T315I | 2.32 ± 0.68 | 1.88 ± 0.31 | 27.0 |

Conclusion:

It is evident from the results that compounds of the present invention exhibited significant inhibitory activity against Bcr-Abl mutated imatinib mesylate resistant cells.

EXAMPLE 63

Flow Cytometric Analysis

Effect of the Compounds of Present Invention in Bcr-Abl Mutated Imatinib Mesylate-Resistant Cell Lines on Cell Cycle and Apoptosis Using Flow Cytometry.

The assay was carried out as in reference, FEBS Letters, 2007, 581, 7, 1329-1334. Flow cytometry was used to study the effect of compounds of the present invention to induce apoptosis in Bcr-abl mutated imatinib mesylate resistant cell lines. Cells were seeded at a density of $10 \times 10^4$ cells/mL and incubated in an incubator with $3 \times IC_{50}$ concentration of compounds and vehicle control (untreated) for 48 h at 37° C. in the presence of 5% $CO_2$. The experiment was repeated with $5 \times IC_{50}$ concentration of compounds and vehicle control (untreated) for 48 h and 96 h at 37° C. in the presence of 5% $CO_2$. At the end of incubation, cells were harvested by centrifugation at 1000 rpm for 10 minutes, washed with phosphate buffered saline (PBS) and gradually resuspended in 70% ice-cold ethanol (to facilitate the permeablisation of stains). Cell suspension was stored for a minimum period of 4 h before staining with propidium iodide (PI). Fixed cells were stained with PI (80 μg/mL) in presence of RNase A (50 μg/mL), and read on Becton Dickinson FACS Calibur (USA) for cell cycle analysis. The results of this study are presented in Tables 4-6.

TABLE 4

Screening of (5X $IC_{50}$; 48 h time point) in imatinib mesylate resistant cell lines
% Apoptosis by Flow Cytometry Analysis
Compounds tested at 5X $IC_{50}$ (48 h time point)

| | K562 | Ba/F3 | T315I | E255V | Y253 |
|---|---|---|---|---|---|
| Control | 4.8 | 23.2 | 78.1 | 12.2 | 7 |
| imatinib mesylate | 3.9 | 40.3 | 4.3 | 96.7 | 78 |
| Compound of Example 3 | 12.7 | 46 | 97.6 | 91.2 | 87.5 |
| Compound of Example 4 | 12.2 | 46 | 98.2 | 93 | 89 |

TABLE 5

Screening of (3 X IC$_{50}$; 96 h time point) in imatinib
mesylate resistant cell lines
% Apoptosis by Flow Cytometry Analysis
Compounds tested at 3X IC$_{50}$ (96 h time point)

|  | K562 | Ba/F3 | T315I | E255V | Y253 |
|---|---|---|---|---|---|
| Control | 11 | 19.5 | 41.3 | 37.6 | 35.4 |
| Imatinib mesylate | 95 | 51 | 26.6 | 61 | 85.2 |
| Compound of Example 3 | 5 | 95 | 78 | 78 | 62 |
| Compound of Example 4 | 10 | 97 | 80.58 | 94.4 | 70.6 |

TABLE 6

Screening of (5X IC$_{50}$; 96 h time point) in imatinib
mesylate resistant cell lines
% Apoptosis by Flow Cytometry Analysis
Compounds tested at 5X IC$_{50}$ (96 h time point)

|  | K562 | Ba/F3 | T315I | E255V | Y253 |
|---|---|---|---|---|---|
| Control | 6.8 | 18.2 | 11 | 42.5 | 40 |
| imatinib mesylate | 92.6 | 31 | 25.2 | 98.4 | 98.2 |
| Compound of Example 3 | 3.4 | 84 | 85 | 90.9 | 94.9 |
| Compound of Example 4 | 5.2 | 93 | 63.9 | 97.4 | 96.6 |

Conclusion:

Induction of apoptosis by the compounds of the present invention in imatinib mesylate-resistant cell lines is significant.

EXAMPLE 64

TGFβ Assay

TGFβ is a prime candidate for maintaining the CML stem cells in a non-cycling state. An upregulation or prolongation of TGFβ signaling by Bcr-Abl suggests that one of the mechanisms by which Bcr-Abl promotes the transformation of haemopoietic progenitor cells, is by influencing the level of TGFβ signaling activity (FEBS Letters, 2007, 581, 7, 1329-1334). TGFβ plays a vital role in the preservation of the malignant progenitor population, and is partially responsible for the resistance to treatments targeting Bcr-Abl observed in a proportion of CML patients. Inhibition of TGFβ by the compounds of the present invention was demonstrated using Western Blot Analysis.

Western Blot Analysis

The Western Blot assay was carried out as in reference, Analytical Biochemistry, 1981, 112, 2, 195-203.

Western blot analysis was performed to decipher the mechanism of action of compounds of the present invention. Ba/F3 Bcr-Abl/T315I (imatinib mesylate resistant) cells were seeded in tissue culture grade 75 mm² flasks at a density of 2 to 4×10⁶ cells per flask. The cells were incubated in a humidified incubator for 2-4 h at 37° C. Subsequently, cells were treated with 3×IC$_{50}$ concentrations of the compounds or standard molecule (imatinib mesylate/dasatinib). Cells were then incubated for 72 h. Following the incubation, cells were harvested, washed with ice-cold phosphate buffered saline (PBS) and lysed with cold Cell Lytic buffer (Sigma Aldrich) supplemented with complete protease inhibitor cocktail (Roche, Germany). The protein extracts were obtained after centrifugation at 14,000 g at 4° C. (30 min). Aliquots of the resulting extracts were analyzed for their protein content using Bradford Reagent (Sigma) as per the manufacturer's instructions. In all the experiments, equivalent amounts of protein (70 µg) were loaded on 7.5%-10% Tris-glycine gels and resolved at 100 V for 2 h in a buffered solution (24.9 mM Tris base, 250 mM glycine, 0.1% SDS (sodium dodecyl sulfate)). After electrophoresis, the proteins were transferred from the gel to a polyvinylidene difluoride membrane (Sigma-Aldrich) at 25 V for 45 min. in transfer buffer (47.9 mM Tris base, 38.6 mM glycine, 0.037% SDS, 20% methanol; pH 9.2-9.4). Blots were blocked in Tris-buffered saline (TBS) (20 mM Tris base, 0.9% NaCl; pH 7.4) containing 5% nonfat dry milk (Santa Cruz Biotechnology, USA) for 2 h at room temperature, and incubated with gentle rocking after addition of the primary antibody which was prepared in TBS at 4° C. for a time ranging from 16-18 h. Primary antibodies included antibodies against TGFβ, Smad2/3, phospho-Smad2/3 (Cell Signaling) and β-Actin (Cell Signaling). Following the incubation, membranes were washed and then probed with horse-radish peroxidase (HRP)-conjugated secondary antibody. Bands were visualized using chemiluminescent peroxidase substrate (Pierce, Ill.) and a Kodak Imaging station. Blots were stripped with stripping buffer (50 mM Tris-HCl pH 6.8, 1% SDS and 100 mM β-mercaptoethanol) for 30 min at 55° C., washed and re-probed with a primary antibody to the housekeeping protein. β-actin was used as a loading control.

Figure 3:
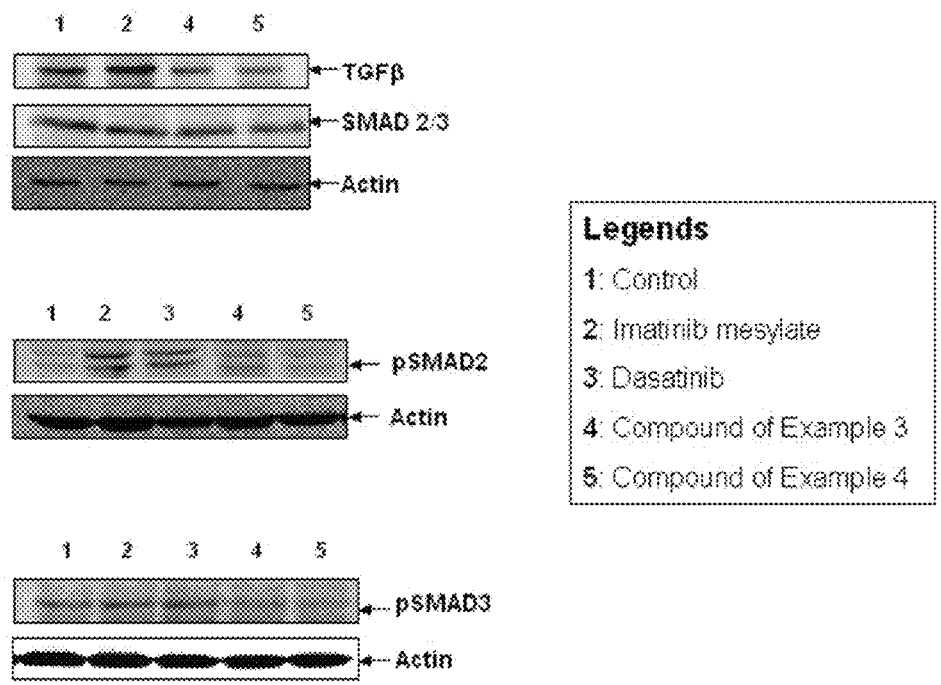
FIG. 3 elucidates the mechanism of action of compounds of the present invention in imatinib mesylate resistant T315I cell line.

The results are depicted in FIG. 3.

Conclusion:

Compound of Example 3 and Compound of Example 4 strongly downregulated p-Smad2 and p-Smad3, effector target molecules of TGFβ signaling, indicating their role in inhibiting the TGFβ pathway in imatinib mesylate/dasatinib resistant cell line, T315I.

EXAMPLE 65

Inhibition of Autophosphorylation of Bcr-Abl Protein

Bcr-Abl protein autophosphorylation at Tyr-245 is involved in the activation mechanism of the kinase (Leukemia Research, 2008, 32, 936-943). The assay was carried out using Western blot analysis according to the reference, Analytical Biochemistry, 1981, 112, 2, 195-203, with certain modifications.

Western Blot Analysis

Figure 4:
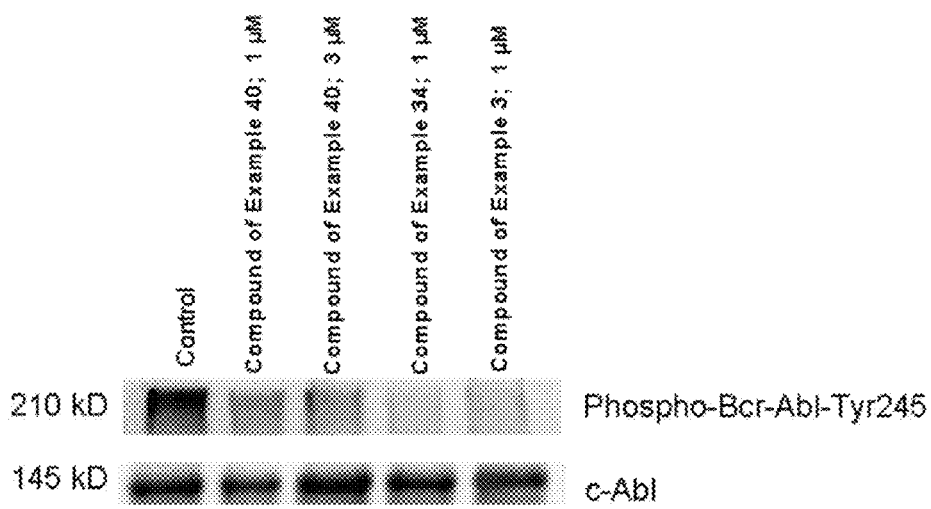
FIG. 4 shows the effect of compounds of the present invention on autophosphorylation of Bcr-Abl protein.

Western blot analysis was performed to decipher the mechanism of action of compounds of the present invention. Ba/F3 Bcr-Abl/T315I (imatinib mesylate resistant) cells were seeded in tissue culture grade 75 mm² flasks at a density of 2 to 4×10⁶ cells per flask. The cells were incubated in a humidified incubator for 2-4 h at 37° C. Subsequently, cells were treated with respective concentrations of the compounds. Cells were then incubated for 72 h. Following the incubation, cells were harvested, washed with ice-cold phosphate buffered saline (PBS) and lysed with cold Cell Lytic buffer (Sigma Aldrich) supplemented with complete protease inhibitor cocktail (Roche, Germany). The protein extracts were obtained after centrifugation at 14,000 rpm at 4° C. (30 min). Aliquots of the resulting extracts were analyzed for their protein content using Bradford Reagent (Sigma) as per the manufacturer's instructions. Aliquots containing 500 µg protein were used for immunoprecipitation using c-Abl antibody (Santacruz Biotechnology, USA) and protein A-sepharose beads. The precipitated protein were loaded on 7.5% Tris-glycine gels and resolved at 100 V for 2 h in a buffered solution (24.9 mM Tris base, 250 mM glycine, 0.1% SDS (sodium dodecyl sulfate)). After electrophoresis, the proteins were transferred from the gel to a polyvinylidene difluoride membrane (Sigma-Aldrich) at 70 V for 1.5 h in transfer buffer (47.9 mM Tris base, 38.6 mM glycine, 0.037% SDS, 20% methanol; pH 9.2-9.4) using wet transfer method. Blots were blocked in TBST (Tris-buffered saline (TBS) (20 mM Tris base, 0.9% NaCl; pH 7.4) with 0.1% Tween 20 (Sigma Aldrich, USA)) containing 5% nonfat dry milk (Santa Cruz Biotechnology, USA) for 2 h at room temperature, and incubated with gentle rocking after addition of the primary antibody which was prepared in TBST at 4° C. for a time ranging from 16-18 h. Primary antibodies included antibodies phospho-Bcr-abl-Tyr245 (Cell Signaling Technology) and c-Abl (Santacruz Biotechnology, USA). Following the incubation, membranes were washed and then probed with horse-radish peroxidase. (HRP)-conjugated secondary antibody (Santacruz Biotechnology). Bands were visualized using chemiluminescent peroxidase substrate (Pierce, Ill.) and a Kodak Imaging station. The results are depicted in FIG. 4.

Conclusion:

The compounds of the present invention downregulated autophosphorylation of Bcr-abl protein in imatinib mesylate/dasatinib resistant cell line, T315I.

EXAMPLE 66

Inhibition of Phosphorylation of CRKL Protein

Phospho-CRKL monitoring has been recognized as a prognostic marker in CML patients treated with first and second generation Bcr-Abl inhibitors (Haematologica, 2008, 93, 5, 765-769). The assay was carried out using Western blot analysis according to the reference, Analytical Biochemistry, 1981, 112, 2, 195-203, with certain modifications.

Western Blot Analysis

Western blot analysis was performed to decipher the mechanism of action of compounds of the present invention. Ba/F3 Bcr-Abl/T315I (imatinib mesylate resistant) cells were seeded in tissue culture grade 75 mm² flasks at a density of 2 to 4×10⁶ cells per flask. The cells were incubated in a humidified incubator for 2-4 h at 37° C. Subsequently, cells were treated with respective concentrations of the compounds. Cells were then incubated for 72 h. Following the incubation, cells were harvested, washed with ice-cold phosphate buffered saline (PBS) and lysed with cold Cell Lytic buffer (Sigma Aldrich) supplemented with complete protease inhibitor cocktail (Roche, Germany). The protein extracts were obtained after centrifugation at 14,000 rpm at 4° C. (30 min). Aliquots of the resulting extracts were analyzed for their protein content using Bradford Reagent (Sigma) as per the manufacturer's instructions. Equivalent protein samples (70 μg) were loaded on 10% Tris-glycine gels and resolved at 100 V for 2 h in a buffered solution (24.9 mM Tris base, 250 mM glycine, 0.1% SDS (sodium dodecyl sulfate)). After electrophoresis, the proteins were transferred from the gel to a polyvinylidene difluoride membrane (Sigma-Aldrich) at 70 V for 1.5 h in transfer buffer (47.9 mM Tris base, 38.6 mM glycine, 0.037% SDS, 20% methanol; pH 9.2-9.4) using wet transfer method. Blots were blocked in TBST (Tris-buffered saline (TBS) (20 mM Tris base, 0.9% NaCl; pH 7.4) with 0.1% Tween 20 (Sigma Aldrich, USA)) containing 5% nonfat dry milk (Santa Cruz Biotechnology, USA) for 2 h at room temperature, and incubated with gentle rocking after addition of the primary antibody which was prepared in TBST at 4° C. for a time ranging from 16-18 h. Primary antibodies used were phospho-CRKL-Tyr-207 (Cell Signaling Technology) and β-actin (Sigma Aldrich, USA). Following the incubation, membranes were washed and then probed with horse-radish peroxidase (HRP)-conjugated secondary antibody (Santacruz Biotechnology, USA). Bands were visualized using chemiluminescent peroxidase substrate (Pierce, Ill.) and a Kodak Imaging station.

Figure 5:
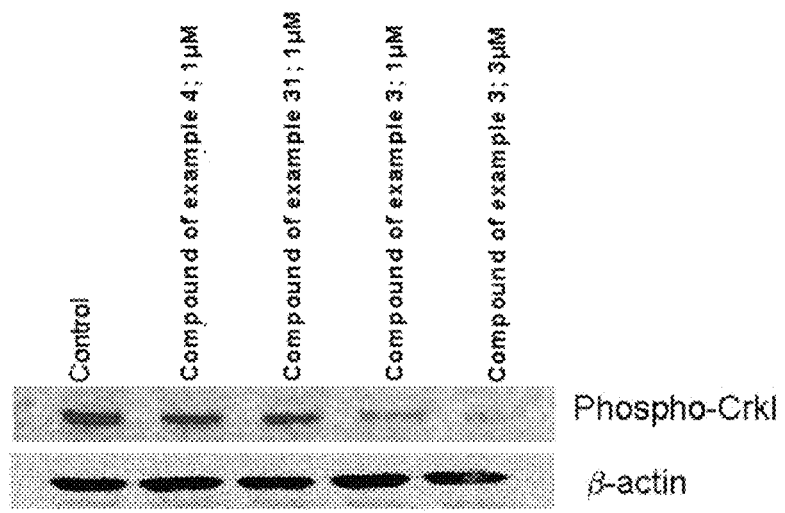
FIG. 5 shows the CRKL phosphorylation analysis of imatinib resistant CML cells (E255V) on treatment with compounds of the present invention.
Figure 6A:
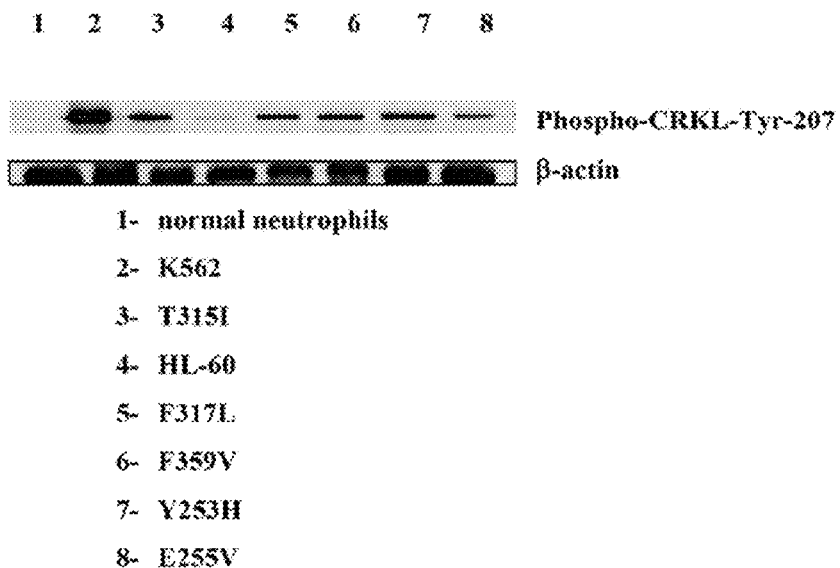
FIG. 6A shows the basal levels of phospho-CRKL (Tyr 207) in normal neutrophils and CML cell lines
Figure 6B:
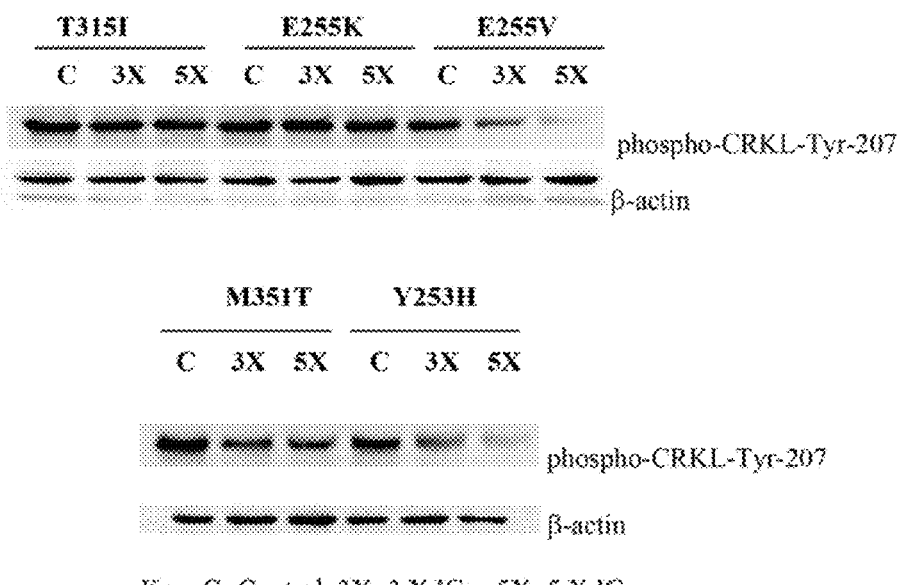
FIG. 6B shows the CRKL phosphorylation analysis of imatinib resistant CML cells on treatment with compound of Example 3.

The results are depicted in FIG. 5 and FIG. 68.

Conclusion:

The compounds of the present invention downregulated phosphorylation of CRKL protein in imatinib mesylate resistant P loop mutant cell line, E255V in a dose-dependent manner.

The compound of Example 3 was found to inhibit phospho-CRKL in three other mutant cell lines (E255V, M351T and Y253H).

EXAMPLE 67

In-Vivo Efficacy Testing of the Compounds of the Present Invention in Imatinib-Resistant and Imatinib-Sensitive Tumor Models was Studied by Using Cell Lines Such as Ba/F3 Transfectants Expressing Full-Length Wild Type Bcr-Abl (Ba/F3 Bcr-Abl/WT) or Mutated Bcr-Abl (Ba/F3 Bcr-Abl/T315I)

Objective:

In-vivo efficacy testing of compounds of the present invention in imatinib resistant and imatinib sensitive tumor models was carried out according to the reference Cancer Research, 2002, 62, 7149-7153.

Cell Lines:

Cell lines Ba/F3 transfectants expressing full-length wild type imatinib sensitive (Ba/F3 Bcr-Abl/WT) or mutated imatinib resistant (Ba/F3 Bcr-Abl/T315I) were used in this study. These recombinant cell lines were licensed from Dr. Brian Druker's laboratory, Howard Hughes Medical Institute, Oregon Health and Science University Cancer Institute, Portland, Oreg., USA.

Compound Storage:

The compounds of the present invention including standard were stored at 4-8° C. in an amber colored bottle. The compounds in solutions were also maintained at 4-8° C. in a refrigerator. Sample for animal injection was made fresh everyday, residual volume were pooled and discarded as per standard operating procedure (SOP) for chemical disposals.

Dose Preparation:

Required compound was weighed and admixed with 0.5% (w/v) carboxymethylcellulose (CMC) and triturated with Tween-20 (*secundum artum*) with gradual addition of water to make up the final concentration. Imatinib mesylate was used as a standard.

Efficacy Study in SCID Mice:

A group of 110 Severely Combined Immune-Deficient (SCID strain-CBySmn.CB17-Prkdc$^{scid}$/J, The Jackson Laboratory, Stock #001803) male mice, 5-6 weeks old, weighing ~20 g, were used.

All animal experiments were carried out in accordance with the guidelines of Committee for the Purpose of Control and Supervision of Experiments on Animals (CPCSEA). All animal experiments were approved by Institutional Animal Ethics Committee (IAEC) of Piramal Life Sciences Limited, Goregaon East, Mumbai, India.

Ba/F3 Bcr-Abl/WT cells and Ba/F3 Bcr-Abl/T315I cells were grown in RPMI1640 medium containing 10% fetal calf serum in 5% CO$_2$ incubator at 37° C. Cells were pelleted by centrifugation at 1000-rpm for 10 minutes. Cells were resuspended in saline to get a count of 80-100×10⁶ cells per mL, 0.2 mL of this cell suspension was injected by subcutaneous (s.c.) route in SCID mice. Mice were observed alternate days for palpable tumor mass. Once the tumor size reached a size of 5-7 mm in diameter, animals were randomized into respective treatment groups. Dose of control or test compound was administered every day. Tumor size was recorded at 2-5 day intervals. Tumor weight (mg) was estimated according to the formula for a prolate ellipsoid: {Length (mm)× [width (mm)²]×0.5} assuming specific gravity to be one and π to be three. Tumor growth in compound treated animals is calculated as T/C (Treated/Control)×100% and Growth inhibition Percent (GI %) was [100–T/C %]. Respective treatment groups are presented in Table 7. Results are presented in Table 8.

TABLE 7

Treatment groups in the xenograft models (SET I and SET II)

| Groups | Sample | Dose | Route | Number of treatments | n |
|---|---|---|---|---|---|
| (SET I) Designation: Ba/F3 Bcr-Abl/T315I | | | | | |
| I | Control (untreated) | Vehicle | p.o. | q1d X 12 | 7 |
| II | Compound of Example 3 | 200 mg/kg | p.o. | q1d X 12 | 7 |
| III | Compound of Example 4 | 200 mg/kg | p.o. | q1d X 12 | 7 |
| IV | Imatinib Mesylate | 200 mg/kg | p.o. | q1d X 12 | 7 |
| (SET II) Designation: Ba/F3 Bcr-Abl/WT | | | | | |
| I | Control (untreated) | Vehicle | p.o. | q1d X 12 | 10 |
| II | Compound of Example 3 | 200 mg/kg | p.o. | q1d X 12 | 10 |
| III | Compound of Example 4 | 200 mg/kg | p.o. | q1d X 12 | 10 |
| IV | Imatinib Mesylate | 200 mg/kg | p.o. | q1d X 12 | 10 | p.o. = per oral;
n = number of animals
q1d X 12 = single administration for 12 days

TABLE 8

Tumor growth inhibition percent (% GI) for compounds of the present invention in imatinib mesylate sensitive (Ba/F3 Bcr-Abl/WT) and resistant cell lines (Ba/F3 Bcr-Abl/T315I).

| Compounds | Dose b.i.d. (mpk) | Ba/F3 Bcr-Abl/T315I % GI | Ba/F3 Bcr-Abl/WT % GI |
|---|---|---|---|
| Compound of Example 3 | 200 | 54 | 63 |
| Compound of Example 4 | 200 | 65 | 36 |

Imatinib mesylate is inactive at 200 mpk b.i.d. in Ba/F3 Bcr-Abl/T315I (% GI < 15)

CONCLUSION

Figure 7:
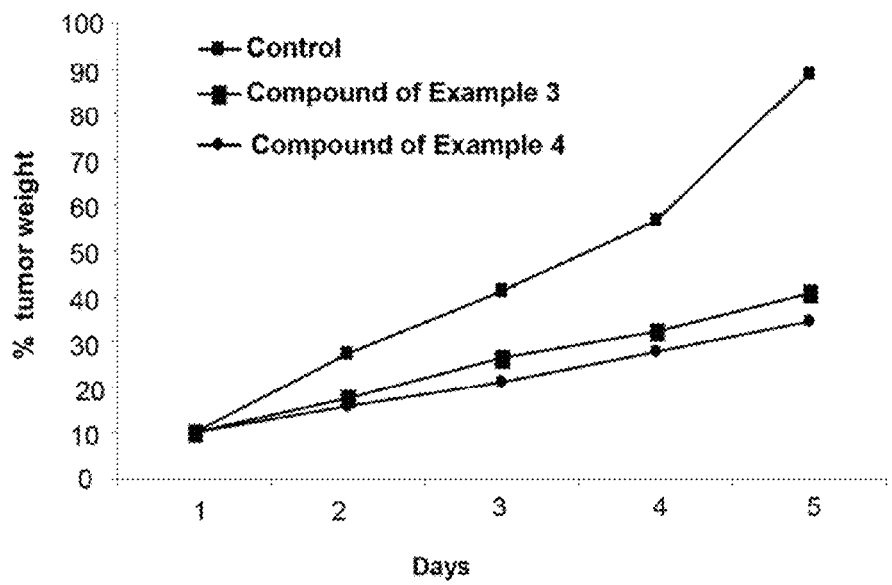
FIG. 7 shows the relative tumor weight profile for compounds of the present invention in imatinib mesylate resistant T315I cell line.
Figure 8:
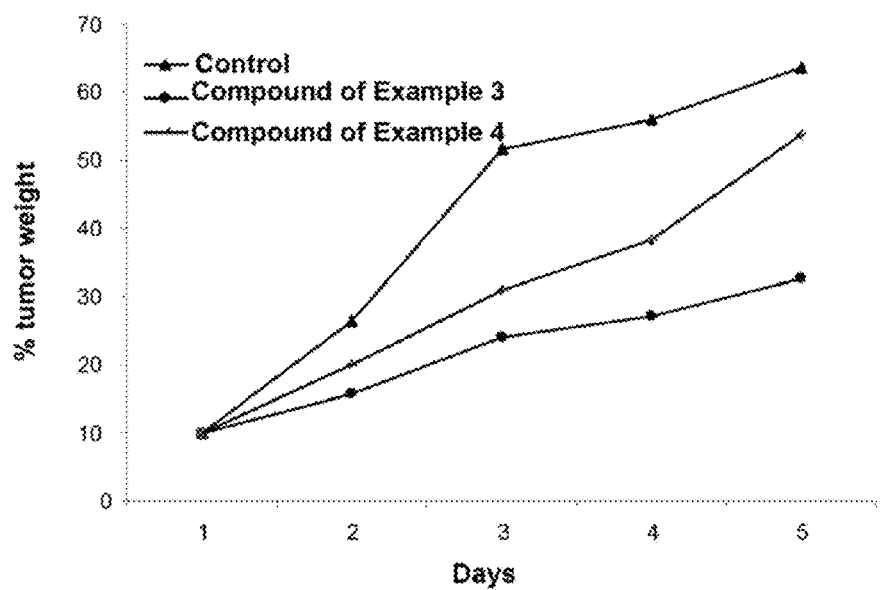
FIG. 8 shows the relative tumor weight profile for compounds of the present invention in imatinib mesylate sensitive cell line (Ba/F3).

The data presented in FIG. 7 and FIG. 8 demonstrates that the compounds of the present invention exhibited significantly greater in-vivo efficacy than imatinib mesylate in inhibiting the most predominant mutated form of Bcr-Abl i.e. Ba/F3 Bcr-Abl/T315I when tested at the same doses as that of wild type Bcr-Abl expressing xenograft i.e. Ba/F3 Bcr-Abl/ WT.

It should be noted that, as used in this specification and the appended claims, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:
1. A compound of formula I,

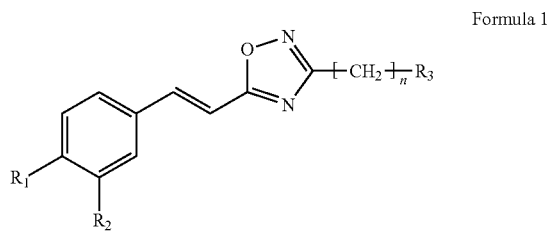

Formula 1 wherein,
$R_1$ is selected from hydroxy, $(C_1$-$C_{12})$-alkoxy or aryloxy;
$R_2$ is selected from hydroxy, nitro, $(C_1$-$C_{12})$-alkoxy, aryloxy, NH—SO₂—$(C_1$-$C_{12})$-alkyl, NH—SO₂-aryl and $NR_aR_b$; $R_3$ is selected from hydrogen, $(C_1$-$C_{12})$-alkyl, $(C_3$-$C_{12})$-cycloalkyl, aralkyl, aryl or heterocyclyl; and
n is an integer from 0-3;
wherein,
$(C_1$-$C_{12})$-alkyl is unsubstituted or substituted with one or more groups selected from halogen, hydroxy, cyano, nitro, $(C_1$-$C_{12})$-alkoxy, unsubstituted or substituted aryl, unsubstituted or substituted heterocyclyl, $COOR_a$, $C(O)R_a$, $SR_a$ and $C(O)NR_aR_b$;
alkyl of $(C_1$-$C_{12})$-alkoxy is unsubstituted or substituted with one or more groups selected from halogen, hydroxy, cyano, nitro, unsubstituted or substituted aryl, unsubstituted or substituted heterocyclyl, $COOR_a$, $C(O)R_a$, $SR_a$ and $C(O)NR_aR_b$;
$(C_3$-$C_{12})$-cycloalkyl is unsubstituted or substituted with one or more groups selected from halogen, hydroxy, cyano, nitro, unsubstituted or substituted $(C_1$-$C_{12})$-alkyl, $(C_1$-$C_{12})$-alkoxy, unsubstituted or substituted aryl, unsubstituted or substituted heterocyclyl, $COOR_a$, $C(O)R_a$, $SR_a$, $NR_aR_b$ and $C(O)NR_aR_b$;
aryl is unsubstituted or substituted with one or more groups selected from halogen, hydroxy, cyano, nitro, $(C_1$-$C_{12})$-alkyl, $(C_2$-$C_{12})$-alkenyl, $(C_2$-$C_{12})$-alkynyl, $(C_1$-$C_{12})$-alkoxy, unsubstituted or substituted heterocyclyl, $COOR_a$, $C(O)R_a$, $SR_a$, $NR_aR_b$ and $C(O)NR_aR_b$;
aryl of aryloxy is unsubstituted or substituted with one or more groups selected from halogen, hydroxy, cyano, nitro, unsubstituted or substituted $(C_1$-$C_{12})$-alkyl, $(C_2$-$C_{12})$-alkenyl, $(C_2$-$C_{12})$-alkynyl, unsubstituted or substituted heterocyclyl, $COOR_a$, $C(O)R_a$, $SR_a$, $NR_aR_b$ and $C(O)NR_aR_b$;
aryl of aralkyl is unsubstituted or substituted with one or more groups selected from halogen, hydroxy, cyano, nitro, unsubstituted or substituted $(C_1-C_{12})$-alkyl, $(C_2-C_{12})$-alkenyl, $(C_2-C_{12})$-alkynyl and unsubstituted or substituted heterocyclyl;

heterocyclyl is unsubstituted or substituted with one or more groups selected from halogen, hydroxy, cyano, nitro, unsubstituted or substituted $(C_1-C_{12})$-alkyl, $(C_1-C_{12})$-alkoxy, unsubstituted or substituted aralkyl, unsubstituted or substituted aryl, $COOR_a$, $C(O)R_a$, $SR_a$, $NR_aR_b$, $(C_1-C_{12})$-alkyl-$NR_aR_b$ and $C(O)NR_aR_b$; and $R_a$ and $R_b$ are independently selected from hydrogen, $(C_1-C_{12})$-alkyl, aralkyl, aryl or heterocyclyl;

with a proviso that when n is 0, $R_3$ is other than aryl or heterocyclyl;

or a stereoisomer, tautomer, pharmaceutically acceptable salt or pharmaceutically acceptable polymorph thereof.

2. The compound according to claim 1,
wherein,
$R_1$ is selected from hydroxy, $(C_1-C_{12})$-alkoxy or aryloxy;
$R_2$ is selected from hydroxy, $(C_1-C_{12})$-alkoxy or aryloxy;
$R_3$ is selected from hydrogen, $(C_1-C_{12})$-alkyl, $(C_3-C_{12})$-cycloalkyl, aralkyl, aryl or heterocyclyl; and
n is an integer from 0-3;
wherein,
$(C_1-C_{12})$-alkyl is unsubstituted or substituted with one or more groups selected from halogen, hydroxy, cyano, nitro, unsubstituted or substituted aryl and unsubstituted or substituted heterocyclyl;
alkyl of $(C_1-C_{12})$-alkoxy is unsubstituted or substituted with one or more groups selected from halogen, hydroxy, cyano, nitro, unsubstituted or substituted aryl and unsubstituted or substituted heterocyclyl;
$(C_3-C_{12})$-cycloalkyl is unsubstituted or substituted with one or more groups selected from halogen, hydroxy, cyano, nitro, unsubstituted or substituted $(C_1-C_{12})$-alkyl, unsubstituted or substituted aryl and unsubstituted or substituted heterocyclyl;
aryl is unsubstituted or substituted with one or more groups selected from halogen, hydroxy, cyano, nitro, unsubstituted or substituted $(C_1-C_{12})$-alkyl, unsubstituted or substituted $(C_2-C_{12})$-alkenyl, unsubstituted or substituted $(C_2-C_{12})$-alkynyl and unsubstituted or substituted heterocyclyl;
aryl of aryloxy is unsubstituted or substituted with one or more groups selected from halogen, hydroxy, cyano, nitro, unsubstituted or substituted $(C_1-C_{12})$-alkyl, unsubstituted or substituted $(C_2-C_{12})$-alkenyl, unsubstituted or substituted $(C_2-C_{12})$-alkynyl and unsubstituted or substituted heterocyclyl;
aryl of aralkyl is unsubstituted or substituted with one or more groups selected from halogen, hydroxy, cyano, nitro, unsubstituted or substituted $(C_1-C_{12})$-alkyl, unsubstituted or substituted $(C_2-C_{12})$-alkenyl, unsubstituted or substituted $(C_2-C_{12})$-alkynyl and unsubstituted or substituted heterocyclyl;
heterocyclyl is unsubstituted or substituted with one or more groups selected from halogen, hydroxy, cyano, nitro, unsubstituted or substituted $(C_1-C_{12})$-alkyl, $(C_1-C_{12})$-alkoxy, unsubstituted or substituted aralkyl, unsubstituted or substituted aryl, $COOR_a$, $C(O)R_a$, $NR_aR_b$ and $(C_1-C_{12})$-alkyl-$NR_aR_b$; and
$R_a$ and $R_b$ are independently selected from hydrogen, $(C_1-C_{12})$ alkyl, aralkyl, aryl or heterocyclyl;
with a proviso that when n is 0, $R_3$ is other than aryl or heterocyclyl;
or a stereoisomer, tautomer, pharmaceutically acceptable salt or pharmaceutically acceptable polymorph thereof.

3. The compound according to claim 2,
wherein,
$R_1$ is hydroxy or $(C_1-C_{12})$-alkoxy;
$R_2$ is hydroxy or $(C_1-C_{12})$-alkoxy;
$R_3$ is hydrogen or $(C_1-C_{12})$-alkyl; and
n is 0 or 1;
wherein,
$(C_1-C_{12})$-alkyl is unsubstituted or substituted with one or more groups selected from halogen, hydroxy, cyano, nitro, unsubstituted or substituted aryl and unsubstituted or substituted heterocyclyl;
alkyl of $(C_1-C_{12})$-alkoxy is unsubstituted or substituted with one or more groups selected from halogen, hydroxy, cyano, nitro, unsubstituted or substituted aryl and unsubstituted or substituted heterocyclyl;
aryl is unsubstituted or substituted with one or more groups selected from halogen, hydroxy, cyano, nitro, unsubstituted or substituted $(C_1-C_{12})$-alkyl and unsubstituted or substituted heterocyclyl;
heterocyclyl is unsubstituted or substituted with one or more groups selected from halogen, hydroxy, cyano, nitro, unsubstituted or substituted $(C_1-C_{12})$-alkyl, unsubstituted or substituted aralkyl, unsubstituted or substituted aryl, $COOR_a$, $C(O)R_a$, $NR_aR_b$ and $(C_1-C_{12})$-alkyl-$NR_aR_b$; and
$R_a$ and $R_b$ are independently selected from hydrogen, $(C_1-C_{12})$ alkyl, aralkyl, aryl or heterocyclyl;
or a stereoisomer, tautomer, pharmaceutically acceptable salt or pharmaceutically acceptable polymorph thereof.

4. The compound according to claim 3,
wherein,
$R_1$ is hydroxy or unsubstituted $(C_1-C_{12})$-alkoxy;
$R_2$ is hydroxy or unsubstituted $(C_1-C_{12})$-alkoxy;
$R_3$ is hydrogen or unsubstituted $(C_1-C_{12})$-alkyl; and
n is 0 or 1;
or a stereoisomer, tautomer, pharmaceutically acceptable salt or pharmaceutically acceptable polymorph thereof.

5. The compound according to claim 2,
wherein,
$R_1$ is hydroxy or $(C_1-C_{12})$-alkoxy;
$R_2$ is hydroxy or $(C_1-C_{12})$-alkoxy;
$R_3$ is $(C_3-C_{12})$-cycloalkyl; and
n is 0 or 1;
wherein,
alkyl of $(C_1-C_{12})$-alkoxy is unsubstituted or substituted with one or more groups selected from halogen, hydroxy, cyano, nitro, unsubstituted or substituted aryl and unsubstituted or substituted heterocyclyl;
$(C_3-C_{12})$-cycloalkyl is unsubstituted or substituted with one or more groups selected from halogen, hydroxy, cyano, nitro, unsubstituted or substituted $(C_1-C_{12})$-alkyl, unsubstituted or substituted aryl and unsubstituted or substituted heterocyclyl;
aryl is unsubstituted or substituted with one or more groups selected from halogen, hydroxy, cyano, nitro, unsubstituted or substituted $(C_1-C_{12})$-alkyl and unsubstituted or substituted heterocyclyl;
aryl of aralkyl is unsubstituted or substituted with one or more groups selected from halogen, hydroxy, cyano, nitro, unsubstituted or substituted $(C_1-C_{12})$-alkyl, unsubstituted or substituted $(C_2-C_{12})$-alkenyl, unsubstituted or substituted $(C_2-C_{12})$-alkynyl and unsubstituted or substituted heterocyclyl;
heterocyclyl is unsubstituted or substituted with one or more groups selected from halogen, hydroxy cyano, nitro, unsubstituted or substituted $(C_1-C_{12})$-alkyl, unsubstituted or substituted aralkyl, unsubstituted or substituted aryl, $COOR_a$, $C(O)R_a$, $NR_aR_b$ and $(C_1\text{-}C_{12})$-alkyl-$NR_aR_b$; and $R_a$ and $R_b$ are independently selected from hydrogen, $(C_1\text{-}C_{12})$ alkyl, aralkyl, aryl or heterocyclyl;

or a stereoisomer, tautomer, pharmaceutically acceptable salt, pharmaceutically acceptable solvate or pharmaceutically acceptable polymorph thereof.

6. The compound according to claim 5, wherein, $R_1$ is hydroxy or unsubstituted $(C_1\text{-}C_{12})$-alkoxy;
$R_2$ is hydroxy or unsubstituted $(C_1\text{-}C_{12})$-alkoxy;
$R_3$ is unsubstituted $(C_3\text{-}C_{12})$-cycloalkyl; and
n is 0 or 1;

or a stereoisomer, tautomer, pharmaceutically acceptable salt or pharmaceutically acceptable polymorph thereof.

7. The compound according to claim 2, wherein, $R_1$ is hydroxy or $(C_1\text{-}C_{12})$-alkoxy;
$R_2$ is hydroxy or $(C_1\text{-}C_{12})$-alkoxy;
$R_3$ is aryl; and
n is 1;
wherein, $(C_1\text{-}C_{12})$-alkyl is unsubstituted or substituted with one or more groups selected from halogen, hydroxy, cyano, nitro, unsubstituted or substituted aryl and unsubstituted or substituted heterocyclyl;

alkyl of $(C_1\text{-}C_{12})$-alkoxy is unsubstituted or substituted with one or more groups selected from halogen, hydroxy, cyano, nitro, unsubstituted or substituted aryl and unsubstituted or substituted heterocyclyl;

aryl is unsubstituted or substituted with one or more groups selected from halogen, hydroxy, cyano, nitro, unsubstituted or substituted $(C_1\text{-}C_{12})$-alkyl and unsubstituted or substituted heterocyclyl;

aryl of aralkyl is unsubstituted or substituted with one or more groups selected from halogen, hydroxy, cyano, nitro, unsubstituted or substituted $(C_1\text{-}C_{12})$-alkyl, unsubstituted or substituted $(C_2\text{-}C_{12})$-alkenyl, unsubstituted or substituted $(C_2\text{-}C_{12})$-alkynyl and unsubstituted or substituted heterocyclyl;

heterocyclyl is unsubstituted or substituted with one or more groups selected from halogen, hydroxy, cyano, nitro, unsubstituted or substituted $(C_1\text{-}C_{12})$-alkyl, unsubstituted or substituted aralkyl, unsubstituted or substituted aryl, $COOR_a$, $C(O)R_a$, $NR_aR_b$ and $(C_1\text{-}C_{12})$-alkyl-$NR_aR_b$; and $R_a$ and $R_b$ are independently selected from hydrogen, $(C_1\text{-}C_{12})$ alkyl, aralkyl, aryl and heterocyclyl;

or a stereoisomer, tautomer, pharmaceutically acceptable salt or pharmaceutically acceptable polymorph thereof.

8. The compound according to claim 7, wherein, $R_1$ is hydroxy or unsubstituted $(C_1\text{-}C_{12})$-alkoxy;
$R_2$ is hydroxy or unsubstituted $(C_1\text{-}C_{12})$-alkoxy;
$R_3$ is phenyl; and
n is 1;

or a stereoisomer, tautomer, pharmaceutically acceptable salt or pharmaceutically acceptable polymorph thereof.

9. The compound according to claim 2, wherein, $R_1$ is hydroxy or $(C_1\text{-}C_{12})$-alkoxy;
$R_2$ is hydroxy or $(C_1\text{-}C_{12})$-alkoxy;
$R_3$ is heterocyclyl; and
n is 1;
wherein, $(C_1\text{-}C_{12})$-alkyl is unsubstituted or substituted with one or more groups selected from halogen, hydroxy, cyano, nitro, unsubstituted or substituted aryl and unsubstituted or substituted heterocyclyl;

alkyl of $(C_1\text{-}C_{12})$-alkoxy is unsubstituted or substituted with one or more groups selected from halogen, hydroxy, cyano, nitro, unsubstituted or substituted aryl and unsubstituted or substituted heterocyclyl;

aryl is unsubstituted or substituted with one or more groups selected from halogen, hydroxy, cyano, nitro, unsubstituted or substituted $(C_1\text{-}C_{12})$-alkyl and unsubstituted or substituted heterocyclyl;

aryl of aralkyl is unsubstituted or substituted with one or more groups selected from halogen, hydroxy, cyano, nitro, unsubstituted or substituted $(C_1\text{-}C_{12})$-alkyl, unsubstituted or substituted $(C_2\text{-}C_{12})$-alkenyl, unsubstituted or substituted $(C_2\text{-}C_{12})$-alkynyl and unsubstituted or substituted heterocyclyl;

heterocyclyl is unsubstituted or substituted with one or more groups selected from halogen, hydroxy, cyano, nitro, unsubstituted or substituted $(C_1\text{-}C_{12})$-alkyl, unsubstituted or substituted aralkyl, unsubstituted or substituted aryl, $COOR_a$, $C(O)R_a$, $NR_aR_b$ and $(C_1\text{-}C_{12})$-alkyl-$NR_aR_b$; and $R_a$ and $R_b$ are independently selected from hydrogen, $(C_1\text{-}C_{12})$ alkyl, aralkyl, aryl or heterocyclyl;

or a stereoisomer, tautomer, pharmaceutically acceptable salt or pharmaceutically acceptable polymorph thereof.

10. The compound according to claim 9, wherein, $R_1$ is hydroxy or unsubstituted $(C_1\text{-}C_{12})$-alkoxy;
$R_2$ is hydroxy or unsubstituted $(C_1\text{-}C_{12})$-alkoxy;
$R_3$ is heterocyclyl; and
n is 1;
wherein, heterocyclyl is unsubstituted or substituted with one or more groups selected from halogen, $(C_1\text{-}C_{12})$-alkyl, unsubstituted or substituted aralkyl, $COOR_a$, $NR_aR_b$ and $(C_1\text{-}C_{12})$-alkyl-$NR_aR_b$; and $R_a$ and $R_b$ are independently selected from hydrogen, $(C_1\text{-}C_{12})$ alkyl, aralkyl, aryl or heterocyclyl;

or a stereoisomer, tautomer, pharmaceutically acceptable salt or pharmaceutically acceptable polymorph thereof.

11. The compound according to claim 10, wherein, $R_1$ is hydroxy or unsubstituted $(C_1\text{-}C_{12})$-alkoxy;
$R_2$ is hydroxy or unsubstituted $(C_1\text{-}C_{12})$-alkoxy;
$R_3$ is piperidine or pyridine; and
n is 1;
wherein, piperidine is unsubstituted or substituted with one or more groups selected from halogen, $(C_1\text{-}C_{12})$-alkyl, unsubstituted or substituted aralkyl, $COOR_a$, $NR_aR_b$ and $(C_1\text{-}C_{12})$-alkyl-$NR_aR_b$; and $R_a$ and $R_b$ are independently selected from hydrogen, $(C_1\text{-}C_{12})$ alkyl, aralkyl, aryl and heterocyclyl;

or a stereoisomer, tautomer, pharmaceutically acceptable salt or pharmaceutically acceptable polymorph thereof.

12. The compound according to claim 1, wherein, $R_1$ is hydroxy or $(C_1\text{-}C_{12})$-alkoxy;
$R_2$ is selected from nitro, $NH\text{—}SO_2\text{—}(C_1\text{-}C_{12})$-alkyl, $NH\text{—}SO_2$-aryl or $NR_aR_b$;
$R_3$ is selected from hydrogen, $(C_1\text{-}C_{12})$-alkyl, $(C_3\text{-}C_{12})$-cycloalkyl, aralkyl, aryl or heterocyclyl; and
n is an integer from 0-3;

wherein,
($C_1$-$C_{12}$)-alkyl is unsubstituted or substituted with one or more groups selected from halogen, hydroxy, cyano, nitro, unsubstituted or substituted aryl and unsubstituted or substituted heterocyclyl;
alkyl of ($C_1$-$C_{12}$)-alkoxy is unsubstituted or substituted with one or more groups selected from halogen, hydroxy, cyano, nitro, unsubstituted or substituted aryl and unsubstituted or substituted heterocyclyl;
($C_3$-$C_{12}$)-cycloalkyl is unsubstituted or substituted with one or more groups selected from halogen, hydroxy, cyano, nitro, unsubstituted or substituted ($C_1$-$C_{12}$)-alkyl, ($C_1$-$C_{12}$)-alkoxy, unsubstituted or substituted aryl, unsubstituted or substituted heterocyclyl, $COOR_a$, $C(O)R_a$, $SR_a$, $NR_aR_b$ and $C(O)NR_aR_b$;
aryl is unsubstituted or substituted with one or more groups selected from halogen, hydroxy, cyano, nitro, unsubstituted or substituted ($C_1$-$C_{12}$)-alkyl and unsubstituted or substituted heterocyclyl;
aryl of aralkyl is unsubstituted or substituted with one or more groups selected from halogen, hydroxy, cyano, nitro, unsubstituted or substituted ($C_1$-$C_{12}$)-alkyl, unsubstituted or substituted ($C_2$-$C_{12}$)-alkenyl, unsubstituted or substituted ($C_2$-$C_{12}$)-alkynyl and unsubstituted or substituted heterocyclyl;
heterocyclyl is unsubstituted or substituted with one or more groups selected from halogen, hydroxy, cyano, nitro, unsubstituted or substituted ($C_1$-$C_{12}$)-alkyl, unsubstituted or substituted aralkyl, unsubstituted or substituted aryl, $COOR_a$, $C(O)R_a$, $NR_aR_b$ and ($C_1$-$C_{12}$)-alkyl-$NR_aR_b$; and
$R_a$ and $R_b$ are independently selected from hydrogen, ($C_1$-$C_{12}$) alkyl, aralkyl, aryl or heterocyclyl;
with a proviso that when n is 0, $R_3$ is other than aryl or heterocyclyl;
or a stereoisomer, tautomer, pharmaceutically acceptable salt or pharmaceutically acceptable polymorph thereof.

13. The compound according to claim 12,
wherein,
$R_1$ is hydroxy or unsubstituted ($C_1$-$C_{12}$)-alkoxy;
$R_2$ is selected from nitro, NH—$SO_2$—($C_1$-$C_{12}$)-alkyl, NH—$SO_2$-aryl or $NR_aR_b$; wherein $R_a$ and $R_b$ are independently selected from hydrogen, ($C_1$-$C_{12}$)-alkyl, aralkyl, aryl or heterocyclyl;
$R_3$ is hydrogen or unsubstituted ($C_1$-$C_{12}$)-alkyl; and
n is 0 or 1;
or a stereoisomer, tautomer, pharmaceutically acceptable salt or pharmaceutically acceptable polymorph thereof.

14. The compound according to claim 1, selected from:
4-[2-(3-Methyl-[1,2,4]oxadiazol-5-yl)-vinyl]-benzene-1,2-diol;
5-[2-(3,4-Dimethoxy-phenyl)-vinyl]-3-ethyl-[1,2,4]oxadiazole;
4-[2-(3-Ethyl-[1,2,4]oxadiazol-5-yl)-vinyl]-benzene-1,2-diol;
5-[2-(3,4-Dimethoxy-phenyl)-vinyl]-3-propyl-[1,2,4]oxadiazole;
4-[2-(3-Propyl-[1,2,4]oxadiazol-5-yl)-vinyl]-benzene-1,2-diol;
3-Benzyl-5-[2-(3,4-dimethoxy-phenyl)-vinyl]-[1,2,4]oxadiazole;
4-[2-(3-Benzyl-[1,2,4]oxadiazol-5-yl)-vinyl]-benzene-1,2-diol;
5-[2-(4-Methoxy-3-nitro-phenyl)-vinyl]-3-propyl-[1,2,4]oxadiazole;
2-Methoxy-5-[2-(3-propyl-[1,2,4]oxadiazol-5-yl)-vinyl]-phenylamine;
N-{2-Methoxy-5-[2-(3-propyl-[1,2,4]oxadiazol-5-yl)-vinyl]-phenyl}-methanesulfonamide;
N-{2-Hydroxy-5-[2-(3-propyl-[1,2,4]oxadiazol-5-yl)-vinyl]-phenyl}-methanesulfonamide;
2-Nitro-4-(2-(3-propyl-1,2,4-oxadiazol-5-yl)vinyl)phenol;
5-[2-(4-Methoxy-3-nitro-phenyl)-vinyl]-3-propyl-[1,2,4]oxadiazole;
2-Amino-4-(2-(3-propyl-1,2,4-oxadiazol-5-yl)vinyl)phenol;
4-{5-[2-(3,4-Dimethoxy-phenyl)-vinyl]-[1,2,4]oxadiazol-3-ylmethyl}-piperidine-1-carboxylic acid tert-butyl ester;
4-{5-[2-(3,4-Dimethoxy-phenyl)-vinyl]-[1,2,4]oxadiazol-3-ylmethyl}-piperidine;
4-[2-(3-Piperidin-4-ylmethyl-[1,2,4]oxadiazol-5-yl)-vinyl]-benzene-1,2-diol;
4-{5-[2-(3,4-Dimethoxy-phenyl)-vinyl]-[1,2,4]oxadiazol-3-ylmethyl}-1-isopropyl-piperidine;
4-{2-[3-(1-Isopropyl-piperidin-4-ylmethyl)-[1,2,4]oxadiazol-5-yl]-vinyl}-benzene-1,2-diol;
[2-(4-{5-[2-(3,4-Dimethoxy-phenyl)-vinyl]-[1,2,4]oxadiazol-3-ylmethyl}-piperidin-1-yl)-ethyl]-dimethyl-amine,
4-(2-{3-[1-(2-Dimethylamino-ethyl)-piperidin-4-ylmethyl]-[1,2,4]oxadiazol-5-yl}-vinyl)-benzene-1,2-diol,
1-Benzyl-4-{5-[2-(3,4-dimethoxy-phenyl)-vinyl]-[1,2,4]oxadiazol-3-ylmethyl}-piperidine,
4-{2-[3-(1-Benzyl-piperidin-4-ylmethyl)-[1,2,4]oxadiazol-5-yl]-vinyl}-benzene-1,2-diol;
5-[2-(3,4-Dimethoxy-phenyl)-vinyl]-3-nonyl-[1,2,4]oxadiazole;
4-[2-(3-Nonyl-[1,2,4]oxadiazol-5-yl)-vinyl]-benzene-1,2-diol;
3-Cyclopropyl-5-[2-(3,4-dimethoxy-phenyl)-vinyl]-[1,2,4]oxadiazole;
4-[2-(3-Cyclopropyl-[1,2,4]oxadiazol-5-yl)-vinyl]-benzene-1,2-diol;
5-[2-(3,4-Dimethoxy-phenyl)-vinyl]-3-pentyl-[1,2,4]oxadiazole;
4-[2-(3-Pentyl-[1,2,4]oxadiazol-5-yl)-vinyl]-benzene-1,2-diol,
5-[2-(3,4-Dimethoxy-phenyl)-vinyl]-3-hexyl-[1,2,4]oxadiazole;
4-[2-(3-Hexyl-[1,2,4]oxadiazol-5-yl)-vinyl)]-benzene-1,2-diol;
3-Cyclohexylmethyl-5-[2-(3,4-dimethoxy-phenyl)-vinyl]-[1,2,4]oxadiazole;
4-[2-(3-Cyclohexylmethyl-[1,2,4]oxadiazol-5-yl)-vinyl]benzene-1,2-diol;
5-[2-(3,4-Dimethoxy-phenyl)-vinyl]-3-octyl-[1,2,4]oxadiazole;
4-[2-(3-Octyl-[1,2,4]oxadiazol-5-yl)-vinyl]-benzene-1,2-diol;
5-[2-(3,4-Dimethoxy-phenyl)-vinyl]-3-heptyl-[1,2,4]oxadiazole;
4-[2-(3-Heptyl-[1,2,4]oxadiazol-5-yl)-vinyl]-benzene-1,2-diol;
3-Cycloheptyl-5-[2-(3,4-dimethoxy-phenyl)-vinyl]-[1,2,4]oxadiazole;
4-[2-(3-Cycloheptyl-[1,2,4]oxadiazol-5-yl)-vinyl]-benzene-1,2-diol;
3-Cyclohexyl-5-[2-(3,4-dimethoxy-phenyl)-vinyl]-[1,2,4]oxadiazole;
4-[2-(3-Cyclohexyl-[1,2,4]oxadiazol-5-yl)-vinyl]-benzene-1,2-diol;

or a stereoisomer, tautomer, pharmaceutically acceptable salt or pharmaceutically acceptable polymorph thereof.

15. The compound according to claim 14, selected from:
4-[2-(3-Methyl-[1,2,4]oxadiazol-5-yl)-vinyl]-benzene-1,2-diol;
4-[2-(3-Ethyl-[1,2,4]oxadiazol-5-yl)-vinyl]-benzene-1,2-diol;
4-[2-(3-Propyl-[1,2,4]oxadiazol-5-yl)-vinyl]-benzene-1,2-diol;
4-[2-(3-Benzyl-[1,2,4]oxadiazol-5-yl)-vinyl]-benzene-1,2-diol;
N-{2-Hydroxy-5-[2-(3-propyl-[1,2,4]oxadiazol-5-yl)-vinyl]-phenyl}-methanesulfonamide;
2-Nitro-4-(2-(3-propyl-1,2,4-oxadiazol-5-yl)vinyl)phenol;
2-Amino-4-(2-(3-propyl-1,2,4-oxadiazol-5-yl)vinyl)phenol;
4-[2-(3-Piperidin-4-ylmethyl-[1,2,4]oxadiazol-5-yl)-vinyl]-benzene-1,2-diol;
4-{2-[3-(1-Isopropyl-piperidin-4-ylmethyl)-[1,2,4]oxadiazol-5-yl]-vinyl}-benzene-1,2-diol;
4-(2-{3-[1-(2-Dimethylamino-ethyl)-piperidin-4-ylmethyl]-[1,2,4]oxadiazol-5-yl}-vinyl)-benzene-1,2-diol;
4-{2-[3-(1-Benzyl-piperidin-4-ylmethyl)-[1,2,4]oxadiazol-5-yl]-vinyl}-benzene-1,2-diol;
4-[2-(3-Nonyl-[1,2,4]oxadiazol-5-yl)-vinyl]-benzene-1,2-diol;
4-[2-(3-Cyclopropyl-[1,2,4]oxadiazol-5-yl)-vinyl]-benzene-1,2-diol;
4-[2-(3-Pentyl-[1,2,4]oxadiazol-5-yl)-vinyl]-benzene-1,2-diol;
4-[2-(3-Hexyl-[1,2,4]oxadiazol-5-yl)-vinyl]-benzene-1,2-diol;
4-[2-(3-Cyclohexylmethyl-[1,2,4]oxadiazol-5-yl)-vinyl]-benzene-1,2-diol;
4-[2-(3-Octyl-[1,2,4]oxadiazol-5-yl)-vinyl]-benzene-1,2-diol;
4-[2-(3-Heptyl-[1,2,4]oxadiazol-5-yl)-vinyl]-benzene-1,2-diol;
4-[2-(3-Cycloheptyl-[1,2,4]oxadiazol-5-yl)-vinyl]-benzene-1,2-diol;
4-[2-(3-Cyclohexyl-[1,2,4]oxadiazol-5-yl)-vinyl]-benzene-1,2-diol;
or a stereoisomer, tautomer, pharmaceutically acceptable salt or pharmaceutically acceptable polymorph thereof.

16. A pharmaceutical composition, comprising a therapeutically effective amount of a compound, according to claim 1, or a stereoisomer, tautomer, pharmaceutically acceptable salt or pharmaceutically acceptable polymorph thereof, as an active ingredient, either alone or with at least one pharmaceutically acceptable excipient.

* * * * *